US012624111B2

(12) United States Patent
Burger et al.

(10) Patent No.: US 12,624,111 B2
(45) Date of Patent: May 12, 2026

(54) METHODS FOR TREATING METASTATIC COLON CANCER WITH LERONLIMAB

(71) Applicant: CytoDyn Inc., Vancouver, WA (US)

(72) Inventors: Denis Burger, Vancouver, WA (US);
Scott Kelly, Vancouver, WA (US)

(73) Assignee: CytoDyn Inc., Vancouver, WA (US)

( * ) Notice: Subject to any disclaimer, the term of this patent is extended or adjusted under 35 U.S.C. 154(b) by 864 days.

(21) Appl. No.: 17/631,161

(22) PCT Filed: Jul. 31, 2020

(86) PCT No.: PCT/US2020/044616
§ 371 (c)(1),
(2) Date: Jan. 28, 2022

(87) PCT Pub. No.: WO2021/026028
PCT Pub. Date: Feb. 11, 2021

(65) Prior Publication Data
US 2022/0298249 A1 Sep. 22, 2022

Related U.S. Application Data

(60) Provisional application No. 63/047,693, filed on Jul. 2, 2020, provisional application No. 62/882,353, filed on Aug. 2, 2019.

(51) Int. Cl.
C07K 16/28 (2006.01)
A61P 35/04 (2006.01)

(52) U.S. Cl.
CPC .......... C07K 16/2866 (2013.01); A61P 35/04 (2018.01)

(58) Field of Classification Search
CPC . A61P 35/04; C07K 16/2866; C07K 2317/24; C07K 2317/76; A61K 2039/505; A61K 39/3955
See application file for complete search history.

(56) References Cited

FOREIGN PATENT DOCUMENTS

WO      WO2007144720      * 12/2007

OTHER PUBLICATIONS

Jiao et al., Abstract 2009: Leronlimab, a humanized monoclonal antibody to CCR5, blocks breast cancer cellular invasion and enhances cell death induced by DNA damaging chemotherapies, Tumor biology, Jul. 1, 2019, Abs. 2009. (Year: 2019).*
Jiao et al., Leronlimab, a humanized monoclonal antibody to CCR5, blocks breast cancer cellular invasion and enhances cell death induced by DNA damaging chemotherapies. Abstract 2009, Cancer Res. 79, 2009. (Year: 2009).*
Halama et al., Tumoral immune cell exploitation in colorectal cancer metastases can be targeted effectively by anti-CCR5 therapy in cancer patients. Cancer Cell 29, 587-601, 2016. (Year: 2016).*
Velasco-Velazquez et al: "CCR5 antagonist blocks metastasis of basal breast cancer cells", Cancer Research, 72, 3839-3850, 2012 . (Year: 2012).*
Sicoli et al. "CCR5 receptor antagonists block metastasis to bone of v-src oncogene-transformed metastatic prostate cancer cell lines", Cancer Research, 74, 7103-7114, 2014. (Year: 2014).*

* cited by examiner

Primary Examiner — Elly-Gerald Stoica
(74) Attorney, Agent, or Firm — Seed IP Law Group LLP

(57) ABSTRACT
The present disclosure relates to the use of competitive inhibitors of the CCR5 receptor, such as the monoclonal antibody leronlimab, or binding fragments thereof, in the treatment or prevention of cancer.

22 Claims, 25 Drawing Sheets

Specification includes a Sequence Listing.

METHODS FOR TREATING METASTATIC COLON CANCER WITH LERONLIMAB

STATEMENT REGARDING SEQUENCE LISTING

The Sequence Listing associated with this application is provided in text format in lieu of a paper copy, and is hereby incorporated by reference into the specification. The name of the text file containing the Sequence Listing is 230042_429USPC_SEQUENCE_LISTING.txt. The text file is 16 KB, was created on Jan. 20, 2022, and is being submitted electronically via EFS-Web.

BACKGROUND

Technical Field

The present disclosure relates to the use of competitive inhibitors of the CCR5 receptor, such as the monoclonal antibody leronlimab, in the treatment or prevention of cancer.

Background

Inflammation may occur in response to trauma, chemical or physical injury, autoimmune responses, infectious agents, cancer, etc. Inflammation is an important component of innate immunity and is necessary for priming adaptive immunity and for the effector phase of the immune response. Soluble mediators, such as chemokines, are shown to play an important role in driving the various components of inflammation, especially leukocyte influx.

Chemokines bind to their receptors which are expressed on many cell types, including, for example, leukocytes, endothelial cells, fibroblasts, epithelial, smooth muscle, and parenchymal cells. Chemokines play an important role in leukocyte biology, by controlling cell recruitment and activation in basal and in inflammatory circumstances. In addition, because chemokine receptors are expressed on other cell types, chemokines have multiple other roles, including angiogenesis, tissue and vascular remodeling, pathogen elimination, antigen presentation, leukocyte activation and survival, chronic inflammation, tissue repair/healing, fibrosis, embryogenesis, tumorigenesis, etc.

CCL5 (C-C chemokine ligand 5), an inflammatory chemokine also known as regulated upon activation and normal T cell expressed and secreted (RANTES), plays an important role in these immunologic mechanisms. CCL5 acts as a key regulator of T cell migration to inflammatory sites, directing migration of T cells to damaged or infected sites. CCL5 also regulates T cell differentiation. Many biologic effects of chemokines are mediated by their interaction with chemokine receptors on cell surfaces. In the present invention, the most relevant known receptor for CCL5 is the CCR5 receptor; however, CCR1 and CCR3 are also known CCL5 receptors and CCR4 and CD44 are auxiliary receptors. Tamamis et al., *Elucidating a KeyAnti-HIV*-1 *and Cancer-Associated Axis: The Structure of CCL5 (Rantes) in Complex with CCR5*, Scientific Reports, 4: 5447 (2014).

Inflammatory chemokines have long been viewed mainly as indispensable "gate keepers" of immunity and inflammation. However, recent research indicates that, for example, cancer cells subvert the normal chemokine system and these molecules and their receptors become important constituents of the tumor microenvironment with very different ways to exert tumor-promoting roles. While the CCR5 receptor and the CCL5 ligand have been detected in some hematological malignancies, lymphomas, and a great number of solid tumors, extensive studies on the role of the CCL5 ligand/ CCR5 receptor axis have only been performed in only a limited number of cancers. Aldinucci et al., *The Inflammatory chemokine CCL5 and Cancer Progression*, Mediators of Inflammation, vol. 2014, article ID 292376, 12 pages.

The CCR5 receptor is a C-C chemokine G-coupled protein receptor expressed on lymphocytes (e.g., NK cells, B cells), monocytes, macrophages, dendritic cells, a subset of T cells, etc. The CCR5 receptor spans the cellular plasma membrane seven times in a serpentine manner. The extracellular portions represent potential targets for antibodies targeting CCR5, and comprise an amino-terminal domain (Nt) and three extracellular loops (ECL1, ECL2, and ECL3). The extracellular portions of CCR5 comprise just 90 amino acids distributed over four domains. The largest of these domains are at the Nt and ECL2 at approximately 30 amino acids each. Olson et al., *CCR5 Monoclonal Antibodies for HIV*-1 *Therapy*, Curr. Opin. HIV AIDS, March, 4(2): 104-111 (2009).

The formation of the CCL5 ligand and CCR5 receptor complex causes a conformational change in the receptor that activates the subunits of the G-protein, inducing signaling and leading to changed levels of cyclic AMP (cAMP), inositol triphosphate, intracellular calcium, and tyrosine kinase activation. These signaling events cause cell polarization and translocation of the transcription factor NF-kB, which results in the increase of phagocytic ability, cell survival, and transcription of proinflammatory genes. Once G-protein dependent signaling occurs, the CCL5/CCR5 receptor complex is internalized via endocytosis.

A complete complex structure of CCL5 in complex with CCR5 has been computationally derived. It is reported that the 1-15 residue moiety of CCL5 is inserted into the CCR5 binding pocket; the 1-6 N-terminal domain of CCL5 is buried within the transmembrane region of CCR5; and the 7-15 residue moiety of CCL5 is predominantly encompassed by the N-terminal domain and extracellular loops of CCR5. CCL5 residues Ala16 and Arg17 and additional residues of the 24-50 residue moiety interact with the upper N-terminal domain and extracellular loop interface of CCR5. It is further reported that the integrity of the amino terminus of CCL5 is crucial to receptor binding and cellular activation. Further, it has been reported that CCL5 and HIV-1 primarily interact with mostly the same CCR5 residues, and share the same chemokine receptor binding pocket. See Tamamis et al., *Elucidating a Key Anti-HIV*-1 *and Cancer-Associated Axis: The Structure of CCL5 (Rantes) in Complex with CCR5*, Scientific Reports, 4:5447 (2014). It is also separately reported that chemokines, such as the CCL5 ligand, principally bind the CCR5 receptor through ECL2. Olson et al., *CCR5 Monoclonal Antibodies for HIV*-1 *Therapy*, Curr. Opin., HIV AIDS, March, 4(2): 104-111 (2009).

Some studies have indicated that CCR5 signaling has anti-tumor effects, acting as a co-stimulatory molecule for T cell activation and increasing T cell chemotaxis to the tumor microenvironment. See Gao et al., *CCL5 activation of CCR5 regulates cell metabolism to enhance proliferation of breast cancer cells*, Open Biol., 6: 160122 (2016); Gonzalez-Martin et al., *CCR5 in cancer immunotherapy: More than an "attractive" receptor for T cells*, Oncoimmunology, 1: 106-108 (2012). However, evidence also suggests that CCL5/ CCR5 axis signaling may be preferentially activated in certain types of cancers, for example breast and prostate cancers, and that such signaling facilitates disease progression. For example, some studies indicate that cancer cells can overexpress CCL5, CCR5, or both, likely contributing to their growth and proliferation via the effects of CCR5 signaling on mechanistic target of rapamycin (mTOR). See Gao et al., *CCL5 activation of CCR5 regulates cell metabolism to enhance proliferation of breast cancer cells*, OPEN BIOL., 6: 160122 (2016); see also Chow and Luster, *Chemokines in Cancer*, CANCER IMMUNOL. RES., 2(12): 1125-1131 (2014); Singh et al., *Expression of CCR5 and its ligand CCL5 in pancreatic cancer (Abstract)*, J IMMUNOL, 196(1 Supplement): 51.3 (2016). Additionally, some immunosuppressive immune cells, including regulatory T cells (Treg) and myeloid-derived suppressor cells (MDSC), express CCR5, suggesting another pathway by which CCR5 signaling may contribute to tumor growth. Mukaida, *CCR5 antagonist, an ally to fight against metastatic colorectal cancer*, TRANSLATIONAL CANCER RESEARCH, 5(Supp. 2): S309-S312 (2016). Furthermore, it has been reported that cancer cells in the tumor microenvironment can exploit CCL5 production by CD4$^+$ and CD8$^+$ T cells to lead to increased tumor growth and tumor cell spreading. Halama et al., *Tumoral Immune Cell Exploitation in Colorectal Cancer Metastases Can Be Targeted Effectively by Anti-CCR5 Therapy in Cancer Patients*, CANCER CELL, 29: 587-601 (2016).

Exploratory efforts using anti-CCR5 binding agents to alter CCL5/CCR5 signaling in connection with some cancer types have been made. Sicoli et al., *CCR5 Receptor Antagonists Block Metastasis to Bone of v-Src Oncogene-Transformed Metastatic Prostate Cancer Cell Lines*, CANCER RES., 74(23): 7103-7114 (2014); Velasco-Velázquez et al., *The CCL5/CCR5 Axis Promotes Metastasis In Basal Breast Cancer*, ONCOIMMUNOLOGY, 2(4): e23660 (2013); Velasco-Velázquez et al., *CCR5 Antagonist Blocks Metastasis of Basal Breast Cancer Cells*, CANCER RES., 72(15): 3839-3850 (2012). Various compounds exist that inhibit, interrupt, block, alter, or modify the CCR5/CCL5 receptor/ligand axis (i.e., CCR5 receptor/CCL5 ligand axis). Many of these compounds have been developed for the treatment of HIV-1, which also binds with the CCR5 receptor and is known to share some binding commonalities with CCL5. Such compounds include extracellular or cell transmembrane CCR5 binding agents such as, for example, leronlimab (extracellular) and maraviroc (transmembrane), and other compounds such as vicriviroc, aplaviroc, SCH-C, and TAK-779, and antibodies such as PA14, 2D7, RoAb13, RoAb14, 45523, etc. It has been found that the most potently antiviral anti-CCR5 monoclonal antibodies including, for example, leronlimab (also referred to as PRO 140), bind CCR5 receptor amino acid residues in EL2 alone or in combination with Nt residues. It has also been determined that the CCR5 receptor binding sites for anti-CCR5 monoclonal antibodies are distinct from those of small-molecule CCR5 antagonists. That is, available small-molecule CCR5 antagonists, such as maraviroc, bind the hydrophobic cavity formed by the transmembrane helices, i.e., not the extracellular Nt or loop regions. The amino acid residue E283 in the seventh transmembrane region has been specifically identified as a principle site or interaction for small molecules, and maraviroc and vicriviroc have been found to bind to identical sets of CCR5 receptor amino acids. Olson et al., *CCR5 Monoclonal Antibodies for HIV-1 Therapy*, CURR. OPIN. HIV AIDS, March, 4(2): 104-111 (2009). It has also been reported, however, that the CCL5 ligand and maraviroc dock on the CCR5 receptor by sharing two receptor sites: the Nt and the ECL2, and that synthetic CCL5-derived peptides may also be used to block the CCR5 receptor. Secchi et al., *Combi-*

*nation of the CCL5-Derived Peptide R4.0 with Different HIV-1 Blockers Reveals Wide Target Compatibility and Synergic Cobinding to CCR5*, ANTIMICROB AGENTS CHEMOTHER., 58(10): 6215-6223 (2014).

In some instances, CCL5 expression associated with immune cell activation can be exploited by cancer cells in the tumor microenvironment, and blocking CCR5 signaling using inhibitors such as maraviroc may have anti-tumor effects. In a study of human colorectal cancer liver metastasis, CD4$^+$ and CD8$^+$ T cells at the invasive margin expressed CCL5, which was associated with T cell exhaustion, tumor proliferation, invasive tumor cell behavior, and increased production of matrix metalloproteinases by tumor-associated macrophages. Halama et al., *Tumoral Immune Cell Exploitation in Colorectal Cancer Metastases Can Be Targeted Effectively by Anti-CCR5 Therapy in Cancer Patients*, CANCER CELL, 29: 587-601 (2016). Inhibiting CCL5 with maraviroc led to repolarization of tumor-associated macrophages and tumor cell death. Halama et al. (2016).

However, inhibition of CCR5 signaling can also have immunosuppressive effects. In vitro studies have been conducted to investigate the effects of CCR5 receptor blockade by maraviroc on activated human T cells on potential immunological mechanisms. It was found that blocking CCR5 by maraviroc not only can block CCR5 and CCR2 internalization processes induced by CCL5 and CCL2, but can also inhibit T cell chemotactic activities toward their cognate ligands, respectively. Further, blocking CCR5 with maraviroc at high doses tends to decrease production of TNF-α and IFN-γ. It was also noted that the effect of maraviroc on CCR5 was temporary and reversible. Yuan et al., *In Vitro Immunological Effects of Blocking CCR5 on T Cells*, INFLAMMATION, 38(2): 902-910 (2015); see Arberas et al., *In vitro effects of the CCR5 inhibitor maraviroc on human T cell function*, J. ANTIMICROB. CHEMOTHER., 68(3): 577-586 (2013).

CCR5 is also thought to play a role in graft-versus-host disease (GVHD). Chemokine receptor CCR5 has been shown to mediate murine GVHD pathogenesis. It is reported that infiltrating lymphocytes in the skin of human acute GVHD samples are predominantly CCR5$^+$ T cells. Lisa Palmer, George Sale, John Balogun, Dan Li, Dan Jones, Jeffrey Molldrem, Rainer Storb, Qing Ma, *Chemokine Receptor CCR5 Mediates Allo-Immune Responses in Graft-vs-Host Disease*, Biol Blood Marrow Transplant. 2010 March; 16(3): 311-319, doi: 10.1016/j.bbmt2009.12.002. It has also been found that the CCR5$^+$ population exhibits the characteristics of the activated effector T cell phenotype. CCR5 expression is upregulated upon allogenic stimulation, and CCR5$^+$ cells are proliferating with co-expression of T cell activation markers. Furthermore, the activated T cells producing inflammatory cytokine TNFα, IL-2 or IFN-γ, are positive for CCR5. Thus, it is understood that CCR5 is a marker for GVHD effector cells, and CCR5$^+$ T cells are active participants in the pathogenesis of human acute GVHD.

In view of the numerous and sometimes contradictory roles of CCR5 signaling in contributing to tumor development, there exists a need for competitive inhibitors to the CCR5 receptor and methods of use that can be used to inhibit, dampen, interrupt, block, alter, or modify the CCR5/CCL5 receptor/ligand axis for therapeutic purposes without triggering, or that reduce the impact of, unintended side effects. Further, there is a need for such competitive inhibitors to the CCR5 receptor and methods of use that cause fewer and less severe side effects, are longer-lasting, and facilitate improved patient compliance due to decreased dosing demands and improved patient experience (due to fewer undesirable side effects), including side effects caused by the competitive inhibitor itself. Optimal therapeutic modalities using the CCL5/CCR5 axis as a therapeutic target will need to accommodate two opposing demands: the need to inhibit the detrimental involvement of CCL5 and CCR5 in specific malignant diseases while protecting their potentially beneficial activities in immunity.

BRIEF SUMMARY

It has previously been shown that the monoclonal antibody leronlimab does not affect cAMP levels when added to CD4$^+$ T cells alone, but diminishes the effect of CCL5 on cAMP levels when administered with CCL5. WO2016/210130. Similarly, although leronlimab alone does not affect chemotaxis of CHO-K1 cells, leronlimab reduces CCL5-induced chemotaxis when administered with CCL5. WO2016/210130. These studies indicate that leronlimab does not have agonist activity for CCR5 but acts as a competitive inhibitor with CCL5 for binding to CCR5.

In the present disclosure, however, it is shown that leronlimab alone does not affect tyrosine kinase phosphorylation downstream of CCR5 receptor signaling in T cells in vitro, and that it also does not inhibit phosphorylation of such kinases by CCL5. These results provide evidence that the role of leronlimab in modulating the CCR5/CCL5 axis relative to RANTES is inconsistent, i.e., that it blocks or inhibits only some of the downstream activities that would otherwise result from CCL5/CCR5 binding. Thus, it is shown that leronlimab's activity as a CCL5 competitive binding inhibitor has a mixed impact on CCL5's ability to participate in downstream activity conventionally associated with the CCR5/CCL5 axis. Further elucidation of the role of leronlimab and its immunomodulatory effects is the subject of continued investigation.

Additionally, in the present disclosure, leronlimab was found to be unexpectedly effective in preventing tumor growth in mouse models lacking T cells, indicating that leronlimab also modulates immunological responses and promote anti-tumor effects through NK cells, B cells, or both. Accordingly, the ability of leronlimab to modulate activity triggered by binding the CCR5 axis on non-T cells, for example, on NK cells, B cells, or both, was determined. Also, importantly, it was found that leronlimab is surprisingly effective in preventing tumor growth in mouse models based solely on its activity relative to non-T cells; thus, suggesting a non-T cell therapeutic approach.

The present disclosure further shows that, while CCR5 expression is associated with accelerated tumor growth, leronlimab both slows development of xGVHD (xenograft-GVHD) and enhances anti-tumor activity in humanized mice. It was found that leronlimab delayed the onset of xGVHD in both SW480 tumor-bearing and non-tumor-bearing mice. Additionally, it was found that leronlimab effectively delayed tumor progression in humanized mice, with the effect persisting to day 80, but had no effect on tumor growth in non-humanized mice. Analysis of the peripheral blood from tumor-bearing humanized mice treated with leronlimab showed increased numbers of circulating T cells and decreased percentages of B and NK cells. More detailed analysis showed an increase in CD4+ CD25+ Tregs and a decrease in CD4+CD25− Tregs, which may relate to the suppression of GVHD by leronlimab.

The present disclosure also demonstrates that leronlimab reduced metastatic burden in humanized mice engrafted with SW480 human colon carcinoma cells. The degree of tumor inhibition in metastatic lesions (may also be referred to as secondary site lesions) was surprisingly more pronounced as compared to the growth inhibition of the primary tumors. Because tumor neoangiogenesis is required for tumor growth and metastasis, the effect of leronlimab on angiogenesis was assessed. It was found that leronlimab interferes with tumor angiogenesis, which suggests a mechanism for the reduction of metastatic burden observed.

Accordingly, in certain aspects, the present disclosure is directed to the use of competitive inhibitors of the CCR5 receptor, such as the monoclonal antibody leronlimab, or binding fragments thereof, in the treatment or prevention of cancer and/or GVHD.

In some embodiments, the present disclosure provides a method of treating, inhibiting, or preventing colon cancer metastasis comprising administering to a subject in need thereof an anti-CCR5 cell receptor binding agent comprising:

(a) a leronlimab antibody, or binding fragment thereof; (b) a nucleic acid encoding a leronlimab antibody, or binding fragment thereof; (c) a vector comprising a nucleic acid encoding a leronlimab antibody, or binding fragment thereof; (d) a host cell comprising (i) a leronlimab antibody, or binding fragment thereof, (ii) a nucleic acid encoding a leronlimab antibody, or binding fragment thereof, or (iii) a vector comprising a nucleic acid encoding a leronlimab antibody, or binding fragment thereof; or (e) an anti-CCR5 cell receptor binding agent that does not have CCL5 agonist activity.

In some embodiments, the present disclosure provides a method of reducing metastatic burden in a subject having colon cancer, comprising administering to a subject in need thereof an anti-CCR5 cell receptor binding agent comprising: (a) a leronlimab antibody, or binding fragment thereof; (b) a nucleic acid encoding a leronlimab antibody, or binding fragment thereof; (c) a vector comprising a nucleic acid encoding a leronlimab antibody, or binding fragment thereof; (d) a host cell comprising (i) a leronlimab antibody, or binding fragment thereof, (ii) a nucleic acid encoding a leronlimab antibody, or binding fragment thereof, or (iii) a vector comprising a nucleic acid encoding a leronlimab antibody, or binding fragment thereof; or (e) an anti-CCR5 binding agent that does not have CCL5 agonist activity.

In some embodiments, the present disclosure provides a method of reducing tumor-associated angiogenesis in a subject having colon cancer, comprising administering to a subject in need thereof an anti-CCR5 cell receptor binding agent comprising: (a) a leronlimab antibody, or binding fragment thereof; (b) a nucleic acid encoding a leronlimab antibody, or binding fragment thereof; (c) a vector comprising a nucleic acid encoding a leronlimab antibody, or binding fragment thereof; (d) a host cell comprising (i) a leronlimab antibody, or binding fragment thereof, (ii) a nucleic acid encoding a leronlimab antibody, or binding fragment thereof, or (iii) a vector comprising a nucleic acid encoding a leronlimab antibody, or binding fragment thereof; or (e) an anti-CCR5 binding agent that does not have CCL5 agonist activity.

In some embodiments, the present disclosure provides for the use of: (a) a leronlimab antibody, or binding fragment thereof; (b) a nucleic acid encoding a leronlimab antibody, or binding fragment thereof; (c) a vector comprising a nucleic acid encoding a leronlimab antibody, or binding fragment thereof; (d) a host cell comprising (i) a leronlimab antibody, or binding fragment thereof, (ii) a nucleic acid encoding a leronlimab antibody, or binding fragment thereof, or (iii) a vector comprising a nucleic acid encoding a leronlimab antibody, or binding fragment thereof; or (e) an anti-CCR5 binding agent that does not that does not have CCL5 agonist activity, for treatment, inhibition, or prevention of metastatic colon cancer.

In some embodiments, the present disclosure provides a method of treating, inhibiting, or preventing growth of a metastatic cancer lesion comprising administering to a subject in need thereof a competitive inhibitor to a CCR5 cell receptor that does not have CCL5 agonist activity.

In some embodiments, the present disclosure provides a method of preventing spread of a metastatic cancer comprising administering to a subject in need thereof an anti-CCR5 cell receptor binding agent comprising: (a) a leronlimab antibody, or binding fragment thereof; (b) a nucleic acid encoding a leronlimab antibody, or binding fragment thereof; (c) a vector comprising a nucleic acid encoding a leronlimab antibody, or binding fragment thereof; (d) a host cell comprising (i) a leronlimab antibody, or binding fragment thereof, (ii) a nucleic acid encoding a leronlimab antibody, or binding fragment thereof, or (iii) a vector comprising a nucleic acid encoding a leronlimab antibody, or binding fragment thereof; or (e) an anti-CCR5 binding agent that does not have CCL5 agonist activity.

In some embodiments, the present disclosure provides a method of targeting anti-CCR5 binding agents to CCR5 receptors on any of NK cells or B cells to prevent a cancer.

In some embodiments, the present disclosure provides a therapeutic composition for treatment of a cancer comprising a competitive inhibitor to a CCR5 cell receptor that does not alter tyrosine kinase phosphorylation in CD4+ T cells.

μM) for 15 min prior to fixation and staining to quantify protein phosphorylation. Results are shown as fold phosphorylation vs. respective untreated controls. One-way ANOVA analysis was used to determine if statistically significant changes in phosphorylation occurred; no significant changes were detected.

Figure 6:
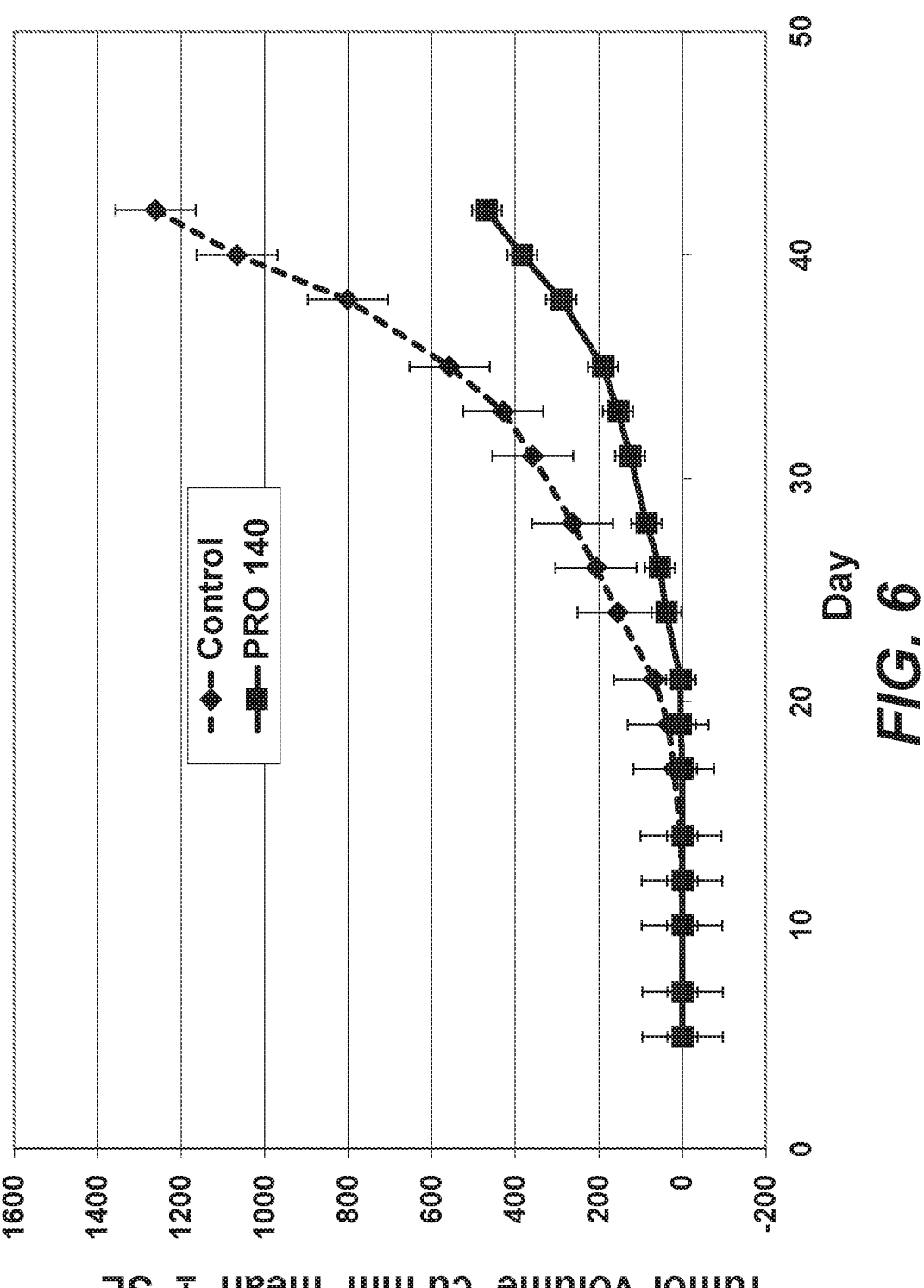

FIG. 6 shows tumor volume in male NCr nu/nu mice inoculated with SW480 human colon carcinoma cells and then administered either 2 mg leronlimab or 2 mg non-specific control antibody (IgG) two times per week beginning on day 1 after inoculation. At 42 days post-inoculation, the tumor volume of mice administered leronlimab was significantly lower than that of mice treated with a control antibody. N=16 tumors/group; p=0.014.

Figure 7:
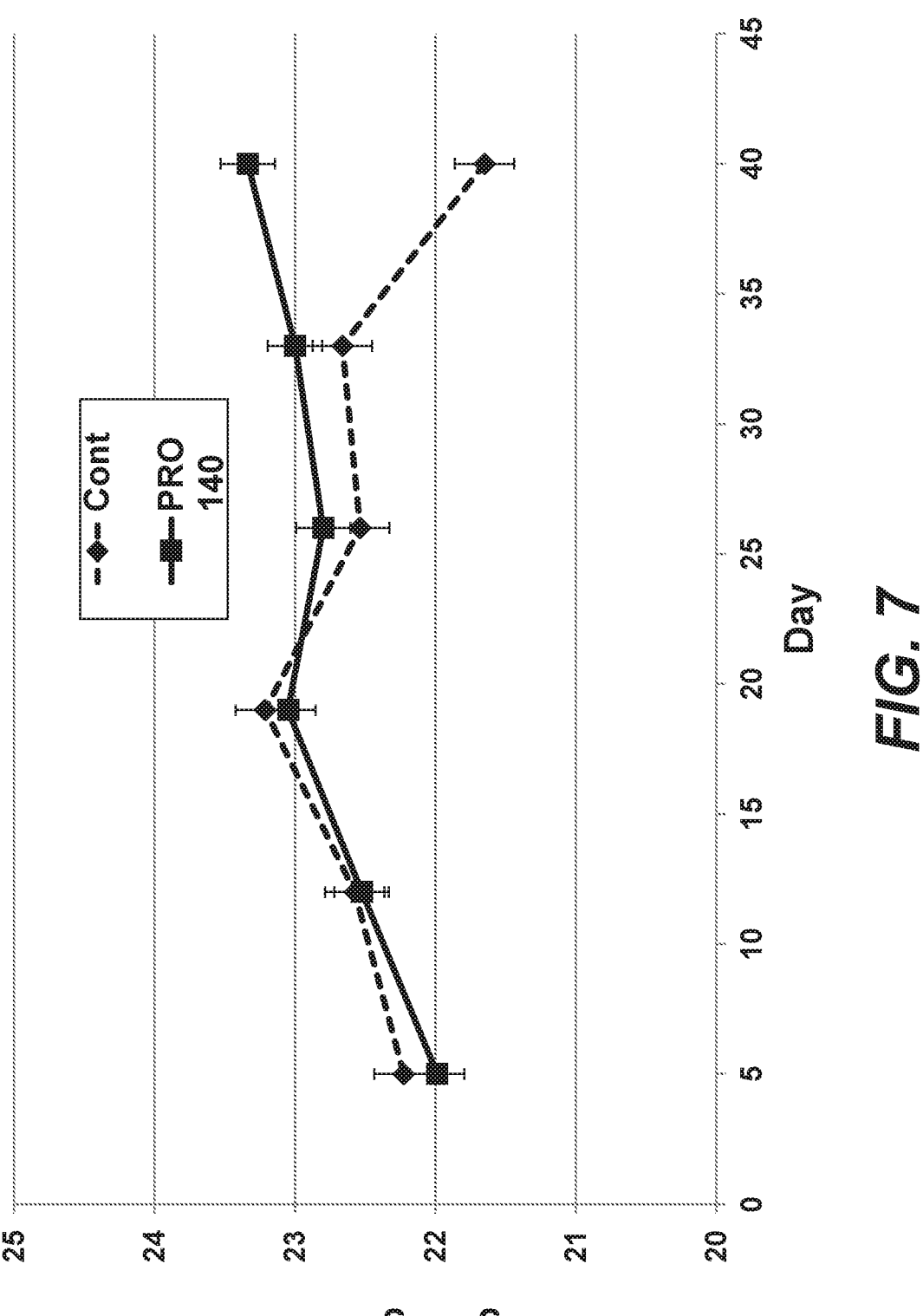

FIG. 7 shows mouse weight over the course of the study for male NCr nu/nu mice inoculated with SW480 human colon carcinoma cells and then administered 2 mg leronlimab or 2 mg non-specific control antibody (IgG) two times per week beginning on day 1 after inoculation. The mice treated with leronlimab did not lose weight over the study, while the weight of mice receiving the control antibody was significantly lower than the weight of mice treated with leronlimab by 40 days post-inoculation. N=16 tumors/group; p=0.047.

Figure 8:
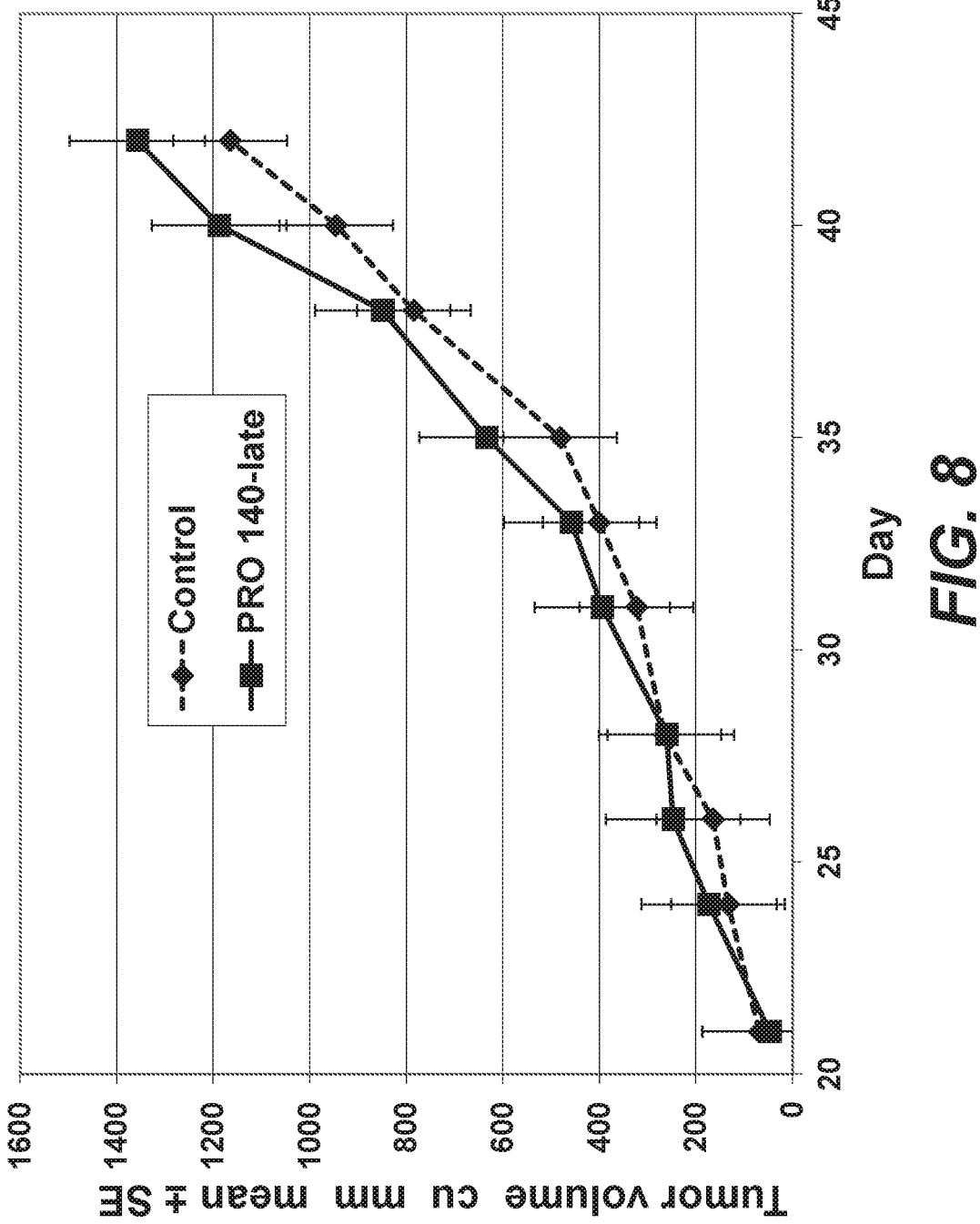

FIG. 8 shows tumor volume in male NCr nu/nu mice inoculated with SW480 human colon carcinoma cells and then administered either 2 mg leronlimab or 2 mg non-specific control antibody (IgG) two times per week beginning on day 21 after inoculation. At 42 days post-inoculation, mean tumor volume did not differ between the two groups. N=8 tumors/group; p=0.719.

Figure 9:
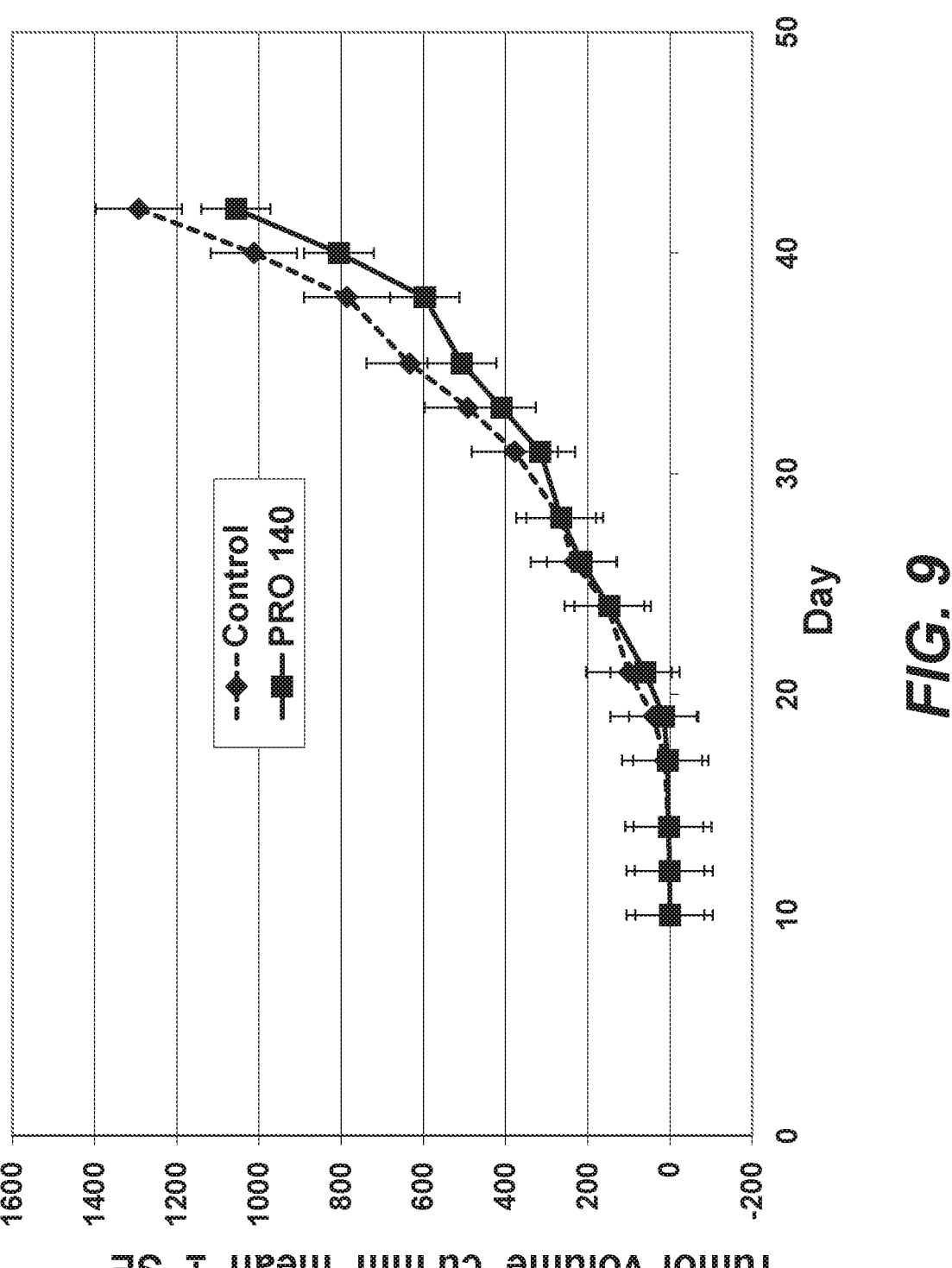

FIG. 9 shows tumor volume in male NCr nu/nu mice inoculated with SW480 human colon carcinoma cells and then administered either 0.2 mg leronlimab or 0.2 mg non-specific control antibody (IgG) two times per week beginning on day 1 after inoculation. At 42 days post-inoculation, mean tumor volume did not differ between the two groups. N=16 tumors/group; p=0.272.

Figure 10:
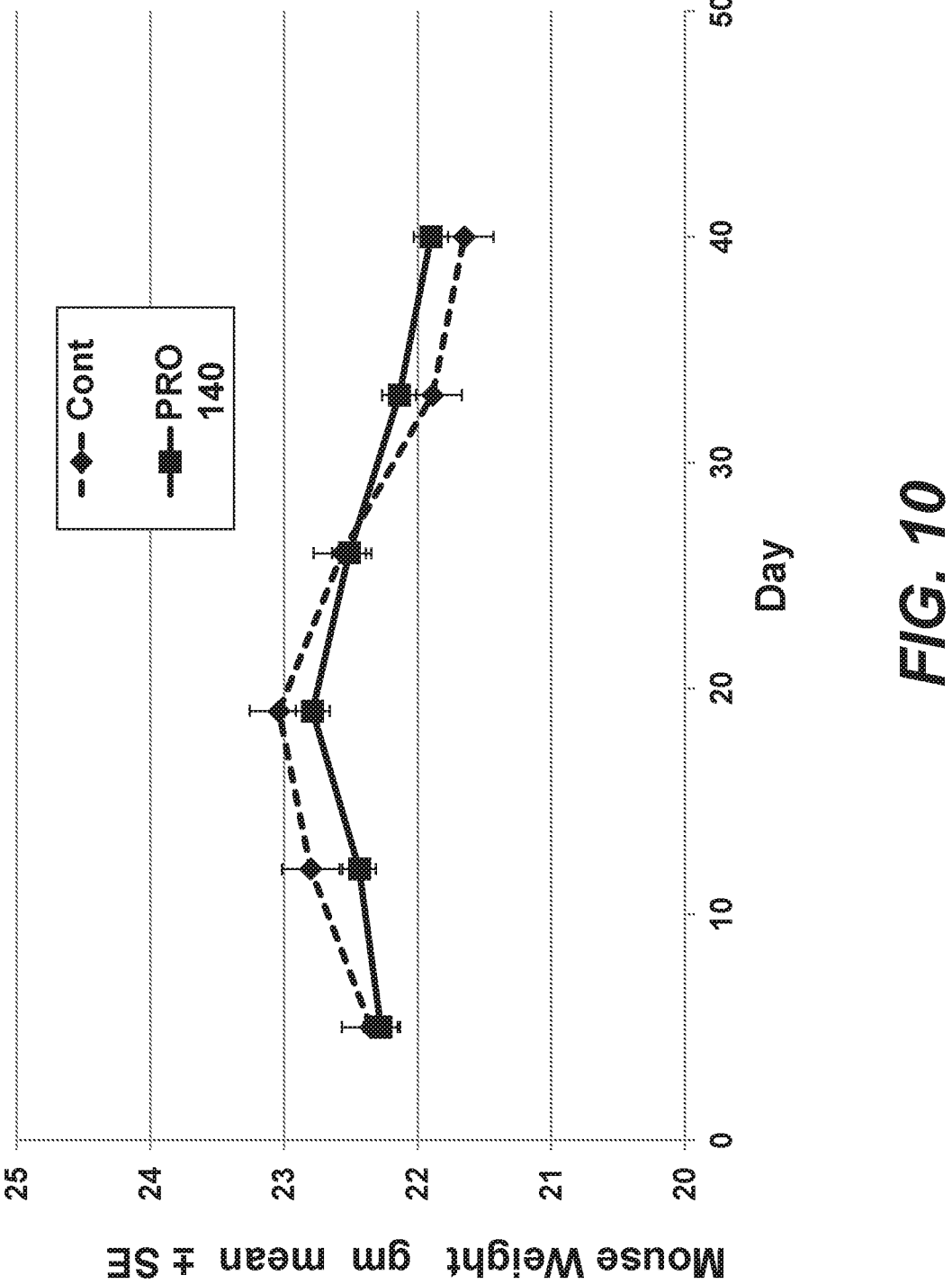

FIG. 10 shows mouse weight over the course of the study for male NCr nu/nu mice inoculated with SW480 human colon carcinoma cells and then administered either 0.2 mg leronlimab or 0.2 mg non-specific control antibody (IgG) beginning on day 1 after inoculation. At 40 days post-inoculation, mean mouse weight did not differ between the two groups. N=16 tumors/group; p=0.708.

Figure 11:
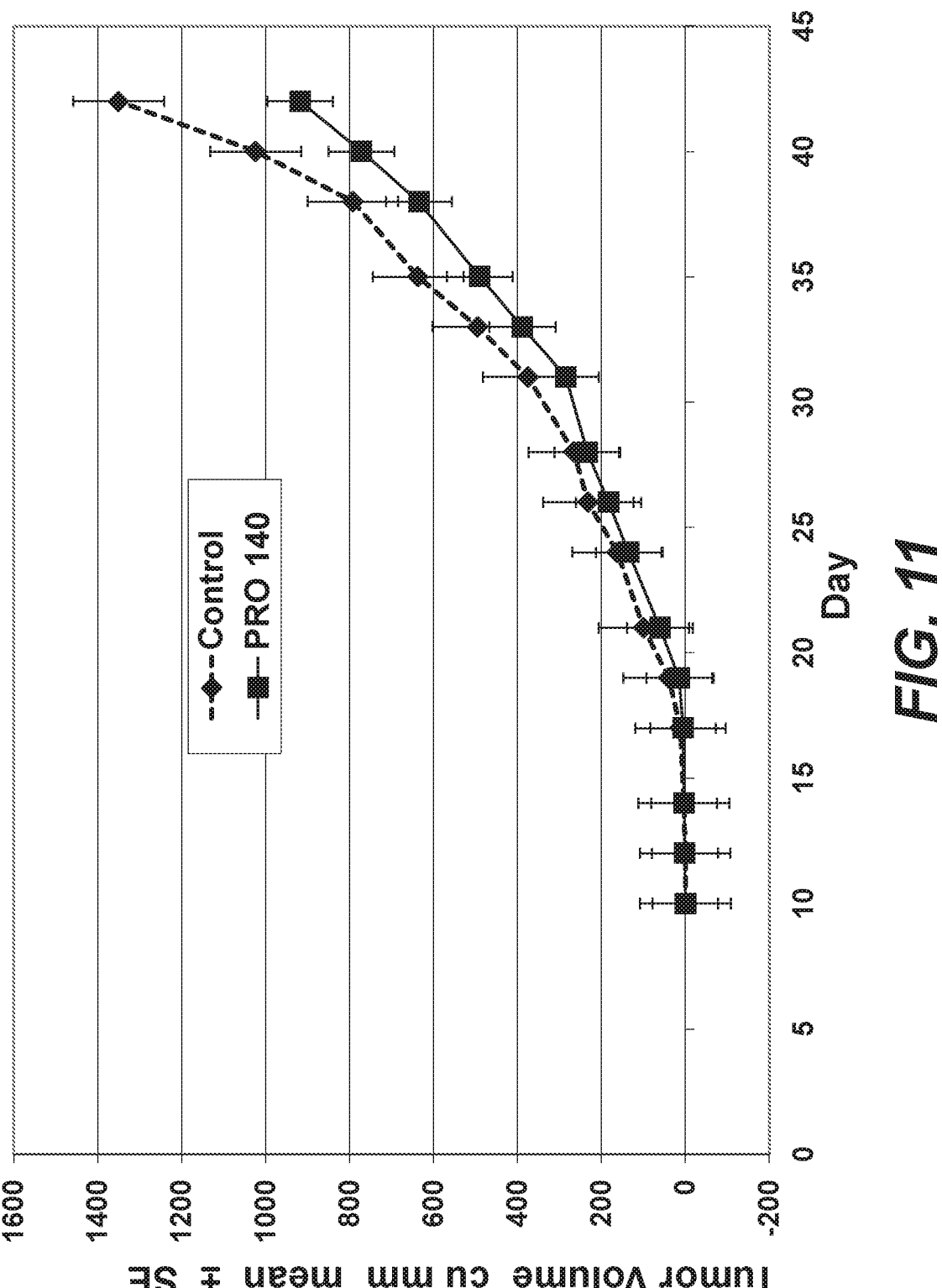

FIG. 11 shows tumor volume in male NSG mice inoculated with SW480 human colon carcinoma cells and then administered either 2 mg leronlimab or 2 mg non-specific control antibody (IgG) two times per week beginning on day 1 after inoculation. At 42 days post-inoculation, mean tumor volume did not significantly differ between the two groups. N=16 tumors/group; p=0.076.

Figure 12:
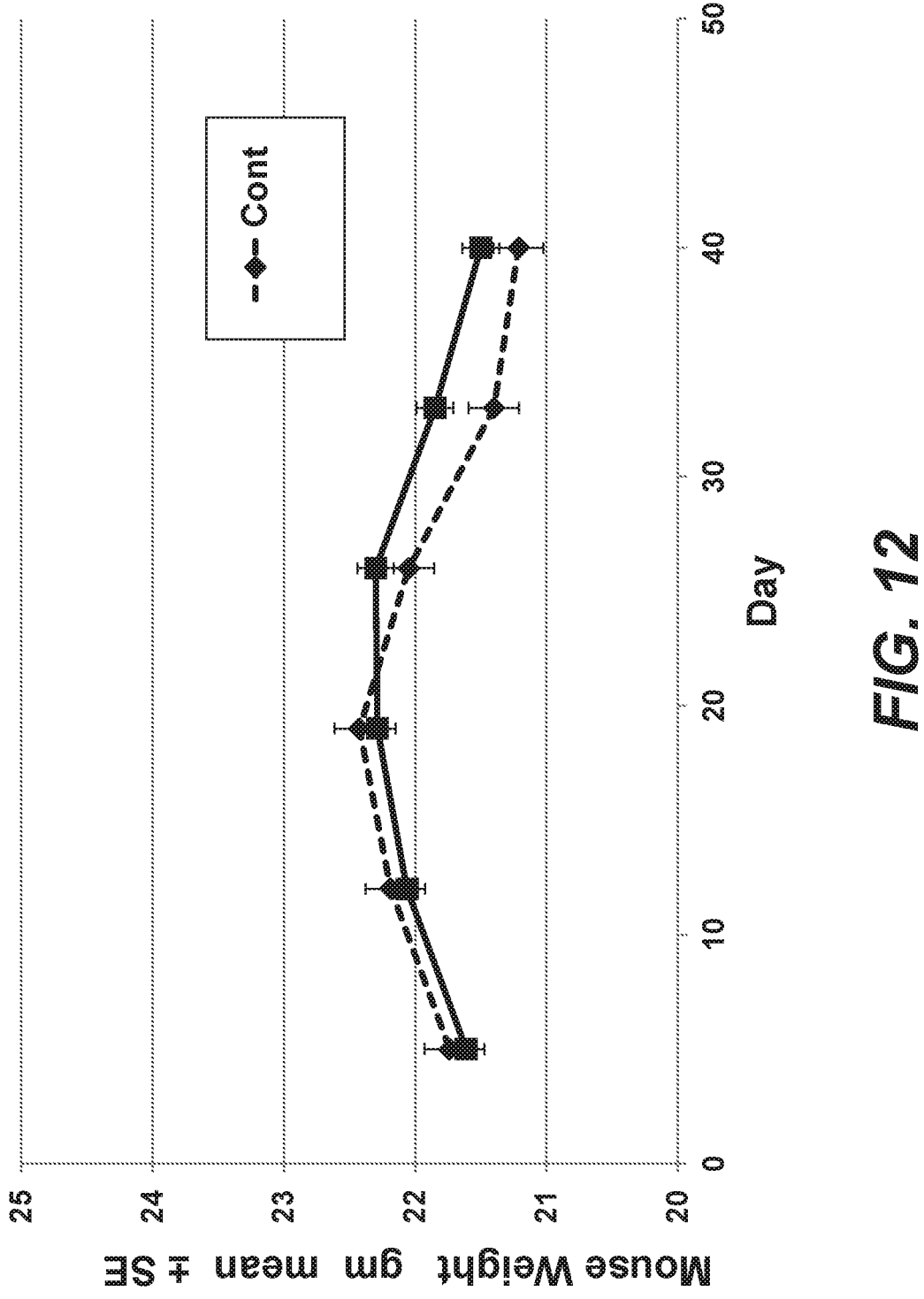

FIG. 12 shows mouse weight over the course of the study for male NSG mice inoculated with SW480 human colon carcinoma cells and then administered either 2 mg leronlimab or 2 mg non-specific control antibody (IgG) beginning on day 1 after inoculation. At 40 days post-inoculation, mean mouse weight did not significantly differ between the two groups. N=16 tumors/group; p=0.61.

Figure 13A:
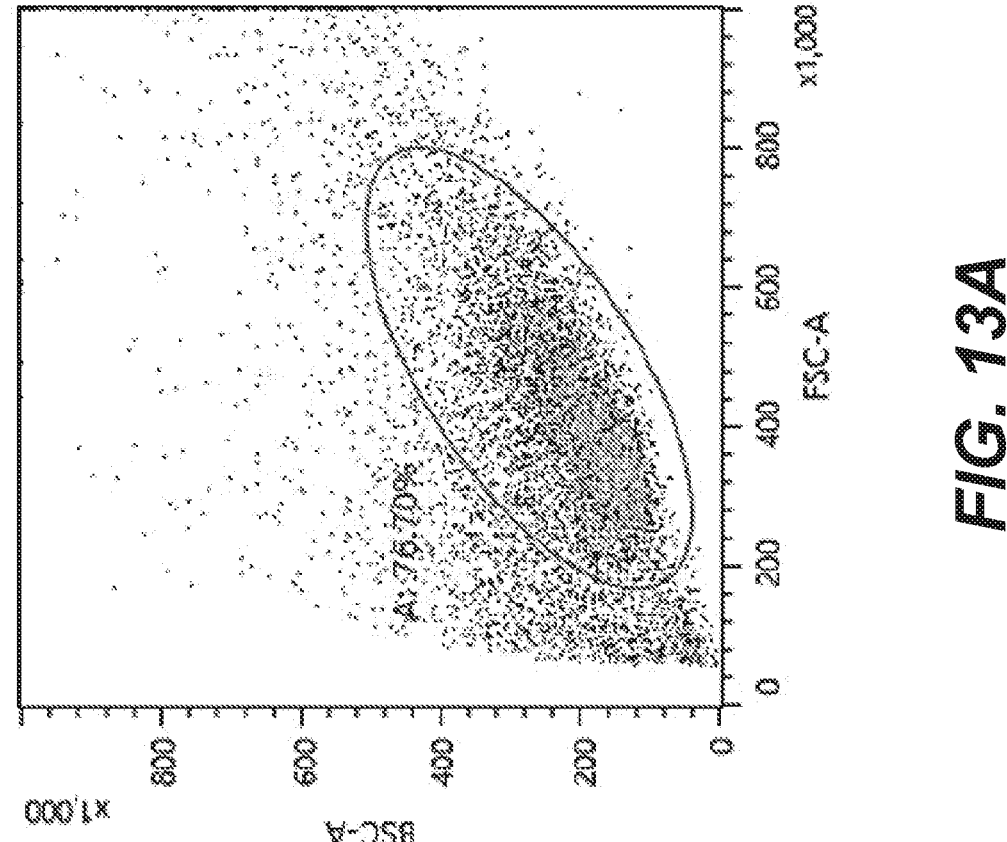
Figure 13B:
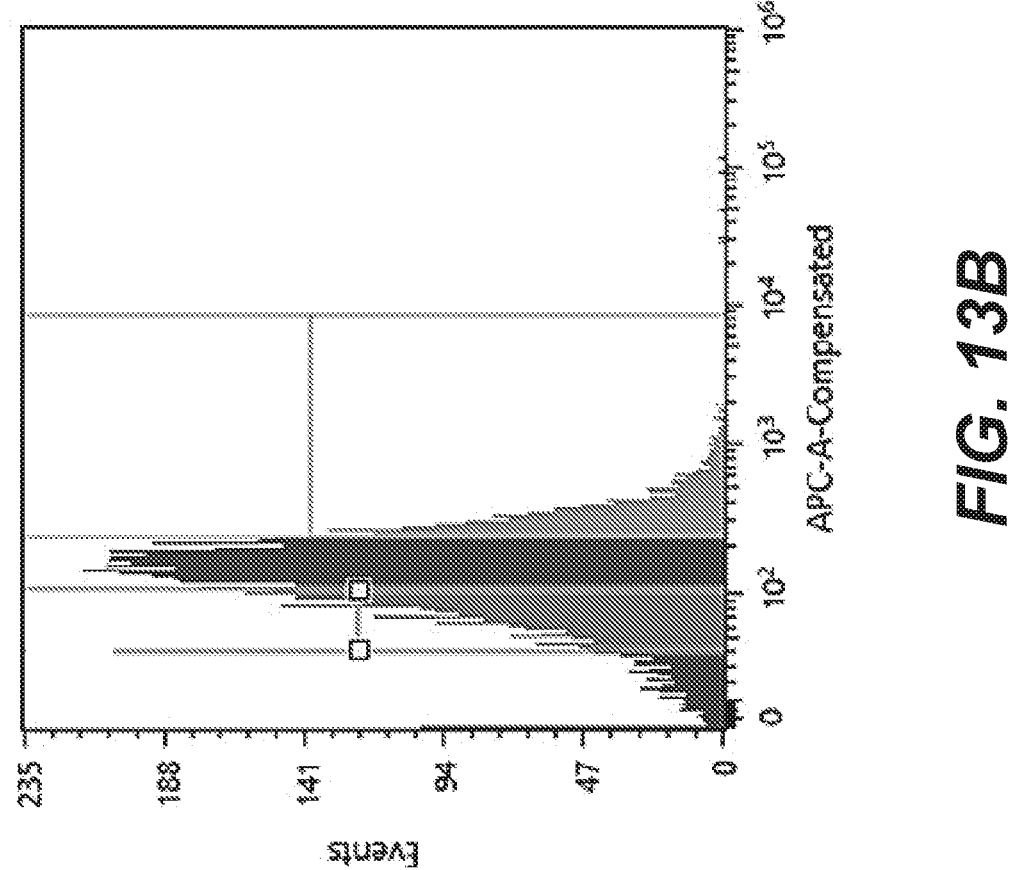
Figure 13C:
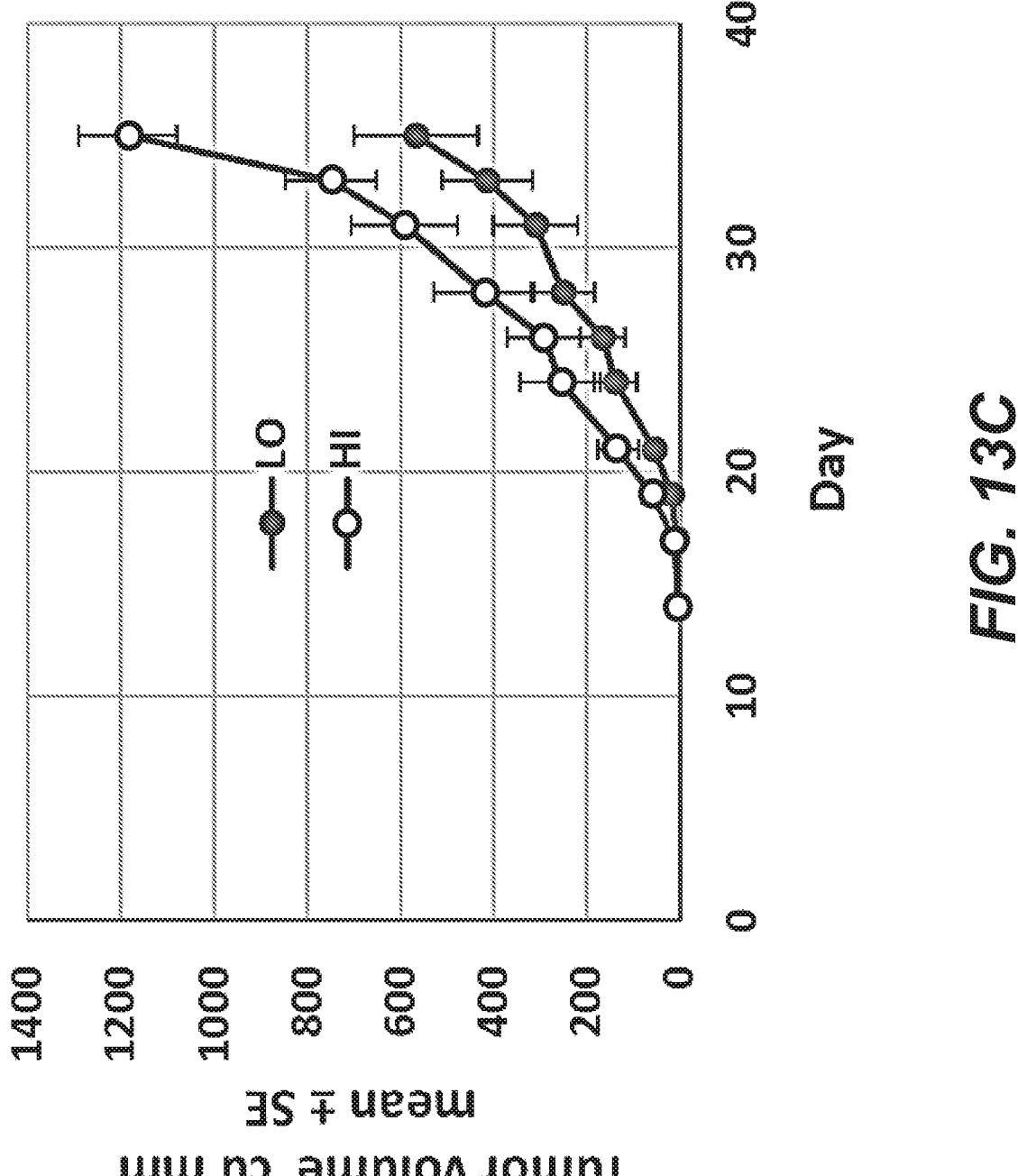

FIGS. 13A-13C depict the growth of CCR5-expressing FACS sorted SW480 colon carcinoma. FIG. 13A. Following gating (FSC vs. SSC) to exclude debris, 76.70% of cells were included in gate 1. FIG. 13B. Histogram of APC positive cells from gate 1, Interval gate between 101-102APC delineated the dim CCR5 positive cells, while the interval gate of 2.53-1.14 APC delineated the bright CCR5 positive cells. FIG. 13C. Sorted cells were inoculated into left flanks (dim, LO) and right flanks (bright, HI) of non-irradiated NSG mice ($2.5\times105$ cells per site). Hence each mouse bore 2 tumors and served as its own control. Basal growth rate is depicted; no treatment was given.

Figure 14A:
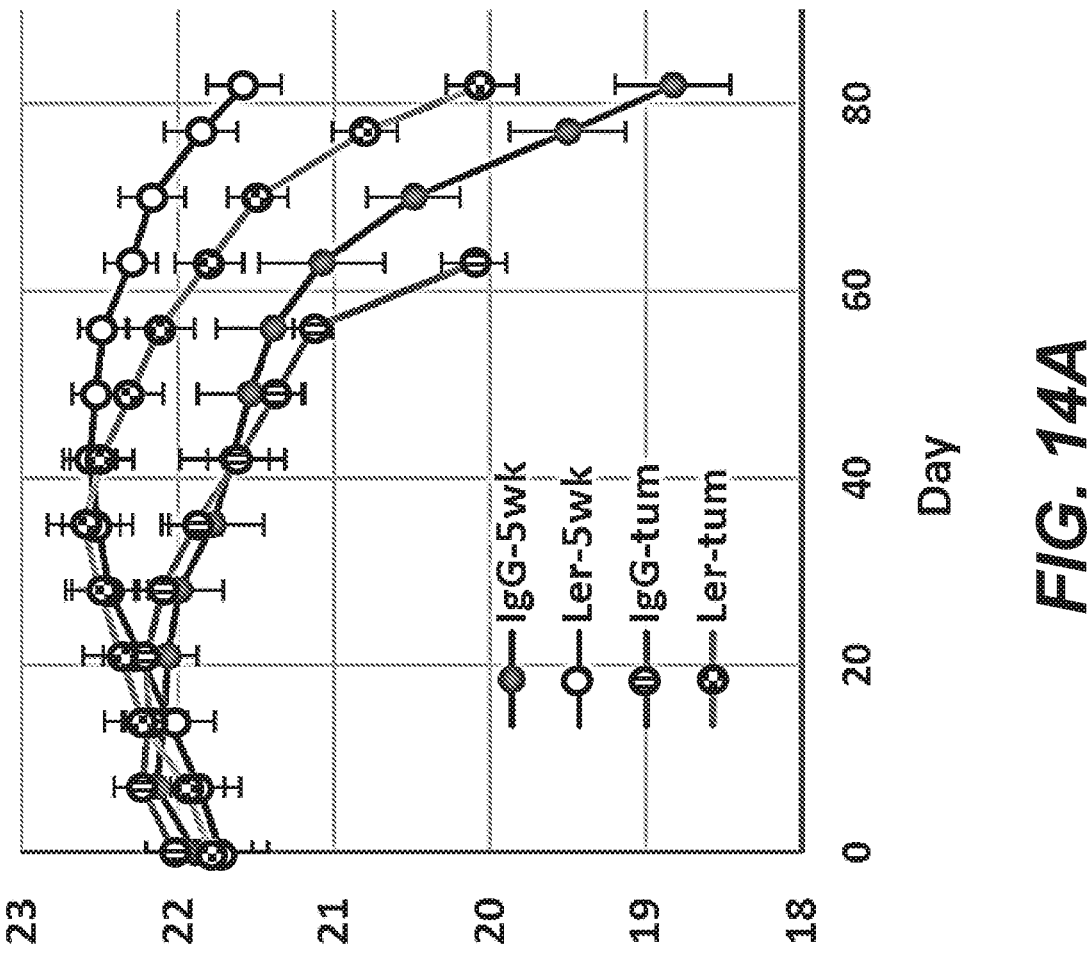
Figure 14B:
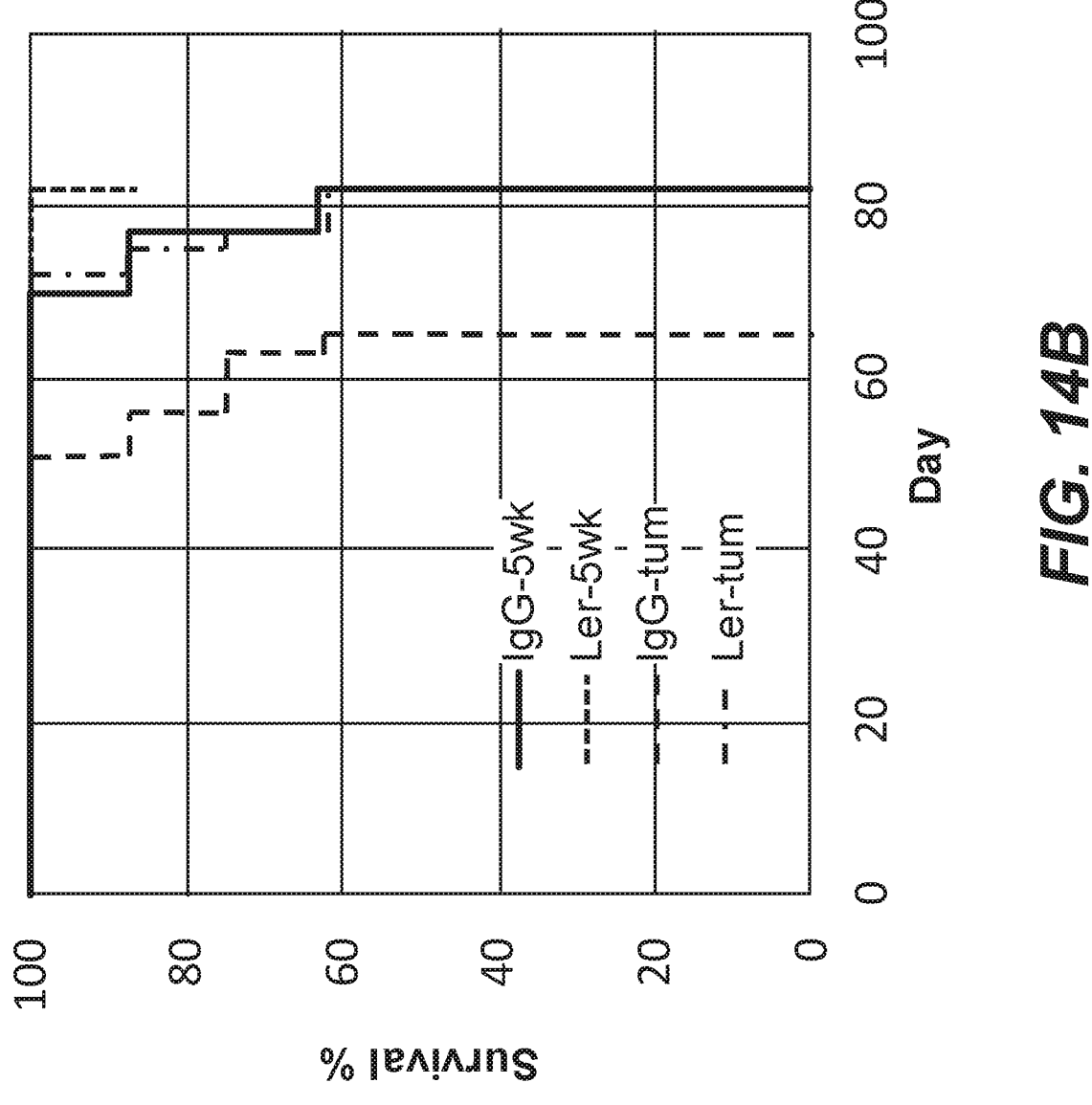

FIGS. 14A and 14B show that leronlimab delays xGVHD onset in humanized SW480 tumor-bearing mice. Sub-lethally irradiated NSG mice were inoculated on d0 with normal human BM (107 Ficoll-Hypaque purified mononuclear cells). FIG. 14A shows mean mouse weight. FIG. 14B shows % survival. Treatment groups: IgG-5 wk: IgG 2 mg i.p. 2×/wk for 35 day then stopped (non-tumor bearing), Ler-5 wk: Leronlimab 2 mg ip 2×/wk for 35 day then stopped (non-tumor bearing, IgG-tum: IgG 2 mg ip 2×/wk continuously, inoculated with SW480 ($2.5\times105$ cells s.c.) on day 35, Ler-tum: Leronlimab 2 mg ip 2×/wk continuously, inoculated with SW480 on day 35, n=8 mice/group.

Figure 15:
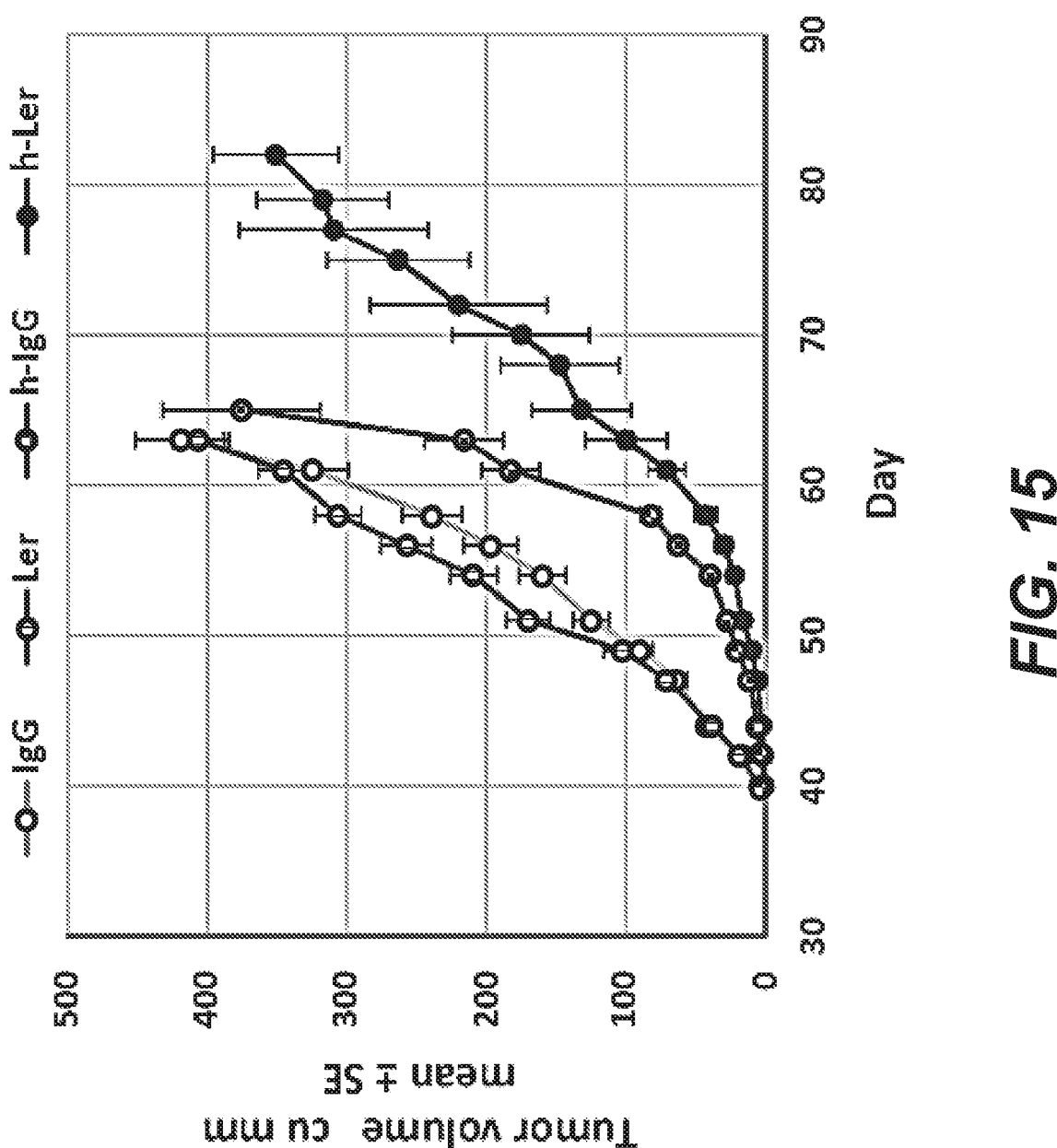

FIG. 15 shows the effect of mouse humanization on leronlimab anti-tumor activity. NSG mice were either humanized (normal human BM, 107 mononuclear cells) or sham injected, and then inoculated with SW480 ($2.5\times105$ cells s.c.) on day 35. Humanized mice received either IgG (h-IgG) or leronlimab (h-Ler). Nonhumanized mice received IgG (IgG) or leronlimab (Ler). All groups received 2 mg Ab i.p. twice weekly, starting day 7, n=8 mice/group.

Figure 16:
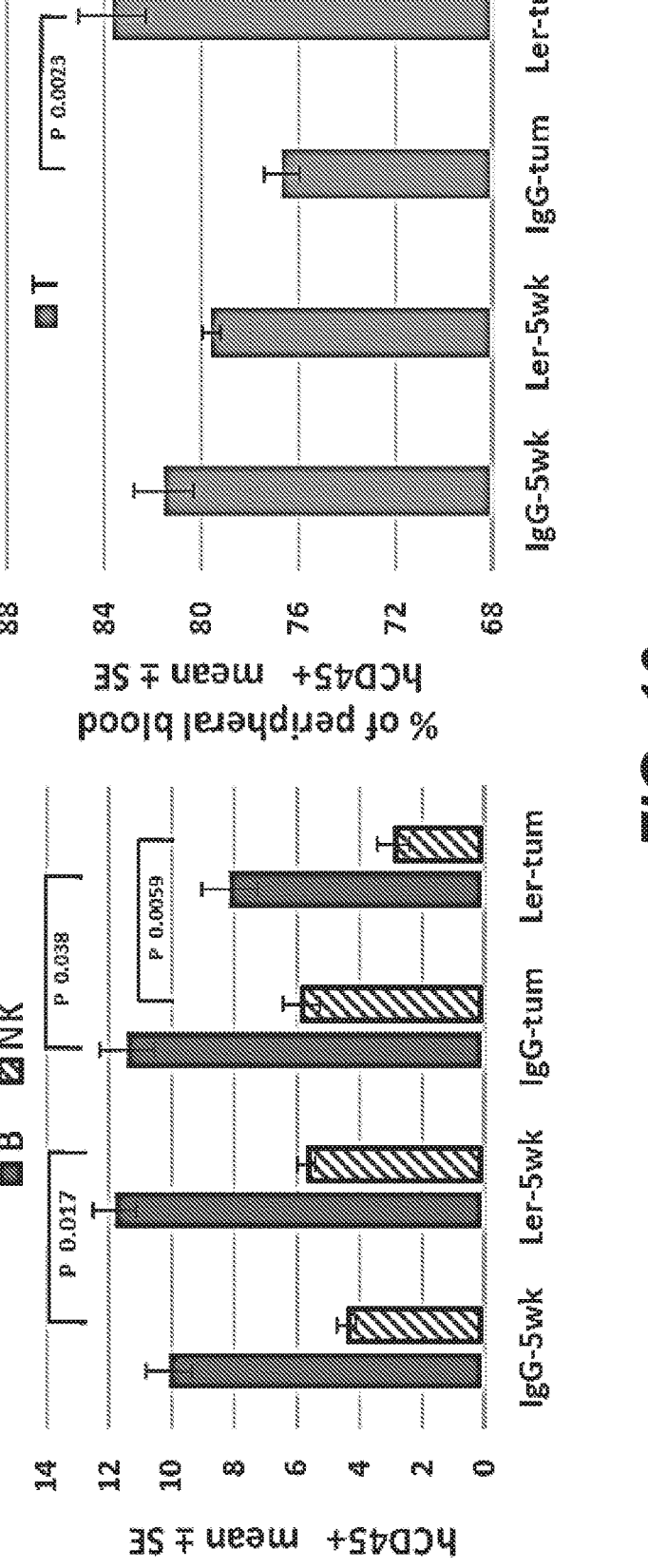

FIG. 16 shows the effect of leronlimab on peripheral blood B, T, and NK cells. Sub-lethally irradiated NSG mice were inoculated with normal human BM mononuclear cells. Treatment groups: IgG-5 wk: IgG 2 mg i.p. 2×/wk for 35 day then stopped (non-tumor bearing), Ler-5 wk: Leronlimab 2 mg ip 2×/wk for 35 day then stopped (non-tumor bearing), IgG-tum: IgG 2 mg ip 2×/wk continuously, inoculated with SW480 ($2.5\times105$ cells s.c.) on day 35, Ler-tum: Leronlimab 2 mg ip 2×/wk continuously, inoculated with SW480 on day 35, n=8 mice/group. Peripheral blood was analyzed on day 62 (gated on hCD45+). Significant p values are indicated.

Figure 17:
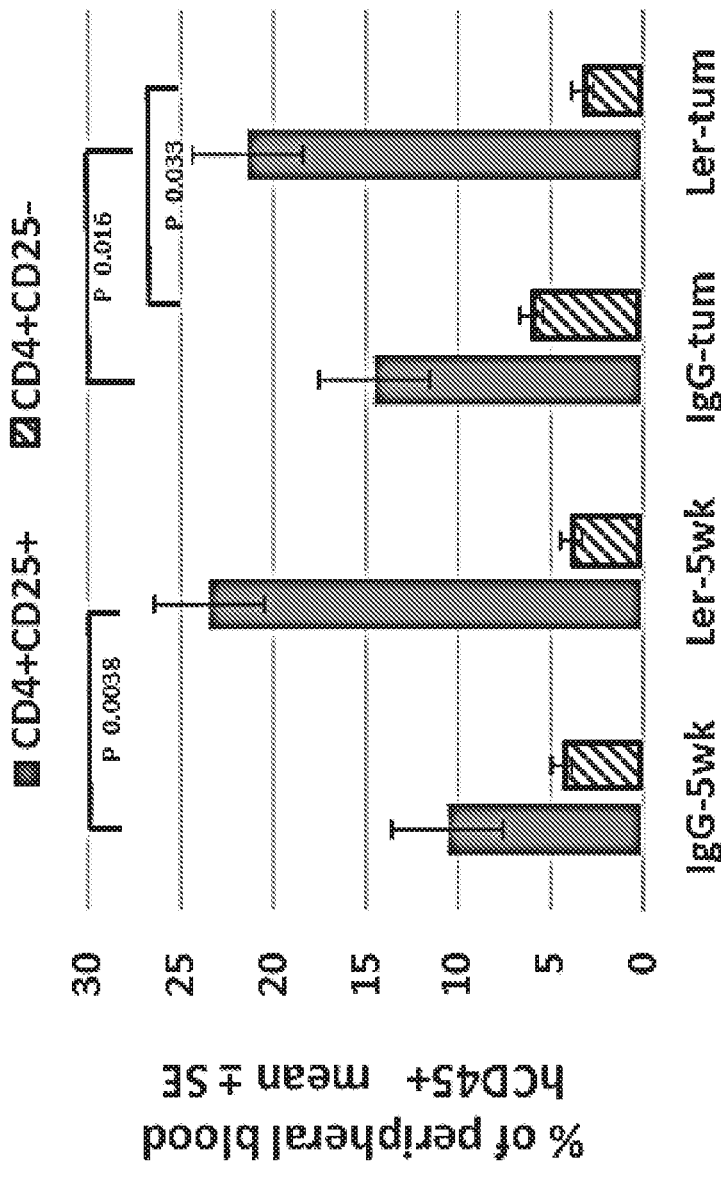

FIG. 17 shows the effect of leronlimab on peripheral blood Treg cells. Sub-lethally irradiated NSG mice were inoculated with normal human BM mononuclear cells. Treatment groups: IgG-5 wk: IgG 2 mg i.p. 2×/wk for 35 days then stopped (non-tumor bearing), Ler-5 wk: Leronlimab 2 mg ip 2×/wk for 35 days then stopped (non-tumor bearing, IgG-tum: IgG 2 mg ip 2×/wk continuously, inoculated with SW480 ($2.5\times105$ cells s.c.) on day 35, Ler-tum: Leronlimab 2 mg ip 2×/wk continuously, inoculated with SW480 on day 35, n=8 mice/group. Peripheral blood was analyzed on day 62 (gated on hCD45+). CD4+CD25+ cells suppress GVHD, whereas CD4+CD25− cells promote it. Significant p values are indicated.

Figure 18A:
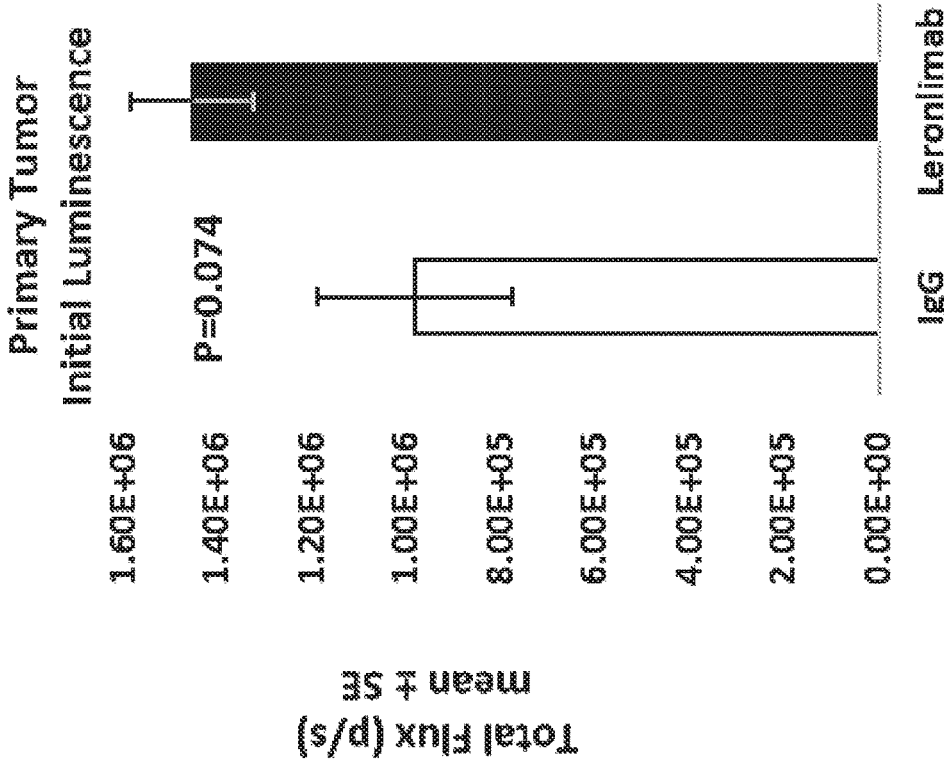
Figure 18A:
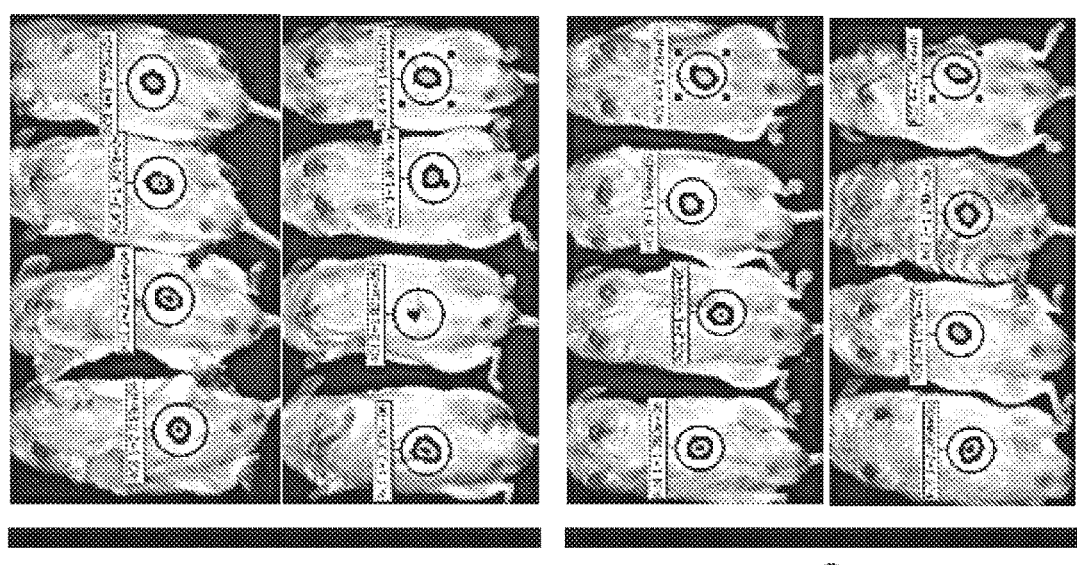
Figure 18B:
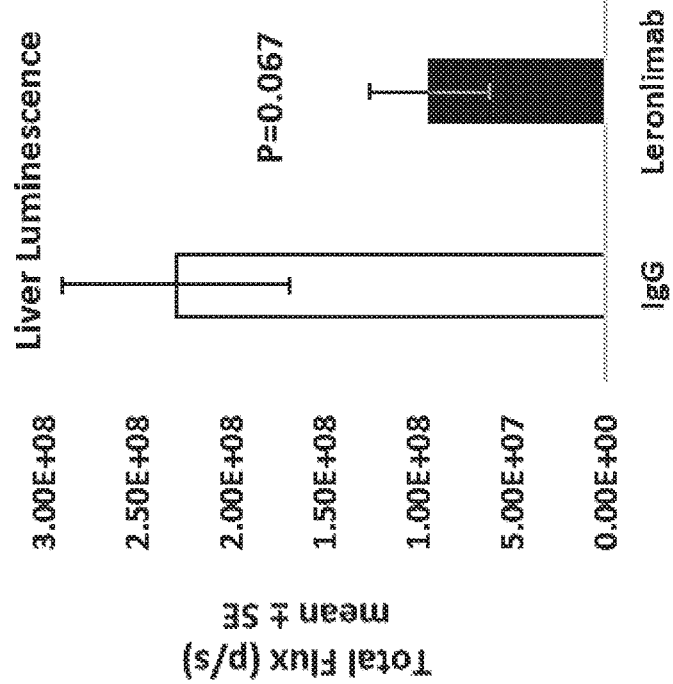
Figure 18B:
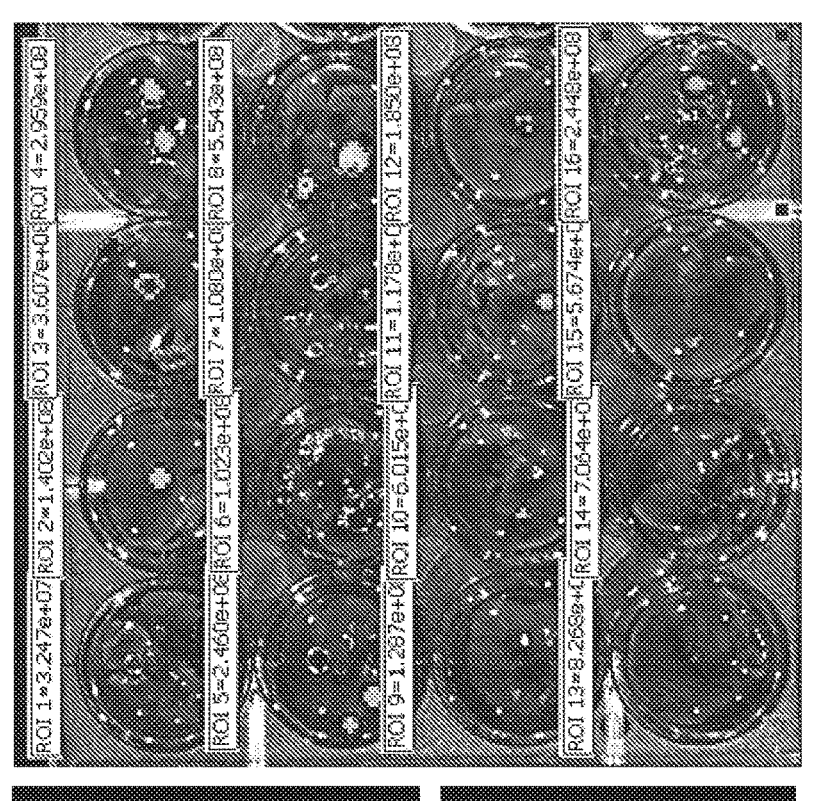
Figure 18C:
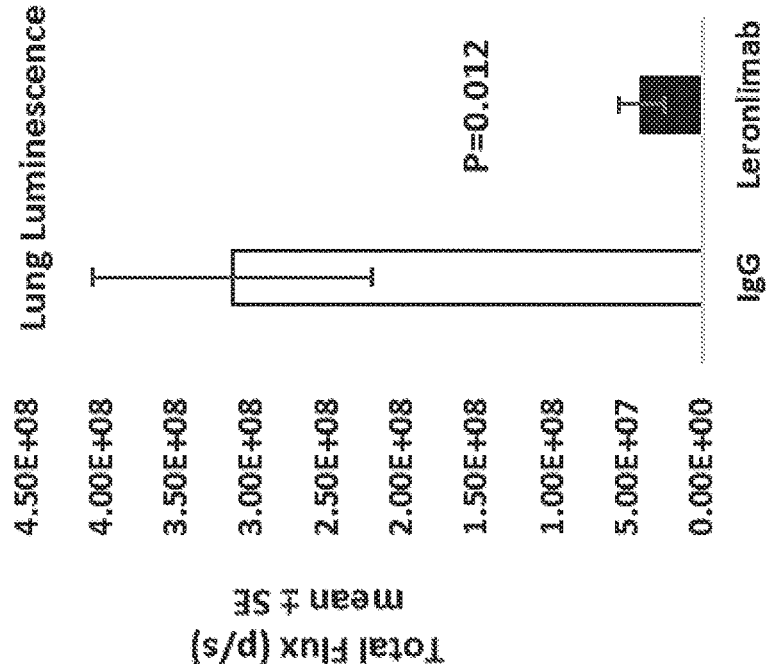
Figure 18C:
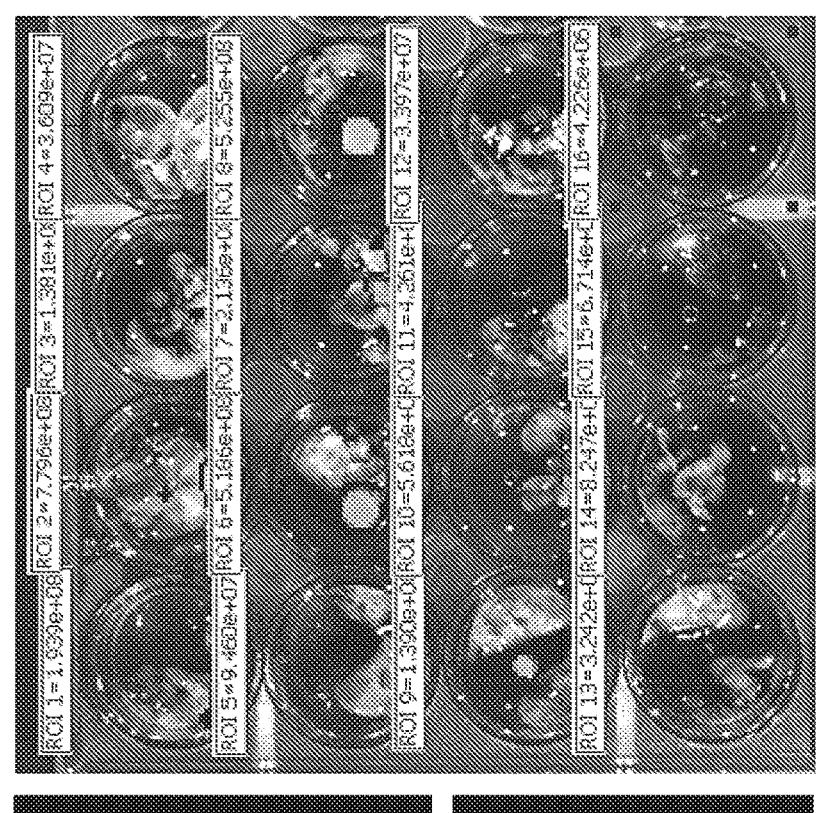

FIGS. 18A-18C show the effect of leronlimab on luc-SW480 colon carcinoma metastasis in vivo. SW480 cells were inoculated orthotopically in the cecum of humanized NSG mice. On day 10, IVIS imaging was performed to demonstrate comparable levels of engraftment in both treatment groups (FIG. 18A). Mice received continuous antibody treatment with 2 mg of either IgG or leronlimab administered intradermally 2×/wk. Following harvest on day 45, excised livers and lungs were incubated with luciferin substrate ex vivo. Leronlimab treatment resulted in decreased luminescence signal in livers (FIG. 18B) and in lungs (FIG. 18C).

Figure 19A:
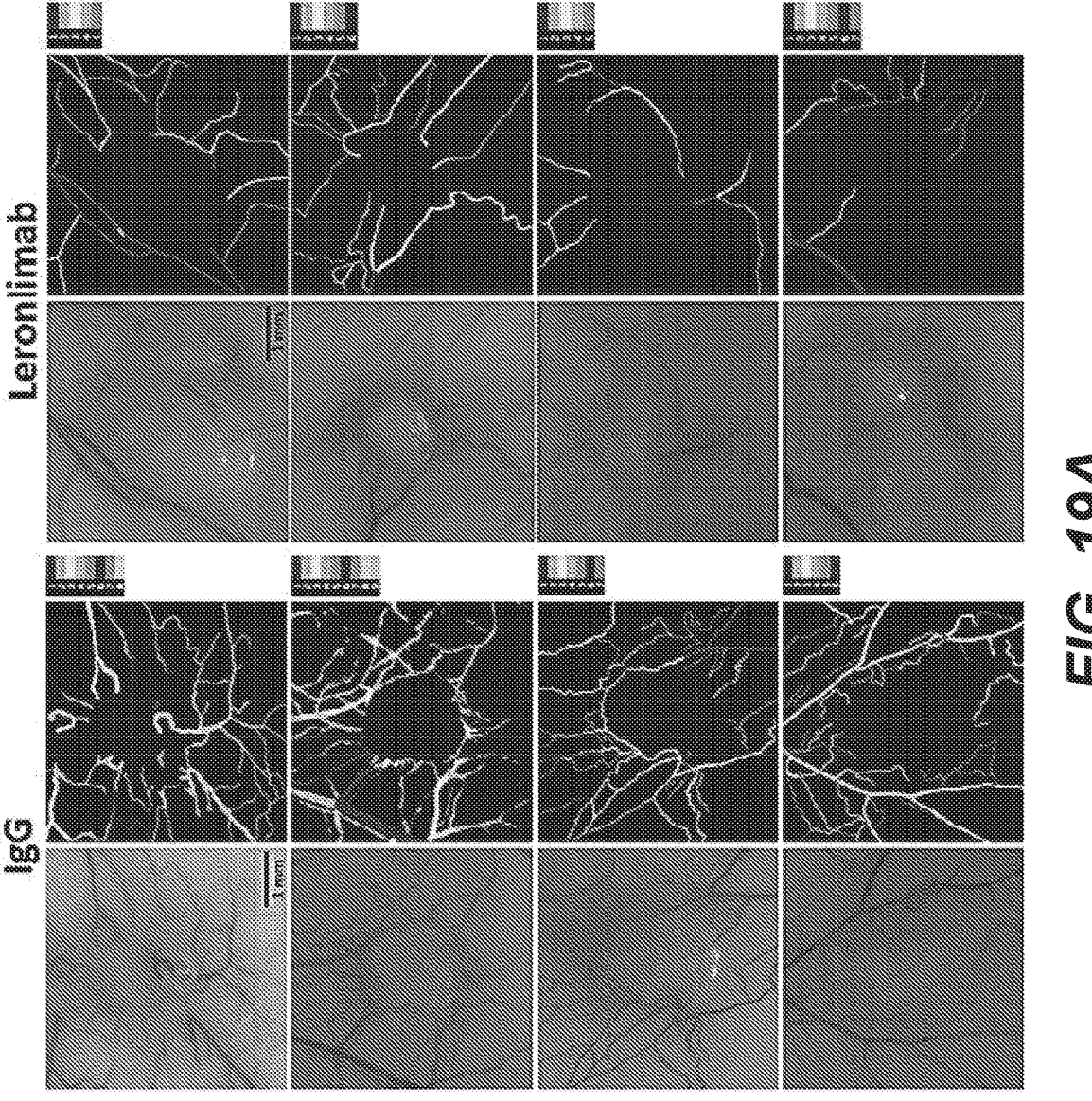
Figure 19B:
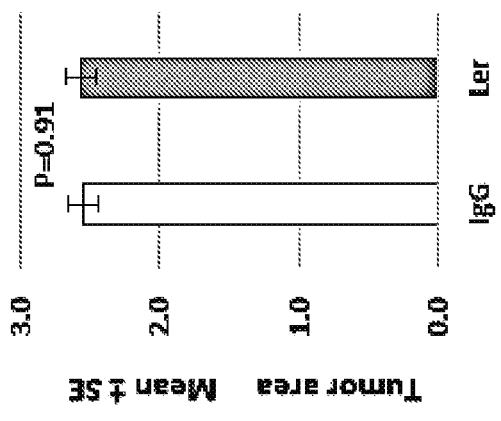
Figure 19B:
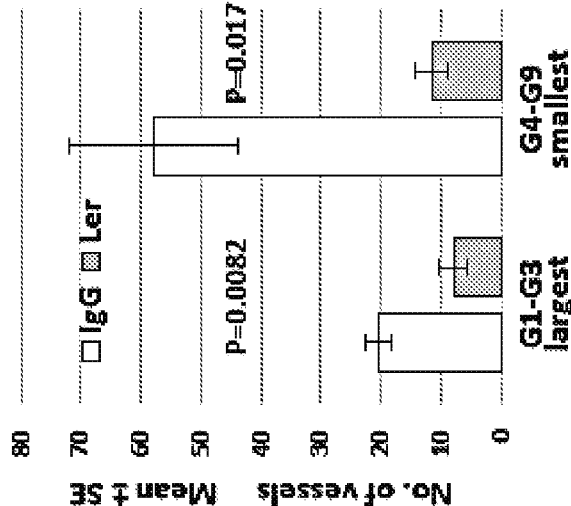
Figure 19B:
Figure 19B:
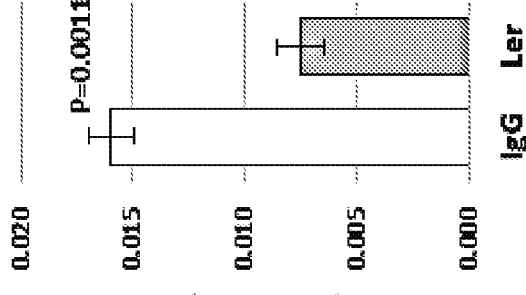
Figure 19B:
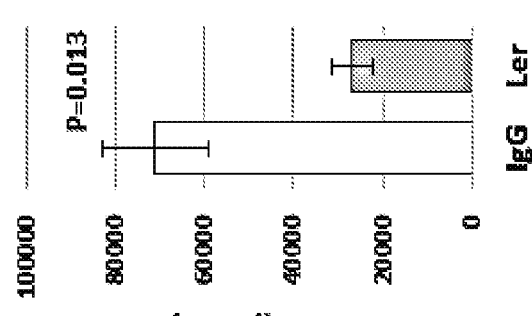

FIGS. 19A and 19B show a dermal angiogenesis assay. In order for a tumor to grow larger than 2 mm diameter, new host blood vessels must be induced. SW480 tumor cells ($2\times10^6$) were inoculated in suspension in a volume of 0.1 ml PBS into the dermis of humanized NSG mice. Mice were treated with 2 mg of either IgG or leronlimab administered intradermally 2×/wk. Ten days later, mice were euthanized and the inoculation site was photographed under 12.5× magnification. VESGEN software was used to analyze vessel number, diameter, branching, vessel generation number, and network characteristics. Assignment of vessels to branching generations G1-G9 by VESGEN. The VESGEN output image of a specimen here illustrates the classification of vessels into ten successively smaller branching generations (G1-G9) for the arterial end point region. Vessel branching generations are determined by (1) decrease in vessel diameter and (2) vessel bifurcations that are approximately symmetric (i.e., when diameters of offspring vessels branching from a parent vessel are approximately equal).

FIG. 19A shows the photomicrographs and vessel size analysis. FIG. 19B shows quantified data for total vessel area, vessel length density, number of vessels, and tumor area. Leronlimab-treated mice had over 2-fold reduction in neo vessel formation compared to IgG treated mice, evidenced by decrease in total pixel count, vessel length density, and overall number of vessels. Most dramatic was reduction of smaller vessels (Generation 4-9), as compared to larger vessels (Generation 1-3).

DETAILED DESCRIPTION

The instant disclosure provides methods for treating or preventing a cancer comprising administering a competitive inhibitor to a CCR5 cell receptor. In some embodiments, the competitive inhibitor comprises leronlimab, or a binding fragment thereof.

Glossary

Prior to setting forth this disclosure in more detail, it may be helpful to an understanding thereof to provide definitions of certain terms to be used herein. Unless defined otherwise, all technical and scientific terms used herein have the same meaning as is commonly understood by one of skill in the art to which this invention belongs. Additional definitions are set forth throughout this disclosure.

In the present description, any concentration range, percentage range, ratio range, or integer range is to be understood to include the value of any integer within the recited range and, when appropriate, fractions thereof (such as one tenth and one hundredth of an integer), unless otherwise indicated. Also, any number range recited herein relating to any physical feature, such as dose, are to be understood to include any integer within the recited range, unless otherwise indicated. As used herein, the term "about" means±20% of the indicated range, value, or structure, unless otherwise indicated.

It should be understood that the terms "a" and "an" as used herein refer to "one or more" of the enumerated components. The use of the alternative (e.g., "or") should be understood to mean either one, both, or any combination thereof of the alternatives.

As used herein, the terms "include," "have," and "comprise" are used synonymously, which terms and variants thereof are intended to be construed as non-limiting.

The term "consisting essentially of" limits the scope of a claim to the specified materials or steps, or to those that do not materially affect the basic characteristics of a claimed invention. For example, a protein domain, region, or module (e.g., a binding domain, hinge region, linker module) or a protein (which may have one or more domains, regions, or modules) "consists essentially of" a particular amino acid sequence when the amino acid sequence of a domain, region, or module or protein includes extensions, deletions, mutations, or any combination thereof (e.g., amino acids at the amino- or carboxy-terminus or between domains) that, in combination, contribute to at most 20% (e.g., at most 15%, 10%, 8%, 6%, 5%, 4%, 3%, 2% or 1%) of the length of a domain, region, or module or protein and do not substantially affect (i.e., do not reduce the activity by more than 50%, such as no more than 40%, 30%, 25%, 20%, 15%, 10%, 5% or 1%) the activity of the domain(s), region(s), module(s), or protein (e.g., the target binding affinity of a binding protein).

As used herein, "chemokine" means a cytokine that facilitates leukocyte movement. Chemokines may be characterized as either cys-cys or cys-X-cys depending on whether the two amino terminal cysteine residues are immediately adjacent or separated by one amino acid. It includes, but is not limited to, CCL5 (also known as RANTES), MIP-1α, MIP-1β, or SDF-1, etc. Chemokines exert their effects via binding to cell surface receptors.

As used herein, "chemokine receptor" means a member of a homologous family of seven-transmembrane spanning cell surface proteins that bind chemokines.

As used herein, "CCR5" is a chemokine receptor which binds members of the C-C group of chemokines and whose amino acid sequence comprises that provided in Genbank Accession Number 1705896, and related polymorphic variants.

As used herein, "antibody" means an immunoglobulin molecule comprising two heavy chains and two light chains and that recognizes an antigen. The immunoglobulin molecule may derive from any of the commonly known classes or isotypes, including but not limited to IgA, secretory IgA, IgG, and IgM. IgG subclasses are also well known to those in the art and include but are not limited to human IgG1, IgG2, IgG3, and IgG4. It includes, by way of example, both naturally occurring and non-naturally occurring antibodies. Specifically, "antibody" includes polyclonal and monoclonal antibodies, and monovalent and divalent fragments thereof. Furthermore, "antibody" includes chimeric antibodies, wholly synthetic antibodies, single chain antibodies, and fragments thereof. Optionally, an antibody can be labeled with a detectable marker. Detectable markers include, for example, radioactive or fluorescent markers. The antibody may be a human or nonhuman antibody. The nonhuman antibody may be humanized by recombinant methods to reduce its immunogenicity in humans. Methods for humanizing antibodies are known to those skilled in the art.

As used herein, "monoclonal antibody," also designated as "mAb," is used to describe antibody molecules whose primary sequences are essentially identical and which exhibit the same antigenic specificity. Monoclonal antibodies may be produced by hybridoma, recombinant, transgenic, or other techniques known to one skilled in the art.

As used herein, "heavy chain" means the larger polypeptide of an antibody molecule composed of one variable domain (VH) and three or four constant domains (CH1, CH2, CH3, and CH4), or fragments thereof.

As used herein, "light chain" means the smaller polypeptide of an antibody molecule composed of one variable domain (VL) and one constant domain (CL), or fragments thereof.

As used herein, a "binding fragment" or an "antigen-binding fragment or portion" of an antibody refers to the fragment or portion of an intact antibody that has or retains the ability to bind to the antigen target molecule recognized by the intact antibody, including fragment antigen binding (Fab) fragments, F(ab')2 fragments, Fab' fragments, Fv fragments, recombinant IgG (rIgG) fragments, single chain antibody fragments, including single chain variable fragments (scFv), and single domain antibodies (e.g., sdAb, sdFv, nanobody) fragments. The term encompasses genetically engineered or otherwise modified forms of immunoglobulins, such as intrabodies, peptibodies, chimeric antibodies, fully human antibodies, humanized antibodies, and heteroconjugate antibodies, multispecific, e.g., bispecific, antibodies, diabodies, triabodies, tetrabodies, tandem di-scFv, and tandem tri-scFv.

As used herein, "Fab" means a monovalent antigen binding fragment of an immunoglobulin that consists of one light chain and part of a heavy chain. It can be obtained by brief papain digestion or by recombinant methods.

As used herein, "F(ab')2 fragment" means a bivalent antigen binding fragment of an immunoglobulin that consists of both light chains and part of both heavy chains. It can be obtained by brief pepsin digestion or recombinant methods.

As used herein, "CDR" or "complementarity determining region" means a highly variable sequence of amino acids in the variable domain of an antibody. Numbering of CDR and framework regions may be determined according to any known method or scheme, such as the Kabat, Chothia, EU, IMGT, and AHo numbering schemes (see, e.g., Kabat et al., "Sequences of Proteins of Immunological Interest, US Dept. Health and Human Services, Public Health Service National Institutes of Health, 1991, 5th ed.; Chothia and Lesk, J. Mol. Biol. 196:901-917 (1987)); Lefranc et al., Dev. Comp. Immunol. 27:55, 2003; Honegger and Plückthun, J. Mol. Bio. 309:657-670 (2001)). Equivalent residue positions can be annotated and for different molecules to be compared using Antigen receptor Numbering And Receptor Classification (ANARCI) software tool (2016, Bioinformatics 15:298-300). Accordingly, identification of CDRs of an exemplary variable domain (VH or VL) sequence as provided herein according to one numbering scheme is not exclusive of an antibody comprising CDRs of the same variable domain as determined using a different numbering scheme.

As used herein, "humanized" describes antibodies wherein some, most or all of the amino acids outside the CDR regions are replaced with corresponding amino acids derived from human immunoglobulin molecules. In one embodiment of the humanized forms of the antibodies, some, most, or all of the amino acids outside the CDR regions have been replaced with amino acids from human immunoglobulin molecules but where some, most, or all amino acids within one or more CDR regions are unchanged. Small additions, deletions, insertions, substitutions, or modifications of amino acids are permissible as long as they would not abrogate the ability of the antibody to bind a given antigen. Suitable human immunoglobulin molecules would include IgG1, IgG2, IgG3, IgG4, IgA, and IgM molecules. A "humanized" antibody would retain a similar antigenic specificity as the original antibody, e.g., in the present disclosure, the ability to bind CCR5.

One skilled in the art would know how to make the humanized antibodies of the subject invention. Various publications, several of which are hereby incorporated by reference into this application, also describe how to make humanized antibodies. For example, the methods described in U.S. Pat. No. 4,816,567 comprise the production of chimeric antibodies having a variable region of one antibody and a constant region of another antibody. U.S. Pat. No. 5,225,539 describes another approach for the production of a humanized antibody. This patent describes the use of recombinant DNA technology to produce a humanized antibody wherein the CDRs of a variable region of one immunoglobulin are replaced with the CDRs from an immunoglobulin with a different specificity such that the humanized antibody would recognize the desired target but would not be recognized in a significant way by the human subject's immune system. Specifically, site directed mutagenesis is used to graft the CDRs onto the framework.

Other approaches for humanizing an antibody are described in U.S. Pat. Nos. 5,585,089 and 5,693,761 and WO 90/07861, which describe methods for producing humanized immunoglobulins. These have one or more CDRs and possible additional amino acids from a donor immunoglobulin and a framework region from an accepting human immunoglobulin. These patents describe a method to increase the affinity of an antibody for the desired antigen. Some amino acids in the framework are chosen to be the same as the amino acids at those positions in the donor rather than in the acceptor. Specifically, these patents describe the preparation of a humanized antibody that binds to a receptor by combining the CDRs of a mouse monoclonal antibody with human immunoglobulin framework and constant regions. Human framework regions can be chosen to maximize homology with the mouse sequence. A computer model can be used to identify amino acids in the framework region which are likely to interact with the CDRs or the specific antigen and then mouse amino acids can be used at these positions to create the humanized antibody.

The above U.S. Pat. Nos. 5,585,089 and 5,693,761 and WO 90/07861 also propose four possible criteria which may be used in designing the humanized antibodies. The first proposal was that for an acceptor, use a framework from a particular human immunoglobulin that is unusually homologous to the donor immunoglobulin to be humanized, or use a consensus framework from many human antibodies. The second proposal was that if an amino acid in the framework of the human immunoglobulin is unusual and the donor amino acid at that position is typical for human sequences, then the donor amino acid rather than the acceptor may be selected. The third proposal was that in the positions immediately adjacent to the 3 CDRs in the humanized immunoglobulin chain, the donor amino acid rather than the acceptor amino acid may be selected. The fourth proposal was to use the donor amino acid residue at the framework positions at which the amino acid is predicted to have a side chain atom within 3A of the CDRs in a three dimensional model of the antibody and is predicted to be capable of interacting with the CDRs. The above methods are merely illustrative of some of the methods that one skilled in the art could employ to make humanized antibodies. The affinity and/or specificity of the binding of the humanized antibody may be increased using methods of directed evolution as described in Wu et al., J. MOL. BIOL., 284:151 (1999) and U.S. Pat. Nos. 6,165,793; 6,365,408; and 6,413,774.

The variable regions of the humanized antibody may be linked to at least a portion of an immunoglobulin constant region of a human immunoglobulin. In one embodiment, the humanized antibody contains both light chain and heavy chain constant regions. The heavy chain constant region usually includes CH1, hinge, CH2, CH3, and, sometimes, CH4 region. In one embodiment, the constant regions of the humanized antibody are of the human IgG4 isotype.

The antibodies, or binding fragments, disclosed herein may either be labeled or unlabeled. Unlabeled antibodies can be used in combination with other labeled antibodies (second antibodies) that are reactive with a humanized antibody, such as antibodies specific for human immunoglobulin constant regions. Alternatively, the antibodies can be directly labeled. A wide variety of labels can be employed, such as radionuclides, fluors, enzymes, enzyme substrates, enzyme cofactors, enzyme inhibitors, ligands (particularly haptens), etc. Numerous types of immunoassays are available and are well known to those skilled in the art for detection of CCR5-expressing cells or detection of CCR5 modulation on cells capable of expressing CCR5.

The present disclosure also provides antibody or antibody fragment-polymer conjugates having an effective size or molecular weight that confers an increase in serum half-life, an increase in mean residence time in circulation (MRT), and/or a decrease in serum clearance rate over underivatized antibody fragments. Antibody fragment-polymer conjugates can be made by derivatizing the desired antibody fragment with an inert polymer. It will be appreciated that any inert polymer which provides the conjugate with the desired apparent size or which has the selected actual molecular weight is suitable for use in constructing antibody fragment-polymer conjugates of the invention.

Many inert polymers are suitable for use in pharmaceuticals. See, e.g., Davis et al., Biomedical Polymers: Polymeric Materials and Pharmaceuticals for Biomedical Use, pp. 441-451 (1980). For the antibody or antibody fragment-polymer conjugates disclosed herein, a non-protinaceous polymer is used. The nonprotinaceous polymer ordinarily is a hydrophilic synthetic polymer, i.e., a polymer not otherwise found in nature. However, polymers which exist in nature and are produced by recombinant or in vitro methods are also useful, as are polymers which are isolated from native sources. Hydrophilic polyvinyl polymers fall within the scope of this invention, e.g., polyvinyl alcohol and polyvinylpyrrolidone. Particularly useful are polyalkylene ethers such as polyethylene glycol (PEG); polyoxyalklyenes such as polyoxyethylene, polyoxypropylene, and block copolymers of polyoxyethylene and polyoxypropylene (Pluronics); polymethacrylates; carbomers; branched or unbranched polysaccharides which comprise the saccharide monomers D-mannose, D- and L-galactose, fucose, fructose, D-xylose, L-arabinose, D-glucuronic acid, sialic acid, D-galacturonic acid, D-mannuronic acid (e.g., polymannuronic acid, or alginic acid), D-glucosamine, D-galactosamine, D-glucose, and neuraminic acid including homopolysaccharides and heteropolysaccharides such as lactose, amylopectin, starch, hydroxyethyl starch, amylose, dextran sulfate, dextran, dextrins, glycogen, or the polysaccharide subunit of acid mucopolysaccharides, e.g., hyaluronic acid, polymers of sugar alcohols such as polysorbitol and polymannitol, heparin, or heparon. The polymer prior to cross-linking need not be, but preferably is, water soluble but the final conjugate must be water soluble. Preferably, the conjugate exhibits a water solubility of at least about 0.01 mg/ml and more preferably at least about 0.1 mg/ml, and still more preferably at least about 1 mg/ml. In one embodiment, the polymer should not be highly immunogenic in the conjugate form, nor should it possess viscosity that is incompatible with intravenous infusion or injection if the conjugate is intended to be administered by such routes.

In one embodiment, the polymer contains only a single group which is reactive. This helps to avoid cross-linking of protein molecules. However it is within the scope of the invention to maximize reaction conditions to reduce cross-linking, or to purify the reaction products through gel filtration or ion-exchange chromatography to recover substantially homogeneous derivatives. In other embodiments, the polymer contains two or more reactive groups for the purpose of linking multiple antibody fragments to the polymer backbone.

Gel filtration or ion-exchange chromatography can be used to recover the desired derivative in substantially homogeneous form.

The molecular weight of the polymer can range up to about 500,000 D and preferably is at least about 20,000 D, or at least about 30,000 D, or at least about 40,000 D. The molecular weight chosen can depend upon the effective size of the conjugate to be achieved, the nature (e.g., structure such as linear or branched) of the polymer and the degree of derivitization, i.e., the number of polymer molecules per antibody fragment, and the polymer attachment site or sites on the antibody fragment.

The polymer can be covalently linked to the antibody fragment through a multifunctional crosslinking agent which reacts with the polymer and one or more amino acid residues of the antibody fragment to be linked. However, it is also within the scope of the invention to directly crosslink the polymer by reacting a derivatized polymer with the antibody fragment, or vice versa.

The covalent crosslinking site on the antibody fragment includes the N-terminal amino group and epsilon amino groups found on lysine residues, as well other amino, imino, carboxyl, sulfhydryl, hydroxyl, or other hydrophilic groups. The polymer may be covalently bonded directly to the antibody fragment without the use of a multifunctional (ordinarily bifunctional) crosslinking agent, as described in U.S. Pat. No. 6,458,355.

The degree of substitution with such a polymer will vary depending upon the number of reactive sites on the antibody fragment, the molecular weight, hydrophilicity and other characteristics of the polymer, and the particular antibody fragment derivitization sites chosen. In general, the conjugate contains from 1 to about 10 polymer molecules, but greater numbers of polymer molecules attached to the antibody fragments of the invention are also contemplated. The desired amount of derivitization is easily achieved by using an experimental matrix in which the time, temperature, and other reaction conditions are varied to change the degree of substitution, after which the level of polymer substitution of the conjugates is determined by size exclusion chromatography or other means known in the art.

Functionalized PEG polymers to modify the antibody fragments of the invention are available from Shearwater Polymers, Inc. (Huntsville, Ala.). Such commercially available PEG derivatives include, but are not limited to, amino-PEG, PEG amino acid esters, PEG-hydrazide, PEG-thiol, PEG-succinate, carboxymethylated PEG, PEG-propionic acid, PEG amino acids, PEG succinimidyl succinate, PEG succinimidyl propionate, succinimidyl ester of carboxymethylated PEG, succinimidyl carbonate of PEG, succinimidyl esters of amino acid PEGs, PEG-oxycarbonylimidazole, PEG-nitrophenyl carbonate, PEG tresylate, PEG-glycidyl ether, PEG-aldehyde, PEG-vinylsulfone, PEG-maleim ide, PEG-orthopyridyl-disulfide, heterofunctional PEGs, PEG vinyl derivatives, PEG silanes, and PEG phospholides. The reaction conditions for coupling these PEG derivatives will vary depending on the protein, the desired degree of PEGylation, and the PEG derivative utilized. Some factors involved in the choice of PEG derivatives include: the desired point of attachment (such as lysine or cysteine R-groups), hydrolytic stability and reactivity of the derivatives, stability, toxicity and antigenicity of the linkage, suitability for analysis, etc. Specific instructions for the use of any particular derivative are available from the manufacturer. The conjugates of which may be separated from the unreacted starting materials by gel filtration or ion exchange HPLC.

As used herein, "anti-chemokine receptor antibody" means an antibody which recognizes and binds to an epitope on a chemokine receptor. As used herein, "anti-CCR5 antibody" means a monoclonal antibody that recognizes and binds to an epitope on the CCR5 chemokine receptor.

As used herein, "epitope" means a portion of a molecule or molecules that forms a surface for binding antibodies or other compounds. The epitope may comprise contiguous or noncontiguous amino acids, carbohydrate, or other nonpeptidyl moieties or oligomer-specific surfaces.

As used herein, "polypeptide" means two or more amino acids linked by a peptide bond.

A "nucleic acid molecule," or "polynucleotide," may be in the form of RNA or DNA, which includes cDNA, genomic DNA, and synthetic DNA. A nucleic acid molecule may be double stranded or single stranded, and if single stranded, may be the coding strand or non-coding (anti-sense strand). A coding molecule may have a coding sequence identical to a coding sequence known in the art or may have a different coding sequence, which, as the result of the redundancy or degeneracy of the genetic code, or by splicing, can encode the same polypeptide.

"Analogs" of antibodies or binding fragments include molecules differing from the antibodies or binding fragments by conservative amino acid substitutions. For purposes of classifying amino acid substitutions as conservative or non-conservative, amino acids may be grouped as follows: Group I (hydrophobic side chains): met, ala, val, leu, ile; Group II (neutral hydrophilic side chains): cys, ser, thr; Group III (acidic side chains): asp, glu; Group IV (basic side chains): asn, gln, his, lys, arg; Group V (residues influencing chain orientation): gly, pro; and Group VI (aromatic side chains): trp, tyr, phe. Conservative substitutions involve substitutions between amino acids in the same class. Non-conservative substitutions constitute exchanging a member of one of these classes for a member of another.

Due to the degeneracy of the genetic code, a variety of nucleic acid sequences encode the proteins or polypeptides disclosed herein. For example, homologous nucleic acid molecules may comprise a nucleotide sequence that is at least about 90% identical to a reference nucleotide sequence. More preferably, the nucleotide sequence is at least about 95% identical, at least about 97% identical, at least about 98% identical, or at least about 99% identical to a reference nucleotide sequence. The homology can be calculated using various, publicly available software tools well known to one of ordinary skill in the art. Exemplary tools include the BLAST system available from the website of the National Center for Biotechnology Information (NCBI) at the National Institutes of Health.

One method of identifying highly homologous nucleotide sequences is via nucleic acid hybridization. Thus, homologous nucleic acid molecules hybridize under high stringency conditions. Identification of related sequences can also be achieved using polymerase chain reaction (PCR) and other amplification techniques suitable for cloning related nucleic acid sequences. Preferably, PCR primers are selected to amplify portions of a nucleic acid sequence of interest, such as a CDR.

The term "high stringency conditions" as used herein refers to parameters with which the art is familiar. Nucleic acid hybridization parameters may be found in references that compile such methods, e.g., MOLECULAR CLONING: A LABORATORY MANUAL, J. Sambrook, et al., eds., Second Edition, Cold Spring Harbor Laboratory Press, Cold Spring Harbor, N.Y., (1989), or CURRENT PROTOCOLS IN MOLECULAR BIOLOGY, F. M. Ausubel, et al., eds., John Wiley & Sons, Inc., New York. One example of high stringency conditions is hybridization at 65 degrees Centigrade in hybridization buffer (3.5×SSC, 0.02% Ficoll, 0.02% polyvinyl pyrrolidone, 0.02% Bovine Serum Albumin, 2.5 mM NaH2PO4 (pII7), 0.5% SDS, 2 mM EDTA). SSC is 0.15M sodium chloride/0.015M sodium citrate, pH7; SDS is sodium dodecyl sulphate; and EDTA is ethylenediaminetetracetic acid. After hybridization, a membrane upon which the nucleic acid is transferred is washed, for example, in 2×SSC at room temperature and then at 0.1-0.5×SSC/0.1×SDS at temperatures up to 68 degrees Centigrade.

As used herein, the term "vector" refers to a nucleic acid molecule that is capable of transporting another nucleic acid. Vectors may be, for example, plasmids, cosmids, viruses, or phage. An "expression vector" is a vector that is capable of directing the expression of a protein encoded by one or more genes carried by the vector when it is present in the appropriate environment.

Nucleic acid sequences may be expressed in hosts after the sequences have been operably linked to (i.e., positioned to ensure the functioning of) an expression control sequence. These expression vectors are typically replicable in the host organisms, either as episomes or as an integral part of the host chromosomal DNA. Commonly, expression vectors will contain selection markers, e.g., tetracycline or neomycin, to permit detection of those cells transformed with the desired DNA sequences. See, e.g., U.S. Pat. No. 4,704,362, which is incorporated herein by reference.

E. coli is one prokaryotic host useful particularly for cloning the DNA sequences of the present invention. Other microbial hosts suitable for use include bacilli, such as Bacillus subtilus, and other enterobacteriaccae, such as Salmonella, Serratia, and various Pseudomonas species. In these prokaryotic hosts, one can also make expression vectors, which will typically contain expression control sequences compatible with the host cell (e.g., an origin of replication). In addition, any number of a variety of well-known promoters will be present, such as the lactose promoter system, a tryptophan (trp) promoter system, a beta-lactamase promoter system, or a promoter system from phage lambda. The promoters will typically control expression, optionally with an operator sequence, and have ribosome binding site sequences and the like, for initiating and completing transcription and translation.

Other microbes, such as yeast, may also be useful for expression. Saccharomyces is a preferred host, with suitable vectors having expression control sequences, such as promoters, including 3-phosphoglycerate kinase or other glycolytic enzymes and an origin of replication, termination sequences, and the like as desired.

In addition to microorganisms, mammalian tissue cell culture may also be used to express and produce the polypeptides of the present invention. See Winnacker, From Genes to Clones, VCH Publishers, New York, N.Y. (1987). Eukaryotic cells are actually preferred, because a number of suitable host cell lines capable of secreting intact immunoglobulins have been developed in the art, and include the CHO cell lines, various COS cell lines, HeLa cells, preferably myeloma cell lines, etc. and transformed B cells or hybridomas. Expression vectors for these cells can include expression control sequences, such as an origin of replication, a promoter, an enhancer (Queen et al., IMMUNOL. REV., 89: 49-68 (1986), which is incorporated herein by reference), and necessary processing information sites, such as ribosome binding sites, RNA splice sites, polyadenylation sites, and transcriptional terminator sequences. Preferred expression control sequences are promoters derived from immunoglobulin genes, SV40, Adenovirus, cytomegalovirus, Bovine Papilloma Virus, and the like.

The vectors containing the DNA segments of interest (e.g., the heavy and light chain encoding sequences and expression control sequences) can be transferred into the host cell by well-known methods, which vary depending on the type of cellular host. For example, calcium chloride transfection is commonly utilized for prokaryotic cells, whereas calcium phosphate treatment or electroporation may be used for other cellular hosts. See generally, Maniatis et al., MOLECULAR CLONING: A LABORATORY MANUAL, Cold Spring Harbor Press (1982), which is incorporated herein by reference.

Once expressed, the whole antibodies, their dimers, individual light and heavy chains, or other immunoglobulin forms or binding fragments of the present invention, can be purified according to standard procedures of the art, including ammonium sulfate precipitation, affinity columns, column chromatography, gel electrophoresis, and the like. See generally, R. Scopes, PROTEIN PURIFICATION, Springer-Verlag, New York (1982). Substantially pure immunoglobulins of at least about 90 to 95% homogeneity are preferred, and 98 to 99% or more homogeneity most preferred, for pharmaceutical uses. Once purified, partially or to homogeneity as desired, the polypeptides may then be used therapeutically (including extracorporeally) or in developing and performing assay procedures, immunofluorescent stainings, and the like. See generally, IMMUNOLOGICAL METHODS, Vols. I and II, Lefkovits and Pernis, eds., Academic Press, New York, N.Y. (1979 and 1981).

As used herein, "inhibits" means that the amount is reduced in the presence of a composition as compared with the amount that would occur without the composition.

The term "competitive inhibitor" as used herein refers to a molecule that competes with a reference molecule for binding to a target, and thereby blunts, inhibits, dampens, reduces, or blocks the effects of the reference molecule on the target. For example, leronlimab is a competitive inhibitor of CCL5 binding to CCR5 receptor.

"Agonist activity" as used in the present disclosure refers to the binding by a molecule to a target, wherein the binding activates the target to produce a response.

"CCL5 agonist activity," as used herein, refers to activity consistent with activation by CCL5.

"Antagonist activity" as used in the present disclosure refers to the binding by a molecule to a target, wherein the binding does not activate the target to produce a response and the binding blocks the action of one or more agonist molecules.

As used herein, "subject" means any animal or artificially modified animal capable of having cancer. Artificially modified animals include, but are not limited to, SCID mice with human immune systems. The animals include but are not limited to mice, rats, dogs, guinea pigs, ferrets, rabbits, and primates. In a preferred embodiment, the subject is a human.

As used herein, "treating" means inhibiting, slowing, stopping, or reversing the progression of a given disease or disorder. In a preferred embodiment, "treating" means reversing the progression of the disease or disorder. In some embodiments, treating includes reversing the progression of the disease or disorder to the point of eliminating the disease or disorder.

As used herein, "preventing" refers to preventing a disease or disorder from occurring; delaying the onset or progression of a disease or disorder; or reducing the pathology or symptomatology of a disease or disorder. For example, preventing a cancer includes preventing the development of a tumor, slowing the growth of a tumor, and delaying the development of a tumor.

As used herein, "administering" may be effected or performed using any of the methods known to one skilled in the art. The methods may comprise intravenous, intramuscular, or subcutaneous means.

As used herein, "effective dose" means an amount in sufficient quantities to either treat the subject or prevent the subject from developing cancer. A person of ordinary skill in the art can perform simple titration experiments to determine what amount is required to treat the subject.

CCR5 Antagonists

In one aspect, the present disclosure relates to the use of CCR5 antagonists that target CCR5 receptor, and act as competitive inhibitors to the CCR5 cell receptor without providing CCL5 agonist activity.

In one embodiment, the present disclosure provides for the use of a leronlimab antibody, or binding fragment thereof, in treating or preventing cancer. Leronlimab (also referred to herein as PRO 140) is a humanized monoclonal antibody described in U.S. Pat. Nos. 7,122,185 and 8,821,877, which are incorporated herein by reference, in their entirety. Leronlimab is a humanized version of the murine mAb, PA14, which was generated against CD4+ CCR5+ cells. Olson et al., *Differential Inhibition of Human Immunodeficiency Virus Type* 1 *Fusion, gp* 120 *Binding and CC-Chemokine Activity of Monoclonal Antibodies to CCR5*, J. VIROL., 73: 4145-4155. (1999). Leronlimab binds to CCR5 expressed on the surface of a cell, and potently inhibits HIV-1 entry and replication at concentrations that do not affect CCR5 chemokine receptor activity in vitro and in the hu-PBL-SCID mouse model of HIV-1 infection. Olson et al., *Differential Inhibition of Human Immunodeficiency Virus Type* 1 *Fusion, gp* 120 *Binding and CC-Chemokine Activity of Monoclonal Antibodies to CCR5*, J. VIROL., 73: 4145-4155. (1999); Trkola et al., *Potent, Broad-Spectrum Inhibition of Human Immunodeficiency Virus Type* 1 *by the CCR5 Monoclonal Antibody PRO* 140, J. VIROL., 75: 579-588 (2001).

Nucleic acids encoding heavy and light chains of the humanized leronlimab antibody have been deposited with the ATCC. Specifically, the plasmids designated pVK-HuPRO140, pVg4-HuPRO140 (mut B+D+I) and pVg4-HuPRO140 HG2, respectively, were deposited pursuant to, and in satisfaction of, the requirements of the Budapest Treaty with the ATCC, Manassas, Va., U.S.A. 20108, on Feb. 22, 2002, under ATCC Accession Nos. PTA 4097, PTA 4099, and PTA 4098, respectively. The plasmids designated pVK-HuPRO140 and pVg4-HuPRO140 HG2 encode the light chain and heavy chain, respectively, of leronlimab.

The HCDR1-3 and LCDR1-3 amino acid sequences of leronlimab are set forth in SEQ ID NOS:12-14 and 9-11, respectively. The VH and VL sequences of leronlimab are set forth in amino acids 20-141 of SEQ ID NO:3 and amino acids 20-131 of SEQ ID NO:1, respectively. The heavy chain and light chain sequences of leronlimab are set forth in SEQ ID NOS:7 and 8, respectively.

In a one embodiment, the methods disclosed herein comprise administering a humanized antibody designated leronlimab or an antibody that competes with leronlimab for binding to the CCR5 receptor, wherein the leronlimab comprises (i) two light chains, each light chain comprising the expression product of the plasmid designated pVK: HuPRO140-VK (ATCC Deposit Designation PTA-4097), and (ii) two heavy chains, each heavy chain comprising the expression product of either the plasmid designated pVg4: HuPRO140 HG2-VH (ATCC Deposit Designation PTA-4098) or the plasmid designated pVg4:HuPRO140 (mut B+D+I)-VH (ATCC Deposit Designation PTA-4099). In a further embodiment, the leronlimab is a humanized or human antibody that binds to the same epitope as that to which antibody leronlimab binds. In another embodiment, the monoclonal antibody is the humanized antibody designated leronlimab.

In some embodiments, the present disclosure provides use of an anti-CCR5 antibody or antigen binding fragment thereof having a light chain variable region (VL) that is at least 70% identical to SEQ ID NO: 1, at least 75% identical to SEQ ID NO: 1, at least 80% identical to SEQ ID NO: 1, at least 85% identical to SEQ ID NO: 1, at least 90% identical to SEQ ID NO: 1, or at least 95% identical to SEQ ID NO: 1. In some embodiments, the present disclosure provides use of an anti-CCR5 antibody or antigen binding fragment thereof having a light chain variable antibody region that is 70%-100% identical to SEQ ID NO: 1, 75%-100% identical to SEQ ID NO: 1, 80%-100% identical to SEQ ID NO: 1, 85%-100% identical to SEQ ID NO: 1, 90%-100% identical to SEQ ID NO: 1, 91%-100% identical to SEQ ID NO: 1, or 95%-100% identical to SEQ ID NO: 1.

In some embodiments, the present disclosure provides use of an anti-CCR5 antibody or antigen binding fragment thereof having a light chain variable region (VL) that is at least 70% identical to amino acids 20-131 of SEQ ID NO: 1, at least 75% identical to amino acids 20-131 of SEQ ID NO: 1, at least 80% identical to amino acids 20-131 of SEQ ID NO: 1, at least 85% identical to amino acids 20-131 of SEQ ID NO: 1, at least 90% identical to amino acids 20-131 of SEQ ID NO: 1, or at least 95% identical to amino acids 20-131 of SEQ ID NO: 1. In some embodiments, the present disclosure provides use of an anti-CCR5 antibody or antigen binding fragment thereof having a light chain variable antibody region that is 70%-100% identical to amino acids 20-131 of SEQ ID NO: 1, 75%-100% identical to amino acids 20-131 of SEQ ID NO: 1, 80%-100% identical to amino acids 20-131 of SEQ ID NO: 1, 85%-100% identical to amino acids 20-131 of SEQ ID NO: 1, 90%-100% identical to amino acids 20-131 of SEQ ID NO: 1, 91%-100% identical to amino acids 20-131 of SEQ ID NO: 1, or 95%-100% identical to amino acids 20-131 of SEQ ID NO: 1.

In some embodiments, the present disclosure provides use of an anti-CCR5 antibody or antigen binding fragment thereof having a heavy chain variable region (VH) that is at least 70% identical to SEQ ID NO:3, at least 75% identical to SEQ ID NO:3, at least 80% identical to SEQ ID NO:3, at least 85% identical to SEQ ID NO:3, at least 90% identical to SEQ ID NO:3, or at least 95% identical to SEQ ID NO:3. In some embodiments the present disclosure provides use of an anti-CCR5 antibody or antigen binding fragment thereof having a heavy chain antibody variable region that is 70%-100% identical to SEQ ID NO: 3, 75%-100% identical to SEQ ID NO: 3, 80%-100% identical to SEQ ID NO: 3, 85%-100% identical to SEQ ID NO: 3, 90%-100% identical to SEQ ID NO: 3, 91%-100% identical to SEQ ID NO:3, or 95%-100% identical to SEQ ID NO:3.

In some embodiments, the present disclosure provides use of an anti-CCR5 antibody or antigen binding fragment thereof having a heavy chain variable region (VH) that is at least 70% identical to amino acids 20-141 of SEQ ID NO:3, at least 75% identical to amino acids 20-141 of SEQ ID NO:3, at least 80% identical to amino acids 20-141 of SEQ ID NO:3, at least 85% identical to amino acids 20-141 of SEQ ID NO:3, at least 90% identical to amino acids 20-141 of SEQ ID NO:3, or at least 95% identical to amino acids 20-141 of SEQ ID NO:3. In some embodiments the present disclosure provides use of an anti-CCR5 antibody or antigen binding fragment thereof having a heavy chain antibody variable region that is 70%-100% identical to amino acids 20-141 of SEQ ID NO: 3, 75%-100% identical to amino acids 20-141 of SEQ ID NO: 3, 80%-100% identical to amino acids 20-141 of SEQ ID NO: 3, 85%-100% identical to amino acids 20-141 of SEQ ID NO: 3, 90%-100% identical to amino acids 20-141 of SEQ ID NO: 3, 91%-100% identical to amino acids 20-141 of SEQ ID NO:3, or 95%-100% identical to amino acids 20-141 of SEQ ID NO:3.

In some embodiments, the present disclosure provides use of an anti-CCR5 antibody having a heavy chain variable region (VH) that is at least 70% identical to SEQ ID NO:5, at least 75% identical to SEQ ID NO: 5, at least 80% identical to SEQ ID NO: 5, at least 85% identical to SEQ ID NO: 5, at least 90% identical to SEQ ID NO: 5, or at least 95% identical to SEQ ID NO: 5. In some embodiments the present disclosure provides use of an anti-CCR5 antibody having a heavy chain variable antibody region that is 70%-100% identical to SEQ ID NO: 5, 75%-100% identical to SEQ ID NO: 5, 80%-100% identical to SEQ ID NO: 5, 85%-100% identical to SEQ ID NO: 5, 90%-100% identical to SEQ ID NO: 5, 91%-100% identical to SEQ ID NO: 5, or 95%-100% identical to SEQ ID NO: 5.

In some embodiments, the present disclosure provides use of an anti-CCR5 antibody having a heavy chain variable region (VH) that is at least 70% identical to amino acids 20-141 of SEQ ID NO:5, at least 75% identical to amino acids 20-141 of SEQ ID NO: 5, at least 80% identical to amino acids 20-141 of SEQ ID NO: 5, at least 85% identical to amino acids 20-141 of SEQ ID NO: 5, at least 90% identical to amino acids 20-141 of SEQ ID NO: 5, or at least 95% identical to amino acids 20-141 of SEQ ID NO: 5. In some embodiments the present disclosure provides use of an anti-CCR5 antibody having a heavy chain variable antibody region that is 70%-100% identical to amino acids 20-141 of SEQ ID NO: 5, 75%-100% identical to amino acids 20-141 of SEQ ID NO: 5, 80%-100% identical to amino acids 20-141 of SEQ ID NO: 5, 85%-100% identical to amino acids 20-141 of SEQ ID NO: 5, 90%-100% identical to amino acids 20-141 of SEQ ID NO: 5, 91%-100% identical to amino acids 20-141 of SEQ ID NO: 5, or 95%-100% identical to amino acids 20-141 of SEQ ID NO: 5.

In some embodiments, the present disclosure provides use of an anti-CCR5 antibody or an antigen-binding fragment thereof comprising a heavy chain variable region (VH) and a light chain variable region (VL), wherein the VH comprises a heavy chain CDR1 (VH-CDR1) comprising the amino acid sequence of SEQ ID NO:12, a heavy chain CDR2 (VH-CDR2) comprising the amino acid sequence of SEQ ID NO:13, and a heavy chain CDR3 (VH-CDR3) comprising the amino acid sequence of SEQ ID NO:14; and the VL comprises a light chain CDR1 (VL-CDR1) comprising the amino acid sequence of SEQ ID NO:9, a light chain CDR2 (VL-CDR2) comprising the amino acid sequence of SEQ ID NO:10, and a light chain CDR3 (VL-CDR3) comprising the amino acid sequence of SEQ ID NO:11. In some such embodiments, the VH comprises an amino acid sequence that has at least 70%, 75%, 80%, 85%, 90%, 91%, 92%, 93%, 94%, 95%, 96%, 97%, 98%, or 99% identity with the amino acid sequence of SEQ ID NO:3 or amino acids 20-141 of SEQ ID NO:3, and a VL comprises an amino acid sequence that has at least 70%, 75%, 80%, 85%, 90%, 91%, 92%, 93%, 94%, 95%, 96%, 97%, 98%, or 99% identity with the amino acid sequence of SEQ ID NO:1 or amino acids 20-131 of SEQ ID NO:1, provided that the amino acid sequences of the VH-CDRs (SEQ ID NOS:12-14) and VL-CDRs (SEQ ID NOS:9-11) are unchanged; or the VH comprises an amino acid sequence that has at least 70%, 75%, 80%, 85%, 90%, 91%, 92%, 93%, 94%, 95%, 96%, 97%, 98%, or 99% identity with the amino acid sequence of SEQ ID NO:5 or amino acids 20-141 of SEQ ID NO:5, and a VL comprises an amino acid sequence that has at least 70%, 75%, 80%, 85%, 90%, 91%, 92%, 93%, 94%, 95%, 96%, 97%, 98%, or 99% identity with the amino acid sequence of SEQ ID NO:1 or amino acids 20-131 of SEQ ID NO:1, provided that the amino acid sequences of the VH-CDRs (SEQ ID NOS:12-14) and VL-CDRs (SEQ ID NOS: 9-11) are unchanged.

In some embodiments, the present disclosure provides use of an anti-CCR5 antibody or an antigen-binding fragment thereof comprising: (a) a VH comprising an amino acid sequence of SEQ ID NO:3 or amino acids 20-141 of SEQ ID NO:3, and a VL comprising an amino acid sequence of SEQ ID NO:1 or amino acids 20-131 of SEQ ID NO:1; or (b) a VH comprising an amino acid sequence of SEQ ID NO:5 or amino acids 20-141 of SEQ ID NO:5, and a VL comprising an amino acid sequence of SEQ ID NO:1 or amino acids 20-131 of SEQ ID NO:1.

In a further embodiment, the present disclosure relates to the use of the human antibody designated CCR5mAb004, or a binding fragment thereof. CCR5mAb004 is a fully human mAb, generated using the Abgenix XenoMouse® technology, that specifically recognizes and binds to CCR5. See Roschke et al., *Characterization of a Panel of Novel Human Monoclonal Antibodies That Specifically Antagonize CCR5 and Block HIV Entry*, 44th Annual Interscience CONFERENCE ON ANTIMICROBIAL AGENTS AND CHEMOTHERAPY, Washington, D.C., Oct. 30-Nov. 2, 2004 (2004); HGS Press Release, *Human Genome Sciences Characterizes Panel of Novel Human Monoclonal Antibodies That Specifically Antagonize the CCR5 Receptor and Block HIV-1 Entry*, Nov. 2, 2004 (2004); HGS Press Release, *Human Genome Sciences Begins Dosing of Patients in a Phase 1 Clinical Trial of CCR5 mAb in Patients Infected With HIV-1*, Mar. 30, 2005 (2005).

In one embodiment, the present disclosure relates to the use of the monoclonal antibody PA14, produced by the hybridoma cell line designated PA14 (ATCC Accession No. HB-12610), a binding fragment thereof, or an antibody that competes with monoclonal antibody PA-14 in binding to the CCR5 receptor, in treating or preventing cancer.

In one embodiment of the methods described herein, the antibody or binding fragment thereof comprises a light chain of the antibody. In another embodiment, the antibody or binding fragment thereof comprises a heavy chain of the antibody. In a further embodiment, the antibody or binding fragment thereof comprises an Fab portion of the antibody. In a still further embodiment, the antibody or binding fragment thereof comprises an F(ab')2 portion of the antibody. In an additional embodiment, the antibody or binding fragment thereof comprises an Fd portion of the antibody. In another embodiment, the antibody or binding fragment thereof comprises an Fv portion of the antibody. In a further embodiment, the antibody or binding fragment thereof comprises a variable domain of the antibody. In a still further embodiment, the antibody or binding fragment thereof comprises one or more CDR domains of the antibody. In yet another embodiment, the antibody or binding fragment thereof comprises six CDR domains of the antibody.

In some embodiments, the present disclosure provides use of an anti-CCR5 antibody comprising a Fc region portion. As used herein, "Fc region portion" refers to the heavy chain constant region segment of the Fc fragment (the "fragment crystallizable" region or Fc region) from an antibody, which can include one or more constant domains, such as CH2, CH3, CH4 or any combination thereof. In some embodiments, an Fc region portion includes the CH2 and CH3 domains of an IgG, IgA, or IgD antibody or any combination thereof, or the CH3 and CH4 domains of an IgM or IgE antibody, and any combination thereof. In some embodiments, a CH2CH3 or a CH3CH4 structure has sub-region domains from the same antibody isotype and are human, such as human IgG1, IgG2, IgG3, IgG4, IgA1, IgA2, IgD, IgE, or IgM (e.g., CH2CH3 from human IgG1). By way of background, an Fc region is responsible for the effector functions of an antibody, such as ADCC (antibody-dependent cell-mediated cytotoxicity), CDC (complement-dependent cytotoxicity) and complement fixation, binding to Fc receptors (e.g., CD16, CD32, FcRn), greater half-life in vivo relative to a polypeptide lacking an Fc region, protein A binding, and perhaps even placental transfer (see Capon et al. Nature 337: 525, 1989). In some embodiments, a Fc region portion in an antibody or antigen-binding fragment of the present disclosure is capable of mediating one or more of these effector functions. In some embodiments, a Fc region portion in an antibody or antigen-binding fragment of the present disclosure has normal effector function, meaning having less than 20%, 15%, 10%, 5%, 1% difference in effector function (e.g., ADCC, CDC, half-life or any combination thereof) as compared to a wild type IgG1 antibody.

In some embodiments, the present disclosure provides use of an anti-CCR5 antibody comprising a Fc region portion having an increase in one or more of these effector functions by way of, for example, one or more amino acid substitutions or deletions in the Fc region portion known in the art. An antibody or antigen-binding fragment having a mutated or variant Fc region portion having increased effector function means that the antibody exhibits an increase of at least 20%, 25%, 30%, 35%, 40%, 45%, 50%, 55%, 60%, 65%, 70%, 75%, 80%, 85%, 90%, 95%, or 99% in FcR binding, ADCC, CDC, or any combination thereof, as compared to an antibody having a wild type Fc region portion. In some embodiments, the mutated or variant Fc region portion exhibits increased binding to FcRn, FcγRI (CD64), FcγRIIA (CD32), FcγRIIIA (CD16a), FcγRIIIB (CD16b), or any combination thereof. In some embodiments, the Fc region portion in an antibody or antigen-binding fragment of the present disclosure is a variant Fc region portion having increased ADCC, CDC, half-life, or any combination thereof.

Amino acid modifications (e.g., substitutions) to modify (e.g., improve, reduce, or ablate) Fc functionalities include, for example, the T250Q/M428L, M252Y/S254T/T256E, H433K/N434F, M428L/N434S, E233P/L234V/L235A/G236+A327G/A330S/P331S, E333A, S239D/A330L/I332E, P257I/Q311, K326W/E333S, S239D/I332E/G236A, N297Q, K322A, S228P, L235E+E318A/K320A/K322A, L234A/L235A, and L234A/L235A/P329G mutations, which mutations are summarized and annotated in "Engineered Fc Regions", published by InvivoGen (2011) and available online at www.invivogen.com/PDF/review/review-Engineered-Fc-Regions-invivogen.pdf?utm_source=review&utm_medium=pdf& utm_campaign=review&utm_content=Engineered-Fc-Regions, and are incorporated herein by reference.

In some embodiments, the present disclosure provides use of an anti-CCR5 antibody comprising a Fc region portion having a reduction in one or more of these effector functions or lack one or more effector functions by way of, for example, one or more amino acid substitutions or deletions in the Fc region portion known in the art. An antibody or antigen-binding fragment having a mutated or variant Fc region portion having reduced effector function means that the antibody exhibits a decrease of at least 20%, 25%, 30%, 35%, 40%, 45%, 50%, 55%, 60%, 65%, 70%, 75%, 80%, 85%, 90%, 95%, or 99% in FcR binding, ADCC, CDC, or any combination thereof, as compared to an antibody having a wild type Fc region portion. In some embodiments, the mutated or variant Fc region portion exhibits decreased binding to FcRn, FcγRI (CD64), FcγRIIA (CD32), FcγRIIIA (CD16a), FcγRIIIB (CD16b), or any combination thereof. In some embodiments, the Fc region portion in an antibody or antigen-binding fragment of the present disclosure is a variant Fc region portion having reduced ADCC, CDC, half-life, or any combination thereof. In some embodiments, the Fc region portion is a variant IgG1 Fc region portion comprising a mutation corresponding to amino acid E233P, L234V, L234A, L235A, L235E, ΔG236, G237A, E318A, K320A, K322A, A327G, P329G, A330S, P331S, or any combination thereof, as numbered according to the EU set forth in Kabat. For example, amino acid substitutions L234A, L235E, G237A introduced into an IgG1 Fc region portion reduces binding to FcγRI, FcγRIIa, and FcγRIII receptors, and A330S and P331S introduced into an IgG1 Fc region portion reduces C1q-mediated complement fixation.

In some embodiments, the present disclosure provides use of an anti-CCR5 antibody comprising a Fc region portion having an increase in one or more of these effector functions by way of, for example, one or more amino acid substitutions or deletions in the Fc region portion known in the art. An antibody or antigen-binding fragment having a mutated or variant Fc region portion having increased effector function means that the antibody exhibits an increase of at least 20%, 25%, 30%, 35%, 40%, 45%, 50%, 55%, 60%, 65%, 70%, 75%, 80%, 85%, 90%, 95%, or 99% in FcR binding, ADCC, CDC, or any combination thereof, as compared to an antibody having a wildtype Fc region portion. In some embodiments, the mutated or variant Fc region portion exhibits increased binding to FcRn, FcγRI (CD64), FcγRIIA (CD32), FcγRIIIA (CD16a), FcγRIIIB (CD16b), or any combination thereof. In some embodiments, the Fc region portion in an antibody or antigen-binding fragment of the present disclosure is a variant Fc region portion having increased ADCC, CDC, half-life, or any combination thereof.

In some embodiments, the present disclosure provides use of an anti-CCR5 antibody that is glycosylated. IgG subtype antibodies contain a conserved glycosylation site at amino acid N297 in the CH2 domain of the Fc region portion. In some such embodiments, the Fc region portion in an antibody or antigen-binding fragment of the present disclosure comprises a N297 as numbered according to EU set forth in Kabat. In some embodiments, the present disclosure provides use of an anti-CCR5 antibody that comprises a mutation that alters glycosylation at N297 in the Fc region portion, optionally wherein the mutation that alters glycosylation comprises N297A, N297Q, or N297G. In some embodiments, an antibody or antigen-binding fragment thereof comprising a N297A, N297Q, or N297G mutation exhibits reduced Fc interaction with one or more low affinity FcγR(s), reduced CDC, reduced ADCC, or any combination thereof.

In some embodiments, the present disclosure provides use of an anti-CCR5 antibody that comprises a heavy chain (HC) and a light chain (LC), wherein the HC comprises an amino acid sequence that has at least 90%, 91%, 92%, 93%, 94%, 95%, 96%, 97%, 98%, 99%, or 100% identity with the amino acid sequence of SEQ ID NO:7, and the LC comprises an amino acid sequence that has at least 90%, 91%, 92%, 93%, 94%, 95%, 96%, 97%, 98%, or 99% identity with the amino acid sequence of SEQ ID NO:8

In some embodiments, the present disclosure provides use of an anti-CCR5 antibody that comprises a HC comprising an amino acid sequence that has the amino acid sequence of SEQ ID NO:7, and a LC comprising an amino acid sequence that has the amino acid sequence of SEQ ID NO:8.

In some embodiments, the present disclosure provides use of an anti-CCR5 antibody that comprises a Fc region or a fragment thereof, including a CH2 (or a fragment thereof), a CH3 (or a fragment thereof), or a CH2 and a CH3, wherein the CH2, the CH3, or both can be of any isotype and may contain amino acid substitutions or other modifications as compared to a corresponding wild-type CH2 or CH3, respectively. In certain embodiments, a Fc region of the present disclosure comprises two CH2-CH3 polypeptides that associate to form a dimer.

As used herein, unless otherwise provided, a position of an amino acid residue in the constant region of, for example, a human IgG1 heavy chain is numbered assuming that the variable region of human IgG1 is composed of 128 amino acid residues according to the Kabat numbering convention. The numbered constant region of human IgG1 heavy chain is then used as a reference for numbering amino acid residues in constant regions of other immunoglobulin heavy chains. A position of an amino acid residue of interest in a constant region of an immunoglobulin heavy chain other than human IgG1 heavy chain is the position of the amino acid residue in human IgG1 heavy chain with which the amino acid residue of interest aligns. Alignments between constant regions of human IgG1 heavy chain and other immunoglobulin heavy chains may be performed using software programs known in the art, such as the Megalign program (DNASTAR Inc.) using the Clustal W method with default parameters. According to the numbering system described herein, for example, although human IgG2 CH2 region may have an amino acid deletion near its amino-terminus compared with other CH2 regions, the position of the "N" located at 296 in human IgG2 CH2 is still considered position 297 because this residue aligns with "N" at position 297 in human IgG1 CH2.

In addition, the present disclosure provides use of an anti-CCR5 antibody that comprises a hinge sequence that is typically situated between the Fab and Fc region (but a lower section of the hinge may include an amino-terminal portion of the Fc region). By way of background, an immunoglobulin hinge acts as a flexible spacer to allow the Fab portion to move freely in space. In contrast to the constant regions, hinges are structurally diverse, varying in both sequence and length between immunoglobulin classes and even among subclasses. For example, a human IgG1 hinge region is freely flexible, which allows the Fab fragments to rotate about their axes of symmetry and move within a sphere centered at the first of two inter-heavy chain disulfide bridges. By comparison, a human IgG2 hinge is relatively short and contains a rigid poly-proline double helix stabilized by four inter-heavy chain disulfide bridges, which restricts the flexibility. A human IgG3 hinge differs from the other subclasses by its unique extended hinge region (about four times as long as the IgG1 hinge), containing 62 amino acids (including 21 prolines and 11 cysteines), forming an inflexible poly-proline double helix and providing greater flexibility because the Fab fragments are relatively far away from the Fc fragment. A human IgG4 hinge is shorter than IgG1 but has the same length as IgG2, and its flexibility is intermediate between that of IgG1 and IgG2. Immunoglobulin structure and function are reviewed, for example, in Harlow et al., Eds., Antibodies: A Laboratory Manual, Chapter 14 (Cold Spring Harbor Laboratory, Cold Spring Harbor, 1988).

In some embodiments, the present disclosure provides use of an anti-CCR5 antibody or antigen binding fragment thereof that is chimeric, humanized, or human. Chimeric and humanized forms of non-human (e.g., murine) antibodies can be intact (full length) chimeric immunoglobulins, immunoglobulin chains or antigen binding fragments thereof (such as Fv, Fab, Fab', F(ab')2 or other target-binding subdomains of antibodies), which can contain sequences derived from non-human immunoglobulin. In general, in the humanized antibody or antigen binding fragment thereof most or all of the amino acids outside the CDR regions (e.g., the framework (FR) regions) are replaced with corresponding amino acids derived from human immunoglobulin molecules. In one embodiment of the humanized forms of the antibodies, some, most, or all of the amino acids outside the CDR regions have been replaced with amino acids from human immunoglobulin molecules but where some, most, or all amino acids within one or more CDR regions are unchanged. Small additions, deletions, insertions, substitutions, or modifications of amino acids are permissible as long as they would not abrogate the ability of the antibody to bind a given antigen. A humanized antibody can also comprise at least a portion of a human immunoglobulin constant region (Fc). Suitable human immunoglobulin molecules for use in humanizing a non-human antibody would include IgG1, IgG2, IgG3, IgG4, IgA, and IgM molecules. A "humanized" antibody would retain a similar antigenic specificity as the original antibody, e.g., in the present disclosure, the ability to bind CCR5.

Methods of Use

In one aspect, the present disclosure provides methods of treating, inhibiting, or preventing colon cancer metastasis comprising administering to a subject in need thereof an anti-CCR5 cell receptor binding agent.

In one embodiment, the present disclosure provides methods of treating, inhibiting, or preventing colon cancer metastasis comprising administering to a subject in need thereof an anti-CCR5 cell receptor binding agent comprising: (a) a leronlimab antibody, or binding fragment thereof; (b) a nucleic acid encoding a leronlimab antibody, or binding fragment thereof; (c) a vector comprising a nucleic acid encoding a leronlimab antibody, or binding fragment thereof; (d) a host cell comprising (i) a leronlimab antibody, or binding fragment thereof, (ii) a nucleic acid encoding a leronlimab antibody, or binding fragment thereof, or (iii) a vector comprising a nucleic acid encoding a leronlimab antibody, or binding fragment thereof; or (e) an anti-CCR5 cell receptor binding agent that does not have CCL5 agonist activity.

In one embodiment, the administration results in reduced metastasis of the colon cancer to at least one of the lungs or the liver. In one embodiment, metastasis to the lung is reduced by more than 50%, by 50% to 60%, by 60% to 70%, by 70% to 80%, by 80% to 90%, or by more than 85%. In one embodiment, metastasis to the liver is reduced by more than 40%, by 40% to 50%, by 50% to 60%, or by more than 50%.

In one embodiment, the administration reduces tumor-associated angiogenesis. In one embodiment, total vessel area of vessels feeding a tumor is reduced by more than 40%, by 40% to 50%, by 50% to 60%, by 60% to 70%, or by more than 60%. In one embodiment, vessel length density of vessels feeding a tumor is reduced by more than 40%, by 40% to 50%, by 50% to 60%, or by more than 50%. In one embodiment, the number of vessels feeding a tumor is reduced by more than 40%, by 40% to 50%, by 50% to 60%, by 60% to 70%, by 70% to 80%, or by more than 70%. In one embodiment, the number of larger vessels is reduced by more than 40%, by 40% to 50%, by 50% to 60%, or by more than 50%. In one embodiment, the number of smaller vessels is reduced by more than 40%, by 40% to 50%, by 50% to 60%, by 60% to 70%, by 70% to 80%, or by more than 70%.

In any of the aforementioned embodiments, administration may result in one of increased levels of CD4+CD25+ cells or decreased levels of CD4+CD25− cells in the peripheral blood of the subject. In any of the aforementioned embodiments, the anti-CCR5 cell receptor binding agent may not alter tyrosine kinase phosphorylation in CD4+ cells.

In a further aspect, the present disclosure provides methods of treating or preventing a cancer comprising administering to a subject in need thereof a competitive inhibitor to a CCR5 cell receptor that does not itself have CCL5 agonist activity. In a particular embodiment, a method for preventing a cancer is provided.

In one embodiment, the present disclosure provides a method of preventing a cancer comprising administering to a subject in need thereof a competitive inhibitor to a CCR5 cell receptor that does not itself have CCL5 agonist activity is provided, wherein the competitive inhibitor binds to the ECL-2 loop of the CCR5 cell receptor. In a further embodiment, the competitive inhibitor competes with CCL5 for binding to the CCR5 cell receptor. In a further embodiment, the competitive inhibitor comprises the monoclonal antibody PA14, leronlimab, or CCR5mAb004, or a binding fragment thereof. In a further embodiment, the competitive inhibitor competes for binding with the monoclonal antibody PA14, leronlimab, or CCR5mAb004, or a binding fragment thereof.

In one embodiment, the present disclosure provides a method of preventing a cancer comprising administering to a subject in need thereof: (a) a leronlimab antibody, or binding fragment thereof; (b) a nucleic acid encoding a leronlimab antibody, or binding fragment thereof; (c) a vector comprising a nucleic acid encoding a leronlimab antibody, or binding fragment thereof; or (d) a host cell comprising (i) a leronlimab antibody, or binding fragment thereof, (ii) a nucleic acid encoding a leronlimab antibody, or binding fragment thereof, or (iii) a vector comprising a nucleic acid encoding a leronlimab antibody, or binding fragment thereof. In the aforementioned embodiment, the leronlimab antibody, or binding fragment thereof, may comprise, for example, a leronlimab monoclonal antibody or a scFv.

In one embodiment, the present disclosure provides a method of preventing a cancer comprising administering to a subject in need thereof a leronlimab antibody, or binding fragment thereof.

In any of the aforementioned embodiments, the cancer may be, for example, breast cancer, prostate cancer, colon cancer, melanoma, gastric cancer, ovarian cancer, lung (nonsmall cell) cancer, pancreatic cancer, sarcoma, or blood cell cancer. In a particular embodiment, the cancer is breast cancer. In a particular embodiment, the cancer is prostate cancer. In another particular embodiment, the cancer is colon cancer.

In any of the aforementioned embodiments, preventing the cancer may comprise slowing the growth of the cancer, preventing the formation of a tumor, or limiting or reducing the growth or size of a tumor.

In one embodiment, the competitive inhibitor to a CCR5 cell receptor, such as leronlimab, is administered with a pharmaceutically acceptable carrier. Pharmaceutically acceptable carriers are well known to those skilled in the art. Such pharmaceutically acceptable carriers may include but are not limited to aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, saline, and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers such as those based on Ringer's dextrose, and the like. Preservatives and other additives may also be present, such as, for example, antimicrobials, antioxidants, chelating agents, inert gases, and the like.

The dose of the composition of the invention will vary depending on the subject and upon the particular route of administration used. Dosages can range from 0.1 to 100,000 μg/kg. Based upon the composition, the dose can be delivered continuously, such as by continuous pump, or at periodic intervals, e.g., on one or more separate occasions. Desired time intervals of multiple doses of a particular composition can be determined without undue experimentation by one skilled in the art.

In one embodiment of the instant methods, the antibody or binding fragment thereof is administered to the subject a plurality of times and each administration delivers from 0.01 mg per kg body weight to 50 mg per kg body weight of the antibody or binding fragment thereof to the subject. In another embodiment, each administration delivers from 0.05 mg per kg body weight to 25 mg per kg body weight of the antibody or binding fragment thereof to the subject. In a further embodiment, each administration delivers from 0.1 mg per kg body weight to 10 mg per kg body weight of the antibody or binding fragment thereof to the subject. In a still further embodiment, each administration delivers from 0.5 mg per kg body weight to 5 mg per kg body weight of the antibody or binding fragment thereof to the subject. In another embodiment, each administration delivers from 1 mg per kg body weight to 3 mg per kg body weight of the antibody or binding fragment thereof to the subject. In another embodiment, each administration delivers about 2 mg per kg body weight of the antibody or binding fragment thereof to the subject. In one preferred embodiment, each administration delivers one of a 175 mg, 350 mg, 525 mg, 700 mg, 875 mg, 1050 mg, 1225 mg, 1400 mg, 1575 mg, 1750 mg, 1925 mg, or 2100 mg dose. In a preferred embodiment, the dose may be administered, or self-administered, as a subcutaneous injection. In another preferred embodiment, the dose may be formulated at a concentration of 175 mg/mL.

In one embodiment, the antibody or binding fragment thereof is administered a plurality of times, and a first administration is separated from the subsequent administration by an interval of less than one week. In another embodiment, the first administration is separated from the subsequent administration by an interval of at least one week. In a further embodiment, the first administration is separated from the subsequent administration by an interval of one week. In another embodiment, the first administration is separated from the subsequent administration by an interval of two to four weeks. In another embodiment, the first administration is separated from the subsequent administration by an interval of two weeks. In a further embodiment, the first administration is separated from the subsequent administration by an interval of four weeks. In yet another embodiment, the antibody or binding fragment thereof is administered a plurality of times, and a first administration is separated from the subsequent administration by an interval of at least one month.

In a further embodiment, the antibody or binding fragment thereof is administered to the subject via intravenous infusion. In another embodiment, the antibody or binding fragment thereof is administered to the subject via subcutaneous injection. In another embodiment, the antibody or binding fragment thereof is administered to the subject via intramuscular injection.

In one embodiment, the aforementioned methods may further comprise administering to the subject a cellular therapy, e.g., an autologous or allogeneic immunotherapy; a small molecule; a chemotherapeutic agent; or an inhibitor of CCR5/CCL5 signaling. In one embodiment, an inhibitor of CCR5/CCL5 signaling is administered, and comprises maraviroc, vicriviroc, aplaviroc, SCH-C, TAK-779, PA14 antibody, 2D7 antibody, RoAb13 antibody, RoAb14 antibody, or 45523 antibody.

In one embodiment, the competitive inhibitor to a CCR5 cell receptor, such as leronlimab, is administered alone or in combination with one or more other therapeutic molecules or treatment, such a cellular therapy, e.g., an autologous or allogeneic immunotherapy; a small molecule; a chemotherapeutic; or an inhibitor of CCR5/CCL5 signaling, such as maraviroc, vicriviroc, aplaviroc, SCH-C, TAK-779, PA14 antibody, 2D7 antibody, RoAb13 antibody, RoAb14 antibody, or 45523 antibody. In one embodiment, the methods disclosed herein comprise administering leronlimab in combination with maraviroc, vicriviroc, aplaviroc, SCH-C, TAK-779, PA14 antibody, 2D7 antibody, RoAb13 antibody, RoAb14 antibody, or 45523 antibody.

In one embodiment, the competitive inhibitor to a CCR5 cell receptor, such as leronlimab, is administered in combination with one or more chemotherapeutics such as, for example: alkylating agents such as thiotepa and cyclophosphamide; alkyl sulfonates such as busulfan, improsulfan, and piposulfan; aziridines such as benzodopa, carboquone, meturedopa, and uredopa; ethylenimines and methylamelamines including altretamine, triethylenemelamine, trietylenephosphoramide, triethylenethiophosphaoramide, and trimethylolomelamine; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, and uracil mustard; nitrosureas such as carmustine, chlorozotocin, fotemustine, lomustine, nimustine, and ranimustine; antibiotics such as aclacinomysins, actinomycin, authramycin, azaserine, bleomycins, cactinomycin, calicheamicin, carabicin, caminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, and zorubicin; anti-metabolites such as methotrexate and 5-fluorouracil (5-FU); folic acid analogues such as denopterin, methotrexate, pteropterin, and trimetrexate; purine analogs such as fludarabine, 6-mercaptopurine, thiamiprine, and thioguanine; pyrimidine analogs such as ancitabine, azacitidine, 6-azauridine, carmofur, cytarabine, dideoxyuridine, doxifluridine, enocitabine, floxuridine, and 5-FU; androgens such as calusterone, dromostanolone propionate, epitiostanol, mepitiostane, and testolactone; anti-adrenals such as aminoglutethimide, mitotane, and trilostane; folic acid replenishers such as frolinic acid; aceglatone; aldophosphamide glycoside; am inolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK™; razoxane; sizofiran; spirogermanium; tenuazonic acid; triaziquone; 2, 2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxanes, e.g., paclitaxel (Taxol™, Bristol-Myers Squibb Oncology, Princeton, N.J.) and docetaxel (Taxotere™, Rhone-Poulenc Rorer, Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylornithine (DMFO); retinoic acid; esperamicins; and capecitabine; and pharmaceutically acceptable salts, acids, or derivatives of any of the above.

As used herein, a "small-molecule" CCR5 receptor antagonist includes, for example, a small organic molecule which binds to a CCR5 receptor and inhibits the activity of the receptor. In one embodiment, the small molecule has a molecular weight less than 1,500 daltons. In another embodiment, the small molecule has a molecular weight less than 600 daltons.

In one embodiment, the competitive inhibitor to a CCR5 cell receptor, such as leronlimab, is administered in combination with one or more small molecules, such as SCH-C (Strizki et al., PNAS, 98: 12718-12723 (2001)); SCH-D (SCH 417670; vicriviroc); UK-427,857 (maraviroc; 1-[(4, 6-dimethyl-5-pyrimidinyl) carbonyl]-4-[4-[2-methoxy-1 (R)-4-(trifluoromethyl)phenyl]ethyl-3(S)-methyl-1-piperazinyli-4-methylpiperidine); GW873140; TAK-652; TAK-779; AMD070; AD101; 1,3,4-trisubstituted pyrrolidines (Kim et al., BIOORG. MED. CHEM. LETT., 15: 2129-2134 (2005)); modified 4-piperidinyl-2-phenyl-1-(phenylsulfonylamino)-butanes (Shah et al., BIOORG. MED. CHEM. LETT., 15: 977-982 (2005)); Anibamine TFA, Ophiobolin C, or 19,20-epoxycytochalasin Q (Jayasuriya et al., J. NAT. PROD., 67: 1036-1038 (2004)); 5-(piperidin-1-yl)-3-phenyl-pentylsulfones (Shankaran et al., BIOORG. MED. CHEM. LETT., 14: 3589-3593 (2004)); 4-(heteroarylpiperdin-1-yl-methyl)-pyrrolidin-1-yl-acetic acid antagonists (Shankaran et al., BIOORG. MED. CHEM. LETT., 14: 3419-3424 (2004)); agents containing 4-(pyrazolyl)piperidine side chains (Shu et al., BIOORG. MED. CHEM. LETT., 14: 947-52 (2004); Shen et al., BIOORG. MED. CHEM. LETT., 14: 935-939 (2004); Shen et al., BIOORG. MED. CHEM. LETT., 14: 941-945 (2004)); 3-(pyrrolidin-1-yl)propionic acid analogues (Lynch et al., Org. Lett., 5: 2473-2475 (2003)); [2-(R)-[N-methyl-N-(1-(R)-3-(S)-((4-(3-benzyl-1-ethyl-(1H)-pyrazol-5-yl)piperidin-1-yl)methyl)-4-(S)-(3-fluorophenyl)cyclopent-1-yl)amino]-3-methylbutanoic acid (MRK-1)] (Kumar et al., J. PHARMACOL. EXP. THER., 304: 1161-1171 (2003)); 1,3,4 trisubstituted pyrrolidines bearing 4-aminoheterocycle substituted piperidine side chains (Willoughby et al., BIOORG. MED. CHEM. LETT., 13: 427-431 (2003); Lynch et al., BIOORG. MED. CHEM. LETT., 12: 3001-3004 (2003); Lynch et al., BIOORG. MED. CHEM. LETT., 13: 119-123 (2003); Hale et al., BIOORG. MED. CHEM. LETT., 12: 2997-3000 (2002)); bicyclic isoxazolidines (Lynch et al., BIOORG. MED. CHEM. LETT., 12: 677-679 (2002)); combinatorial synthesis of CCR5 antagonists (Willoughby et al., BIOORG. MED. CHEM. LETT., 11: 3137-41 (2001)); heterocycle-containing compounds (Kim et al., BIOORG. MED. CHEM. LETT., 11: 3103-3106 (2001)); antagonists containing hydantoins (Kim et al., BIOORG. MED. CHEM. LETT., 11: 3099-3102 (2001)); 1,3,4 trisubstituted pyrrolidines (Hale et al., BIOORG. MED. CHEM. LETT., 11: 2741-2745 (2001)); 1-[N-(methyl)-N-(phenylsulfonyl)amino]-2-(phenyl)-4-(4-(N-(alkyl)-N-(benzyloxycarbonyl)amino)piperidin-1-yl)butanes (Finke et al., BIOORG. MED. CHEM. LETT., 11: 2475-2479 (2001)); compounds from the plant *Lippia alva* (Hedge et al., BIOORG. MED. CHEM. LETT., 12: 5339-5342 (2004)); piperazine-based CCR5 antagonists (Tagat et al., J. MED. CHEM., 47: 2405-2408 (2004)); oximino-piperidino-piperidine-based CCR5 antagonists (Palani et al., BIOORG. MED. CHEM. LETT., 13: 709-712 (2003)); rotamers of SCH 351125 (Palani et al., BIOORG. MED. CHEM. LETT., 13: 705-708 (2003)); piperazine-based symmetrical heteroaryl carboxamides (McCombie et al., BIOORG. MED. CHEM. LETT., 13: 567-571 (2003)); oximino-piperidino-piperidine amides (Palani et al., J. MED. CHEM., 45: 3143-3160 (2002)); Sch-351125 and Sch-350634 (Este, CURR. OPIN. INVESTIG. DRUGS, 3: 379-383 (2002)); 1-[(2,4-dimethyl-3-pyridinyl)carbonyl]-4-methyl-4-[3(S)-methyl-4-[1(S)-[4-(trifluoromethyl)phenyl]ethyl]-1-piperazinyl]-piperidine N1-oxide (Sch-350634) (Tagat et al., J. MED. CHEM., 44: 3343-3346 (2001)); 4-[(Z)-(4-bromophenyl)-(ethoxyimino)methyl]-1'-[(2,4-dimethyl-3-pyridinyl)carbonyl]-4'-methyl-1,4'-bipiperidine N-oxide (SCH 351125) (Palani et al., J. MED. CHEM., 44: 3339-3342 (2001)); 2(S)-methyl piperazines (Tagat et al., BIOORG. MED. CHEM. LETT., 11: 2143-2146 (2001)); piperidine-4-carboxamide derivatives (Imamura et al., BIOORG. MED. CHEM., 13: 397-416, 2005); 1-benzazepine derivatives containing a sulfoxide moiety (Seto et al., BIOORG. MED. CHEM. LETT., 13: 363-386 (2005)); anilide derivatives containing a pyridine N-oxide moiety (Seto et al., CHEM. PHARM. BULL. (Tokyo), 52: 818-829 (2004)); 1-benzothiepine 1,1-dioxide and 1-benzazepine derivatives containing a tertiary amine moiety (Seto et al., CHEM. PHARM. BULL. (Tokyo), 52: 577-590 (2004)); N-[3-(4-benzylpiperidin-1-yl)propyl]-N,N'-diphenylureas (Imamura et al., BIOORG. MED. CHEM., 12: 2295-2306 (2004)); 5-oxopyrrolidine-3-carboxamide derivatives (Imamura et al., CHEM. PHARM. BULL. (Tokyo), 52: 63-73 (2004); anilide derivatives with a quaternary ammonium moiety (Shiraishi et al., J. MED. CHEM., 43: 2049-2063 (2000)); AK602/0N04128/GW873140 (Nakata et al., J. VIROL., 79: 2087-2096 (2005)); spirodiketopiperazine derivatives (Maeda et al., J. BIOL. CHEM., 276: 35194-35200 (2001); Maeda et al., J. VIROL., 78: 8654-8662 (2004)); and selective CCR5 antagonists (Thoma et al., J. MED. CHEM., 47: 1939-1955 (2004)).

In one embodiment, the competitive inhibitor to a CCR5 cell receptor, such as leronlimab, is administered in combination with one or more of SCH-C, SCH-D (SCH 417670, or vicriviroc), UK-427,857 (maraviroc), GW873140, TAK-652, TAK-779 AMD070, or AD101. See U.S. Pat. No. 8,821,877.

In one embodiment, the competitive inhibitor to a CCR5 cell receptor, such as leronlimab, exhibits synergistic effects when administered in combination with one or more other therapeutic molecules or treatment, such as a cellular therapy, a small molecule, a chemotherapeutic, or an inhibitor of CCR5/CCL5 signaling. "Synergy" between two or more agents refers to the combined effect of the agents which is greater than their additive effects. Synergistic, additive, or antagonistic effects between agents may be quantified by analysis of the dose-response curves using the Combination Index (CI) method. A CI value greater than 1 indicates antagonism; a CI value equal to 1 indicates an additive effect; and a CI value less than 1 indicates a synergistic effect. In one embodiment, the CI value of a synergistic interaction is less than 0.9. In another embodiment, the CI value is less than 0.8. In another embodiment, the CI value is less than 0.7.

EXAMPLES

Example 1

Effect of Leronlimab on Kinase Activation and Phosphorylation in CD4+ T Cells

CCR5 is a G protein-coupled chemokine receptor (GPCR) that mediates activation and trafficking of cells in response to the chemokines RANTES, MIP-1α, and MIP-1β. CCR5 is expressed in CD4+ T helper-1, T cells, monocyte-derived macrophages, and peripheral blood dendritic cells. Bleul et al., *The HIV coreceptors CXCR4 and CCR5 are differentially expressed and regulated on human T lymphocytes*, PNAS 94(5): 1925-1930 (1997); Loetscher et al., *CCR5 is characteristic of Th1 lymphocytes*, NATURE, 391(6665): 344-345 (1998); Lee et al., *Quantification of CD4, CCR5, and CXCR4 levels on lymphocyte subsets, dendritic cells, and differentially conditioned monocyte-derived macrophages*, PNAS 96(9): 5215-5220 (1999). Chemokine binding to GPCRs alters intracellular cAMP levels, phospholipase and PI3K activation, and tyrosine kinase activity. Rodriguez-Frade et al., *Similarities and Differences in RANTES-and (AOP)-RANTES-triggered Signals: Implications for Chemotaxis*, THE JOURNAL OF CELL BIOLOGY, 144(4): 755-765 (1999); Ward et al., *Chemokines and T lymphocytes: More than an attraction*, IMMUNITY, 9(1): 1-11 (1998). CCR5 binding by MIP-1α, MIP-1β and RANTES (CCL5) occurs with similar affinity and downstream effects. Ward et al., *Chemokines and T lymphocytes: More than an attraction*, IMMUNITY, 9(1): 1-11 (1998).

One such effect is activation of STAT transcriptional factors. Mellado et al., *Chemokine receptor homo- or heterodimerization activates distinct signaling pathways*, THE EMBO JOURNAL, 20(10): 2497-2507 (2001). Chemokine binding to CCR5 stimulates tyrosine kinase (TK) activity and promotes STAT1 and STAT3 activity, which are implicated in the expression of the proto-oncogene c-fos in T cells.

It has previously been shown that the monoclonal antibody leronlimab does not affect cAMP levels when added to CD4+ T cells alone, but diminishes the effect of CCL5 on cAMP levels when administered with CCL5. WO2016/210130. Similarly, although leronlimab alone does not affect chemotaxis of CHO-K1 cells, leronlimab reduces CCL5-induced chemotaxis when administered with CCL5.

WO2016/210130. These studies indicate that leronlimab does not have agonist activity for CCR5 but acts as a competitive inhibitor with CCL5 for binding to CCR5. Because CCR5 is involved in various biochemical pathways, it is important to evaluate possible regulation of these pathways by leronlimab.

To further examine whether leronlimab has antagonist or agonist activity for alternative signaling pathways known to be activated downstream of CCR5 engagement, the effect of leronlimab on specific tyrosine kinase activation was evaluated.

(a) Cell Lines: Blood from 3 healthy donors was collected and centrifuged to allow for the separation and isolation of peripheral blood mononuclear cells (PBMCs). PBMCs were stimulated with 1 μg/mL of Leucoagglutinin PHA-L (2E6 cells/well in 24 well plates). PHA lines were expanded using 30 U/mL IL-2 for 24 hr after stimulation and every other day until FACS for CD4$^+$ CCR5$^+$ T cells (on days 7-10). FACS sorting was conducted using anti-human CD4-percp-Cy5.5 clone RPA-T4, mouse IgG1κ, and anti-human CCR5-PE clone NP-6G4, mouse IgG1κ, each at 25 μg/mL, with a working concentration 0.125 μg/mL. FACS-sorted CD4$^+$ CCR5$^+$ T cells were cultured overnight in IL-2 conditioned media (30 U mL) with or without anti-CD3 and anti-CD28 agonistic antibodies.

(b) Methods: The cell lines were assayed for tyrosine kinase (CREB, ERK, LCK, VASP, ZAP-70) activation in response to leronlimab (1 μg/mL). In addition, the effects of leronlimab on forskolin ("FSK"; 10 μM) and RANTES (0.1 μM) were also tested. Cells were incubated for 15 min at 37° C., then fixed by addition of 16 μL of 16% PFA, and incubated at RT for another 20 min. Cells were then blocked/permeabilized in phosphate-buffered saline with 2% bovine serum albumin and 0.1% Triton-X 100. Cells were stained using fluorescently tagged antibodies directed against phosphorylated kinases, as follows: CREB—Alexa Fluor 488 tag, BD Cat #558435; ERK1/2—Alexa Fluor 488 tag, BD Cat #612592; LCK—PE tag, BD Cat #558552; VASP—FITC tag, Enzo Cat #ALX-804-240F-C100; and ZAP-70—Alexa Fluor 488 tag, BD Cat #558518. Fluorescence intensity in the FL-1 or FL-2 channels was measured using a BD FACScalibur flow cytometer. Population shifts in median fluorescence intensity were used to quantify phosphorylation in cell populations.

In initial experiments, unsorted T cells were exposed to 25 nM phorbol 12-myristate 13-acetate (PMA) to test if TK phosphorylation could be assessed in these cells using established flow-based methods. Baseline phosphorylation levels were observed by comparing median fluorescence intensity values between untreated antibody-stained cells (untreated) and unstained cells (CTL unstained).

Figure 1:
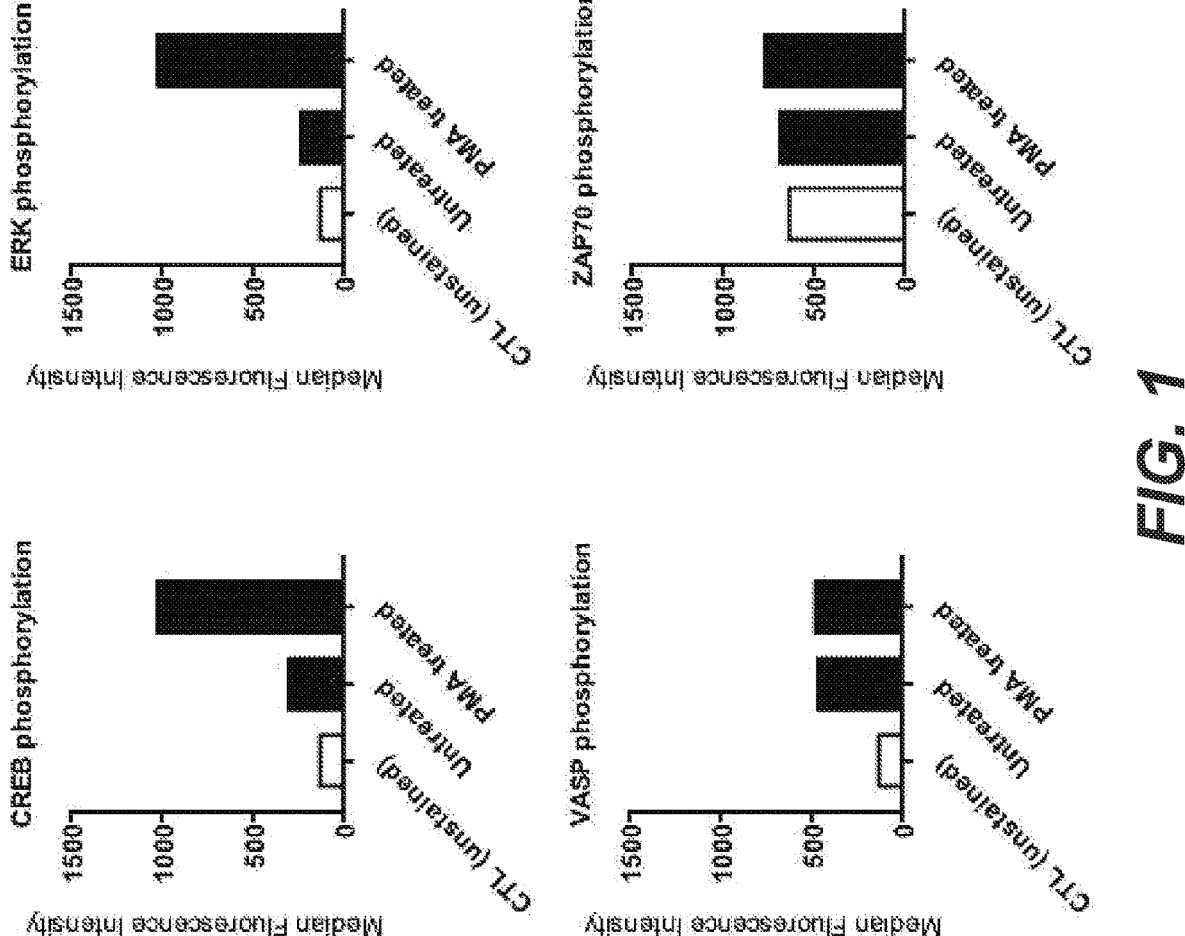
FIG. 1 shows tyrosine kinase activation in response to PMA treatment. Results for unsorted T cells that were either unstained (e.g., no antibody against indicated phosphoproteins; "CTL"), stained but untreated ("untreated"), or treated with 25 nM PMA ("PMA treated"). Median fluorescence intensity values were quantified using FloJo software v10.
Figure 2:
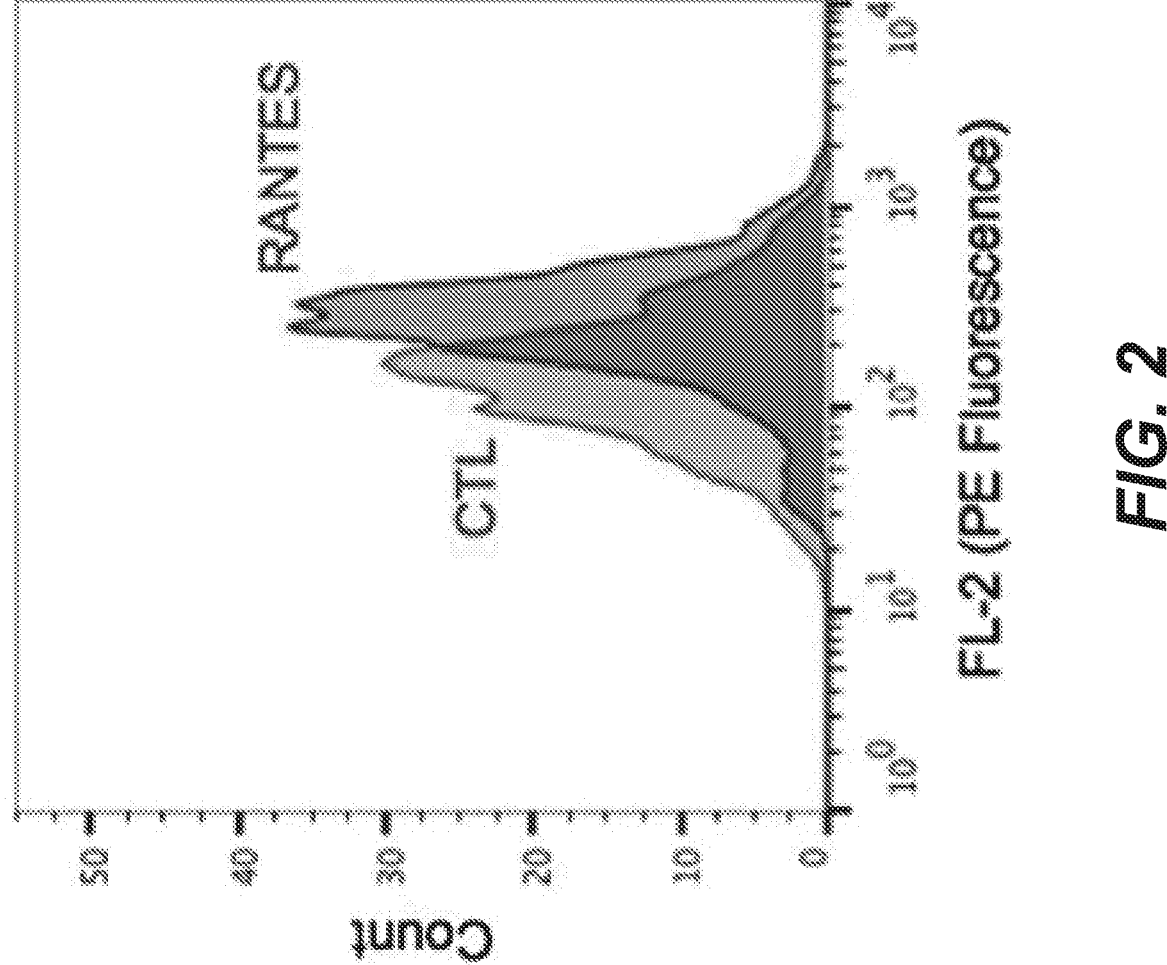
FIG. 2 shows the shifts in median fluorescence intensity histograms in sorted control and RANTES-treated $CD4^+$ $CCR5^+$ T cells. An anti-phospho-LCK antibody was used to quantify phosphorylation of LCK in response to RANTES (0.1 μM) treatment. Results are typical of histograms used to extract subsequent median fluorescence intensity values.

(c) Results: The preliminary experiments using PMA confirmed that tyrosine kinase activation can be quantified in T cells using flow cytometry. PMA treatment increased phosphorylation of CREB and ERK but not that of VASP or ZAP-70 (FIG. 1). Sorted CD4$^+$ CCR5$^+$ T cells also exhibited shifts in median fluorescence intensity histograms (FIG. 2, showing effect of RANTES on LCK phosphorylation).

Figure 3:
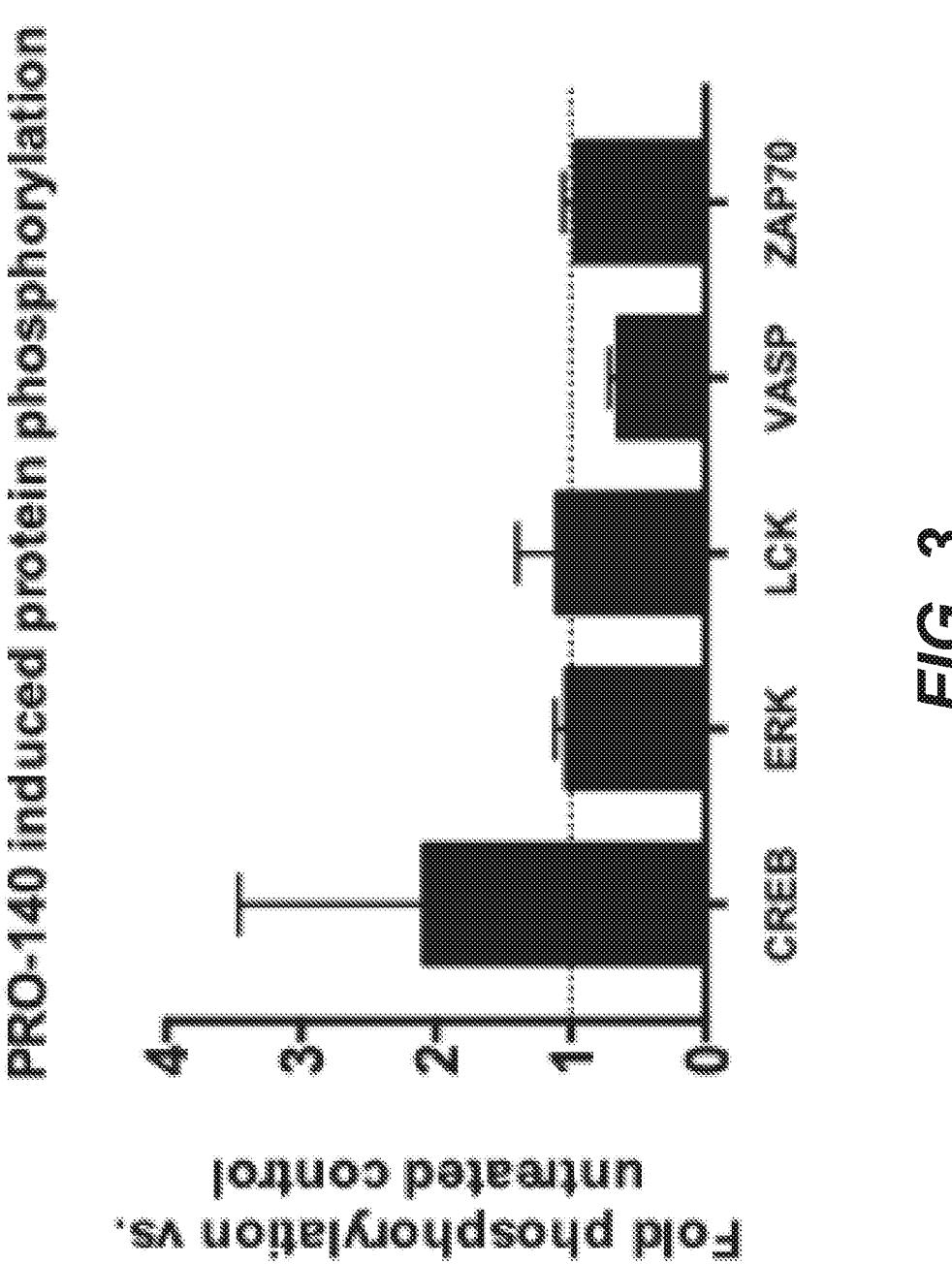
FIG. 3 shows that leronlimab does not induce phosphorylation of CREB, ERK, LCK, VASP, or ZAP-70 (referred to as ZAP-70 or ZAP70 in this application). $CD4^+$ $CCR5^+$-sorted T cells were treated with leronlimab (1 μg/mL) for 15 min prior to fixation and staining to quantify protein phosphorylation. Results are shown as fold phosphorylation compared to respective untreated controls. One-way ANOVA analysis was used to determine if statistically significant changes in phosphorylation occurred; no significant changes were detected.
Figure 4:
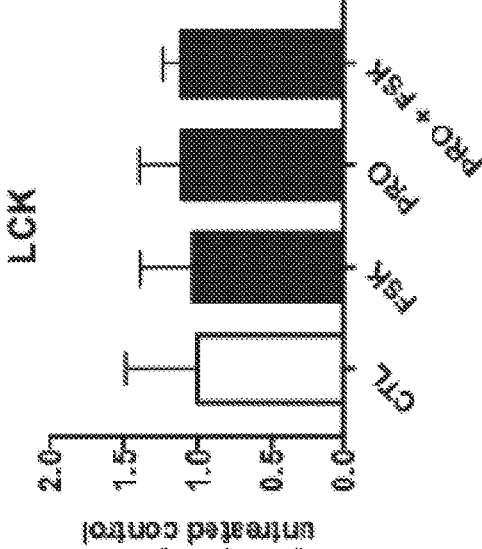
FIG. 4 shows leronlimab does not affect FSK-induced phosphorylation. $CD4^+$ $CCR5^+$-sorted T cells were treated with leronlimab (1 μg/mL) and/or forskolin (10 μM) for 15 min prior to fixation and staining to quantify protein phosphorylation. The results are shown as fold phosphorylation vs. respective untreated controls. The results of a one-way ANOVA analysis indicated that the changes in phosphorylation were not statistically significant.
Figure 4:
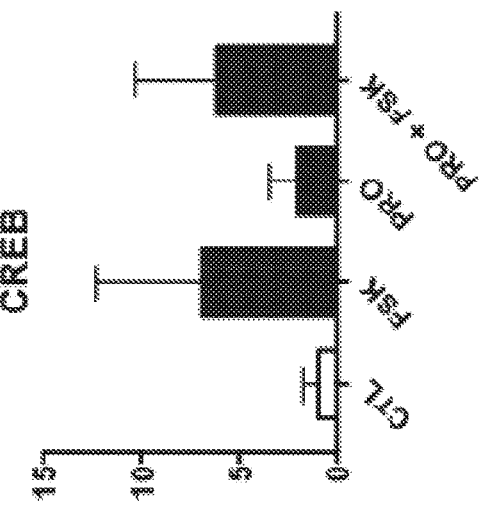
Figure 4:
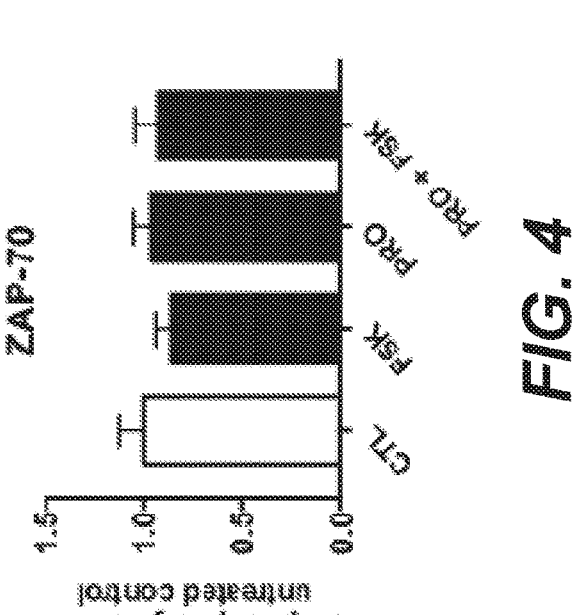
Figure 5:
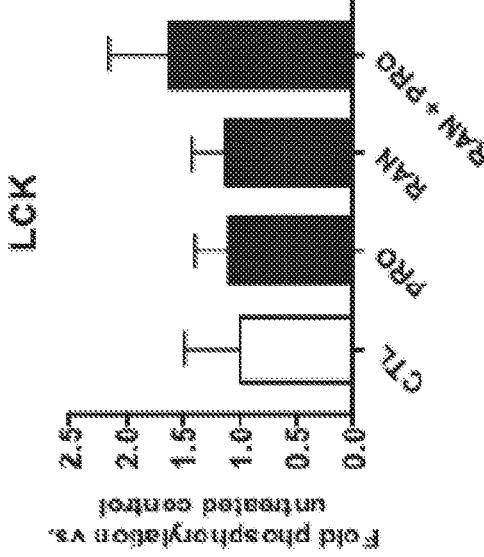
FIG. 5 shows that leronlimab does not affect RANTES-induced phosphorylation. $CD4^+$ $CCR5^+$-sorted T cells were treated with leronlimab (1 μg/mL) and/or RANTES (0.1
Figure 5:
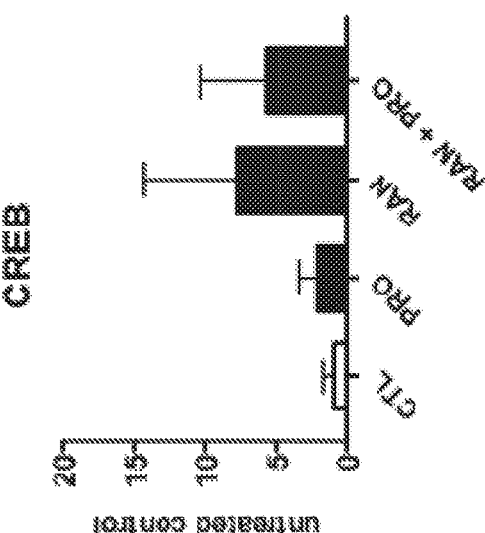
Figure 5:
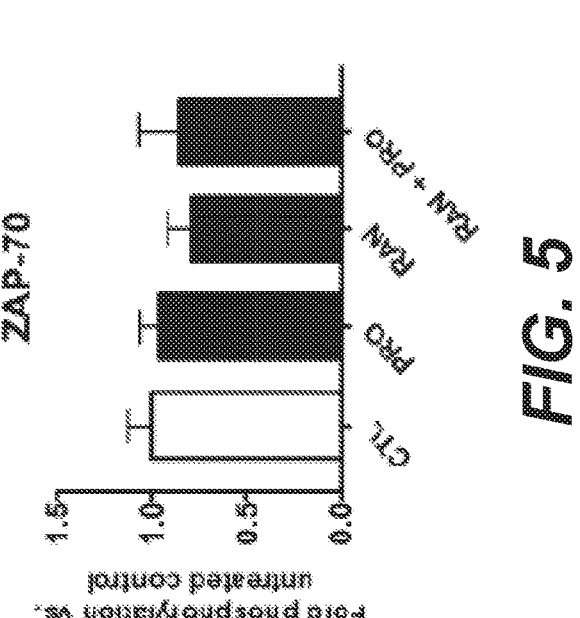

Leronlimab did not alter protein phosphorylation of the kinases tested, and did not alter changes in phosphorylation induced by the adenylyl cyclase agonist forskolin or the CCR5 agonist RANTES. Leronlimab treatment did not produce statistically significant phosphorylation of CREB, ERK, LCK, VASP or ZAP-70 (FIG. 3). Forskolin treatment increased phosphorylation of CREB; pre-treatment with leronlimab did not statistically alter this response (FIG. 4). Likewise, RANTES treatment increased phospho-CREB but this response was not statistically altered by leronlimab pre-treatment (FIG. 5). Consistent with the previous finding that leronlimab does not alter cAMP formation or degradation, the present study indicates that leronlimab also does not significantly alter activation of CREB, ERK, LCK, VASP, or ZAP-70 and that leronlimab does not alter activation of these kinases by forskolin or RANTES. Thus, although leronlimab blunts CCR5 signaling and the ability of CCR5 to lower cAMP concentrations in CD4$^+$ CCR5$^+$-enriched T cells, it has no apparent effects on the activity of the TKs tested here. In addition, leronlimab did not alter basal TK activation or responses induced by forskolin, an agonist that stimulates cAMP synthesis.

(d) Conclusions: The results of this study suggest that leronlimab has no direct effect on kinase activation in CD4$^+$ cell lines nor an apparent ability to inhibit phosphorylation of such kinases by RANTES (a CCR5 agonist) or forskolin.

Example 2

Leronlimab Prevents Cancer in an Immunocompromised Mouse Model

The anti-tumor activity of leronlimab humanized monoclonal antibody was assessed in mouse xenograft models of SW480 human colon carcinoma grown in immunocompromised mice. Although leronlimab did not affect the ability of CCL5 to modulate tyrosine kinase activation in T cells in vitro (Example 1), leronlimab exhibited immunomodulatory effects in mice lacking T cells but not in mice lacking T cells, NK cells, and B cells.

(a) Methods: SW480 human colon carcinoma cells (ATCC) were expanded in culture (DMEM, 10% FBS, antibiotic, antimycotic) and were inoculated subcutaneously (2 million per site, s.c.) in the flanks of male NCr nu/nu mice (Taconic), and male NOD-scid-IL2Rg (NSG) mice (Jackson). Both NCr nu/nu mice and NSG mice lack T cells, which prevents the mouse's immune system from rejecting the transplanted human colon cells. However, NSG mice also lack NK cells and B cells. Mice were randomized to receive Control human IgG or leronlimab i.p. twice per week (Mon, Thu). Tumor diameters were measured 3 times weekly (Mon, Wed, Fri) with calipers, and tumor volume calculated using the formula for a prolate spheroid. The body weight of mice was determined weekly (Wed).

Leronlimab dosage was calculated using "Representative Surface Area to Weight Ratios (km) for Various Species" from: Freireich et al., *Quantitative comparison of toxicity of anticancer agents in mouse, rat, hamster, dog, monkey, and man*, CANCER CHEMOTHER REP., 50:219-44 (1966); and the National Cancer Institute Developmental Therapeutics Program http://dtp.nci.nih.gov. Starting with the human dose of leronlimab=5.8 mg/kg×12 (man-to-mouse conversion factor)=69.6 mg/kg mouse dose; average mouse=0.025 kg, therefore dose is 69.6 mg/kg×0.025 kg=1.74 mg (mouse single dose). This was rounded up to 2.0 mg and designated as the "high dose". A "low dose" (0.2 mg) was also tested. IgG derived from human serum (>95% SDS-PAGE, Sigma, 14506) was used as a non-specific control antibody.

The study was conducted in four parts, using different mouse strains, drug doses, and drug schedules, as shown in Table 1.

TABLE 1

Experimental plan for assessing anti-tumor activity of leronlimab humanized monoclonal antibody in mouse xenograft models of SW480 human colon carcinoma grown in immunocompromised mice.

| | Mouse strain | n | Leronlimab dose | Dosing schedule |
|---|---|---|---|---|
| Part 1 | athymic nude mice (NCr nu/nu) | 16 | High dose (2.0 mg) | i.p. twice weekly starting day 1 |
| Part 2 | athymic nude mice (NCr nu/nu) | 8 | High dose (2.0 mg) | i.p. twice weekly starting day 21 |
| Part 3 | athymic nude mice (NCr nu/nu) | 16 | Low dose (0.2 mg) | i.p. twice weekly starting day 1 |
| Part 4 | NSG mice | 16 | High dose (2.0 mg) | i.p. twice weekly starting day 1 |

(b) Results: Administration of leronlimab at high dose, beginning shortly after mice were inoculated with the colon carcinoma cells, resulted in significantly reduced tumor volume at the end of the study, while administration of leronlimab beginning three weeks after inoculation was associated with no significant difference in tumor volume.

Administration of leronlimab (Part 1, 2 mg i.p. twice a week) resulted in a 62.8% reduction in SW480 tumor volume by day 42 (p=0.014) (FIG. 6). Mice receiving leronlimab exhibited normal weight gain over the course of the study, whereas mice receiving non-specific IgG lost weight during the second half of the study (p=0.047) (FIG. 7).

Treatment of larger established tumors (volume: Control—68.5±47.25; leronlimab—47.25±34.89 mm$^3$) with leronlimab (Part 2, 2 mg i.p. twice a week) commencing on day 21, did not result in significant inhibition of tumor growth (p=0.719) (FIG. 8).

Administration of leronlimab at a reduced dose (Part 3, 0.2 mg i.p. twice a week) induced an 18.3% reduction in SW480 tumor volume by day 42, but did not reach statistical significance (p=0.272) (FIG. 9). During tumor progression in the second half of the study, both groups exhibited similar degree of weight loss (p=0.708) (FIG. 10).

Switching from nude mice (lacking T cells) to a more immunosuppressed host (NSG mice, lacking T, B, and NK cells) resulted in loss of leronlimab anti-tumor efficacy. There was a 32% reduction in tumor volume in the leronlimab groups compared to control, but this did not reach statistical significance (p=0.076) (FIG. 11). There was a similar degree of weight loss in both treatment groups (p=0.61) (FIG. 12).

Conclusion: The results of this study suggest that administering leronlimab shortly after exposure to colon carcinoma cells tends to slow or inhibit tumor growth. However, this effect was dependent on dosage, time between exposure to colon carcinoma cells and administration of leronlimab, and whether the mouse model was lacking T cells or lacking T cells, NK cells, and B cells.

Example 3

Leronlimab Slows Development of xGVHD and Enhances Anti-Tumor Activity in a Humanized Mouse Model of Colon Cancer The anti-tumor activity of leronlimab humanized monoclonal antibody was assessed in mouse xenograft models of SW480 human colon carcinoma grown in humanized mice.

(a) Humanized Mice: Male NOD.Cg-Prkdc$^{scid}$ Il2rg$^{tm1Wjl}$/SzJ, commonly known as the NOD scid IL-2 receptor gamma knockout (NSG, Jackson Laboratory, Stock No. 005557), were 6-8 weeks old when used. Mice received 225 cGy total body irradiation via an X-ray source (Precision X-Rad 320, North Branford, CT). Twenty-four hours after X-ray irradiation, mice were engrafted with human BM cells. De-identified human donor cells were obtained by back-flushing filter packs utilized by the Cleveland Clinic Bone Marrow Transplant program. Fresh (non-frozen) leukocytes were purified by Ficoll-Hypaque gradient centrifugation, washed in phosphate buffered saline (PBS), and assessed for viability (ViCell, Beckman Coulter, Brea, CA). Human BM mononuclear leukocytes were injected into the lateral tail vein (10$^6$ cells/mouse).

(b) Methods:

Heterotopic inoculation: On day 35, when there was clear evidence of human leukocyte engraftment, mice were inoculated in the flanks with 2.5×10$^5$ SW480 human colon carcinoma cells (ATCC, Manassas, VA) that had been stably transfected with luciferase-pcDNA3 (Addgene plasmid #18964; http://n2t.net/addgene:18964; RRID: Addgene_18964) using Lipofectamine. Mice were monitored for clinical symptoms of GvHD (body posture, activity, fur and skin condition, weight loss) two times/week. Peripheral blood was monitored weekly for engraftment utilizing saphenous vein venipuncture (50 µL) collected in K-EDTA tubes. At day 81 over half the mice exhibited >10% weight loss, clinical symptoms of GvHD, and were considered to have reached experimental endpoint.

Orthotopic inoculation: Under ketamine-xylazine anaesthesia, following skin preparation with Betadine scrub and 70% ethanol wipe (×3), the cecum was exposed through a 10 mm incision. 10$^5$ SW480-luc cells in a volume of 10 µL were inoculated into the sub-serosa of the cecum using a 31 gauge needle. Cecum was returned to the peritoneal cavity, muscle and skin were closed in two layers of suture, and mice were allowed to recover.

Euthanasia: Mice were subject to euthanasia by controlled gradient CO$_2$ inhalation (Quietek, NextAdvance, Averill Park, NY) followed by cervical dislocation, and tumors and organs were harvested.

Bioluminescent imaging: To evaluate metastases mice were analyzed using the IVIS Spectrum In Vivo Imaging System (PerkinElmer, Waltham MA). Luciferin doses were 3 mg i.p. for in vivo imaging, and 150 µg/mL for in vitro imaging of excised lungs and liver.

Leronlimab Treatment: Mice were randomized into control and treatment groups of 8 animals each by body weight. Leronlimab was administered intraperitoneally (i.p.) at 2.0 mg/mouse twice weekly. The 2.0 mg dose was calculated to approximate the dose used in a phase 2 human clinical trial for acute GvHD. A single administration of this dose in HIV positive patients has been shown to reduce the HIV load by more than ten-fold. Control mice received normal human IgG (Sigma Aldrich, St. Louis, MO) at the same dose comparison.

(c) Results: CCR5 expression is associated with accelerated tumor growth—The anti-tumor and immunomodulatory effects of leronlimab in a humanized human colon xenograft murine model were characterized. To demonstrate that CCR5 was a functionally relevant marker of colon cancer progression in this xenograft model, SW480 human colon carcinoma cells were FACS sorted according to intensity of CCR5 expression (FIG. 13A). Pools containing the top and bottom 20% expressors were used to inoculate (non-irradiated) NSG mice (FIG. 13B). Tumors that initiated from cells expressing CCR5 most strongly (Hi) generated tumors that grew faster than cells that had the lowest CCR5 expression (Lo), n=4, p=0.019 (FIG. 13C). Hence, in the absence of drug treatment, tumor cells that expressed high numbers of CCR5 displayed a growth advantage in vivo.

Leronlimab slows development of xGVHD—The behavior of SW480 tumors in the context of humanized NSG mice was examined. NSG mice were conditioned with 225 cGy total body irradiation, followed 24h later by inoculation of normal human BM mononuclear cells. Within 3 wk, mice receiving IgG began to exhibit signs of xeno-graft-versus-host-disease (xGVHD), characterized by weight loss, body posture, activity, fur and skin condition (FIGS. 14A and 14B). In non-tumor-bearing mice, leronlimab and IgG treatment was stopped at wk 5, to determine the duration and persistence of anti-GVHD activity conferred by Ab. Systemic symptoms worsened in both IgG and leronlimab groups following cessation of treatment. Signs of xGVHD were delayed until wk 7 in both leronlimab-treated groups. Weight loss accelerated in both tumor-bearing groups compared to non-tumor-bearing animals. Compared to IgG, leronlimab delayed the onset of xGVHD in both tumor-bearing and non-tumor-bearing mice, p=0.001.

Leronlimab enhances anti-tumor activity in humanized mice—The effect of humanization on anti-tumor activity was then assessed. In humanized NSG mice leronlimab effectively delayed tumor progression compared to IgG treatment, and the effect persisted out to day 80 (FIG. 15), p=0.004. In non-humanized NSG mice, the effect of leronlimab treatment upon tumor growth was no different from IgG treatment (p=0.782), indicating the importance of human effector cells in mediating the anti-SW480 activity. Humanization combined with IgG treatment conferred an initial anti-tumor effect that was eventually lost by day 60.

Example 4

Leronlimab Reduces Lung and Liver Metastatic Lesion Growth Rate in a Humanized Mouse Model of Colon Cancer The anti-metastatic activity of leronlimab humanized monoclonal antibody was assessed in mouse xenograft models of SW480 human colon carcinoma grown in humanized mice.

(a) Methods: Humanized mice were orthotopically inoculated with SW480 human colon carcinoma cells as described above. Ten days after orthotopic inoculation of luciferase-labeled colon carcinoma cells into the sub-serosa of the cecum, mice were subject to bioluminescence imaging to verify equivalent starting tumor volumes. On day 45 the study was terminated due to palpable tumors in the abdomen measuring greater than 15 mm diameter, and deteriorating general condition of mice in both treatment groups. Livers and lungs were excised and placed in medium containing luciferin substrate.

(b) Results: There was no significant difference between the early luminescence signal (photons/sec, p/s) emitted by tumors implanted in IgG-treated and leronlimab-treated mice (p=0.074) (FIG. 18A). Liver metastatic burden was decreased 59% in leronlimab-treated mice but did not quite reach significance (p=0.067) (FIG. 18B). Lung metastatic burden was decreased 87% in leronlimab-treated mice compared to IgG-treated animals (p=0.012) (FIG. 18C). Hence the degree of tumor inhibition was more pronounced in the metastatic lesions compared to growth inhibition of the primary subcutaneous tumors.

Example 5

Leronlimab Enhances Expression of Certain Immune Cells

Flow cytometry was used to identify the type(s) of immune cells involved in mediating the anti-tumor effects of leronlimab.

(a) Methods: Peripheral blood (PB) samples were analyzed by flow cytometry. Erythrocytes were lysed with ammonium chloride, cells were washed twice with PBS and stained for 15 min at 4 deg C. in PBS/0.5 mM EDTA/0.5% BSA with the following antibodies: anti-human-CD3-FITC (clone UCHT1, IM1281U), anti-human-CD45-PC7 (clone J.33, IM3548U), anti-mouse-CD45.1-FITC (clone A20), eBioscience (Thermo Fisher) and anti-human-CD56-PE (clone 5.1H11), BioLegend. For human CD45, mouse CD45, and human CD3, results were expressed as percentage of total events. For human CD56, results were expressed as percentage of total events. For analysis of immuno-suppressive cells, True-Nuclear Human Treg Flow Kit (FoxP3 AlexaFluor 488/CD4 PE-Cy5/CD25 PE) was used according to manufacturer directions (BioLegend, San Diego, CA). Samples were analyzed on a Cytomics FC500 Flow Analyzer (Beckman/Coulter).

(b) Results: Peripheral blood from humanized mice was analyzed for changes in immune cell composition. In non-tumor-bearing mice, leronlimab induced a 28.9% increase in circulating NK cells (p=0.017) (FIG. 16, left panel). In tumor-bearing mice, leronlimab treatment resulted in decreased circulating B (40.1%, p=0.037) and NK cells (49.8%, p=0.006), and increased T cells (9.0%, p=0.002) (FIG. 16, left and right panels). This cellular redistribution following leronlimab administration was not secondary to enhanced tumor invasion by human leukocytes. Immunohistochemistry of SW480 tumors was remarkably bland, with staining for B, T, NK cells as well as macrophages (CD206 and CD163) being absent (data not shown).

In peripheral blood of both tumor-bearing and non-tumor-bearing animals, leronlimab induced immunosuppressive human CD4+CD25+ cells (1.47 fold increase, p=0.016; 2.22-fold increase, p=0.0038, respectively) (FIG. 17). Leronlimab also caused a 1.84-fold reduction (p=0.033) of GVHD-promoting circulating human CD4+CD25− cells. There were no FoxP3+ cells detected.

Example 6

Leronlimab Inhibits Tumor-Associated Angiogenesis

The effect of leronlimab on tumor-associated angiogenesis was assessed in mouse xenograft models of SW480 human colon carcinoma grown in humanized mice.

(a) Methods: Blood vessels growing at the periphery of dermally inoculated day 10 SW480 colon carcinoma tumors in humanized NSG mice were photographed using a dissecting microscope at 12.5× magnification. Every visible vessel touching the circumference of the tumor nodule was scored as a single vessel. Two measurements were taken to assess the tumor area (the largest diameter coplanar with the skin, and a second diameter perpendicular to the first). The product of these two measurements was used as an index of tumor area. Images were captured using an operating microscope with 12.5 objective lens (World Precision Instruments, PSMT5, Sarasota, FL). Each experimental group contained eight mice. Tumor photographs were subjected to digital analysis using VESGEN software, where the region of interest representing the tumor mass defined the perimeter of the tumor. The output was a series of color Generation maps (colored vessels on black background) in which the largest diameter vessels were defined as G1, with each subsequent smaller generation represented as G2-G9. The number of blood vessels was expressed based on total vessel area, vessel length density, and vessel diameter.

(b) Results: Quantitative analyses of blood vessels directly feeding into day 10 SW480 colon carcinoma tumors inoculated in the dermis of the flanks revealed a significant decrease in the number of vessels in tumors from leronlimab-treated humanized mice compared with IgG-treated hosts (FIG. 19A), consistent with leronlimab causing an inhibitory effect on neoangiogenesis in the tumor bed. The utilization of VESGEN software allowed detailed comparisons between treatment groups and revealed marked reduction in multiple key properties of the vascular network feeding the tumor, including 62% reduction in total vessel area (pixels) ($p=0.013$), 53% reduction in vessel length density ($p=0.0011$), 61% reduction in number of large vessels ($p=0.0082$), e.g., generations 1-3 (G1-G3), and 80% reduction in number of small vessels ($p=0.017$), e.g., generations 4-9 (G4-G9) (FIG. 19B). Thus, primary tumors from animals with the same initial tumor burden exhibited decreased angiogenesis following treatment with leronlimab.

All of the U.S. patents, U.S. patent application publications, U.S. patent applications, foreign patents, foreign patent applications referred to in this specification and/or listed in the Application Data Sheet, including U.S. Provisional Patent Application No. 62/882,353 filed on Aug. 2, 2019 and U.S. Provisional Patent Application No. 63/047,693 filed on Jul. 2, 2020, are incorporated herein by reference, in their entirety. Aspects of the embodiments can be modified, if necessary to employ concepts of the various patents and applications to provide yet further embodiments. The various embodiments described above can be combined to provide further embodiments.

While specific embodiments of the invention have been illustrated and described, it will be readily appreciated that the various embodiments described above can be combined to provide further embodiments, and that various changes can be made therein without departing from the spirit and scope of the invention. These and other changes can be made to the embodiments in light of the above-detailed description.

In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A method of treating or, inhibiting, metastatic colon cancer comprising administering to a subject in need thereof an anti-CCR5 cell receptor binding agent comprising a leronlimab antibody, or binding fragment thereof in an injected amount of 5.8 mg/kg/week.

2. The method of claim 1, wherein said administration results in reduced metastasis of the cancer to at least one of the lungs or the liver.

3. The method of claim 2, wherein metastasis to the lung is reduced by more than 50%, by 50% to 60%, by 60% to 70%, by 70% to 80%, by 80% to 90%, or by more than 85%.

4. The method of claim 2, wherein metastasis to the liver is reduced by more than 40%, by 40% to 50%, by 50% to 60%, or by more than 50%.

5. The method of claim 1, wherein total vessel area of vessels feeding a tumor is reduced by more than 40%, by 40% to 50%, by 50% to 60%, by 60% to 70%, or by more than 60%.

6. The method of claim 1, wherein vessel length density of vessels feeding a tumor is reduced by more than 40%, by 40% to 50%, by 50% to 60%, or by more than 50%.

7. The method of claim 1, wherein the number of vessels feeding a tumor is reduced by more than 40%, by 40% to 50%, by 50% to 60%, by 60% to 70%, by 70% to 80%, or by more than 70%.

8. The method of claim 7, wherein the number of larger vessels is reduced by more than 40%, by 40% to 50%, by 50% to 60%, or by more than 50%.

9. The method of claim 7, wherein the number of smaller vessels is reduced by more than 40%, by 40% to 50%, by 50% to 60%, by 60% to 70%, by 70% to 80%, or by more than 70%.

10. The method of claim 1, wherein said administration results in one of increased levels of CD4+CD25+ cells or decreased levels of CD4+CD25− cells in the peripheral blood of the subject; or wherein, the anti-CCR5 cell receptor binding agent does not alter tyrosine kinase phosphorylation in CD4+ cells.

11. A method of reducing metastatic burden in a subject having colon cancer, comprising administering to a subject in need thereof an anti-CCR5 cell receptor binding agent comprising a leronlimab antibody, or binding fragment thereof in an injected amount of 5.8 mg/kg/week.

12. The method of claim 11, wherein metastatic burden in a lung is reduced by more than 50%, by 50% to 60%, by 60% to 70%, by 70% to 80%, by 80% to 90%, or by more than 85%.

13. The method of claim 11, wherein metastatic burden in a liver is reduced by more than 40%, by 40% to 50%, by 50% to 60%, or by more than 50%.

14. A method of reducing tumor-associated angiogenesis in a subject having colon cancer, comprising administering to a subject in need thereof an anti-CCR5 cell receptor binding agent comprising a leronlimab antibody, or binding fragment thereof in an injected amount of 5.8 mg/kg/week.

15. The method of claim 14, wherein total vessel area of vessels feeding a tumor is reduced by more than 40%, by 40% to 50%, by 50% to 60%, by 60% to 70%, or by more than 60%.

16. The method of claim 14, wherein vessel length density of vessels feeding a tumor is reduced by more than 40%, by 40% to 50%, by 50% to 60%, or by more than 50%.

17. The method of claim 14, wherein the number of vessels feeding a tumor is reduced by more than 40%, by 40% to 50%, by 50% to 60%, by 60% to 70%, by 70% to 80%, or by more than 70%.

18. The method of claim 17, wherein the number of larger vessels is reduced by more than 40%, by 40% to 50%, by 50% to 60%, or by more than 50%.

19. The method of claim 17, wherein the number of smaller vessels is reduced by more than 40%, by 40% to 50%, by 50% to 60%, by 60% to 70%, by 70% to 80%, or by more than 70%.

20. The method according to claim 1, wherein preventing the cancer comprises slowing the growth of the cancer.

21. The method according to claim 1, wherein preventing the cancer comprises preventing the formation of a tumor.

22. The method according to claim 1, wherein preventing the cancer comprises limiting or reducing the size of a tumor.

* * * * *

SEQUENCE LISTING

```
<160> NUMBER OF SEQ ID NOS: 15

<210> SEQ ID NO 1
<211> LENGTH: 131
<212> TYPE: PRT
<213> ORGANISM: Artificial Sequence
<220> FEATURE:
<223> OTHER INFORMATION: Humanized antidoby PRO140 VL
<220> FEATURE:
<221> NAME/KEY: sig_peptide
<222> LOCATION: 1...19
<223> OTHER INFORMATION: signal peptide at amino acids 1-19

<400> SEQUENCE: 1

Met Lys Leu Pro Val Arg Leu Leu Val Leu Met Phe Trp Ile Pro Ala
1               5                   10                  15

Ser Ser Ser Asp Ile Val Met Thr Gln Ser Pro Leu Ser Leu Pro Val
                20                  25                  30

Thr Pro Gly Glu Pro Ala Ser Ile Ser Cys Arg Ser Ser Gln Arg Leu
            35                  40                  45

Leu Ser Ser Tyr Gly His Thr Tyr Leu His Trp Tyr Leu Gln Lys Pro
    50                  55                  60

Gly Gln Ser Pro Gln Leu Leu Ile Tyr Glu Val Ser Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Val Gly Val Tyr Tyr Cys
                100                 105                 110
```

```
Ser Gln Ser Thr His Val Pro Leu Thr Phe Gly Gln Gly Thr Lys Val
        115                 120                 125

Glu Ile Lys
    130

<210> SEQ ID NO 2
<211> LENGTH: 429
<212> TYPE: DNA
<213> ORGANISM: Artificial Sequence
<220> FEATURE:
<223> OTHER INFORMATION: Humanized antibody PRO140 VL

<400> SEQUENCE: 2
tctagaccac catgaagttg cctgttaggc tgttggtgct gatgttctgg attcctgctt        60
ccagcagtga tattgtgatg acccaatctc cactctccct gcctgtcact cctggagagc       120
cagcctccat ctcttgcaga tctagtcagc gccttctgag cagttatgga catacctatt       180
tacattggta cctacagaag ccaggccagt ctccacagct cctgatctac gaagtttcca       240
accgattttc tggggtccca gacaggttca gtggcagtgg gtcagggaca gatttcacac       300
ttaagatcag tagagtggag gctgaggatg tgggagttta ttactgctct caaagtacac       360
atgttcctct cacgttcgga caggggacca aggtggaaat aaaacgtaag tagtcttctc       420
aactctaga                                                                 429

<210> SEQ ID NO 3
<211> LENGTH: 141
<212> TYPE: PRT
<213> ORGANISM: Artificial Sequence
<220> FEATURE:
<223> OTHER INFORMATION: Humanized antibody PRO140 #2 VH
<220> FEATURE:
<221> NAME/KEY: sig_peptide
<222> LOCATION: 1...19
<223> OTHER INFORMATION: signal peptide at amino acids 1-19

<400> SEQUENCE: 3

Met Glu Trp Ser Gly Val Phe Ile Phe Leu Leu Ser Val Thr Ala Gly
1               5                   10                  15

Val His Ser Glu Val Gln Leu Val Glu Ser Gly Gly Gly Leu Val Lys
            20                  25                  30

Pro Gly Gly Ser Leu Arg Leu Ser Cys Ala Ala Ser Gly Tyr Thr Phe
        35                  40                  45

Ser Asn Tyr Trp Ile Gly Trp Val Arg Gln Ala Pro Gly Lys Gly Leu
    50                  55                  60

Glu Trp Ile Gly Asp Ile Tyr Pro Gly Gly Asn Tyr Ile Arg Asn Asn
65                  70                  75                  80

Glu Lys Phe Lys Asp Lys Thr Thr Leu Ser Ala Asp Thr Ser Lys Asn
            85                  90                  95

Thr Ala Tyr Leu Gln Met Asn Ser Leu Lys Thr Glu Asp Thr Ala Val
            100                 105                 110

Tyr Tyr Cys Gly Ser Ser Phe Gly Ser Asn Tyr Val Phe Ala Trp Phe
            115                 120                 125

Thr Tyr Trp Gly Gln Gly Thr Leu Val Thr Val Ser Ser
    130                 135                 140

<210> SEQ ID NO 4
<211> LENGTH: 457
<212> TYPE: DNA
<213> ORGANISM: Artificial Sequence
<220> FEATURE:
```

<223> OTHER INFORMATION: Humanized antibody PRO#2 VH

<400> SEQUENCE: 4
acgcgtccac catggaatgg agcggagtct ttatctttct cctgtcagta actgcaggtg      60
tccactccga ggtgcagctg gtggagtctg tggaggcttt ggtaaagcct ggaggttccc     120
ttagactctc ctgtgcagcc tctggttaca ctttcagtaa ctattggatc ggatgggtcc     180
gccaggctcc aggcaaaggg ctggagtgga ttggcgatat ctaccctgga gggaactaca     240
tcaggaacaa tgagaagttc aaggacaaga ccaccctgtc agcagatact ccaagaaca     300 cagcctatct gcaaatgaac agcctgaaaa ccgaggacac agccgtgtat tactgtggaa     360
gcagcttcgg tagtaactac gtgttcgcct ggtttactta ctggggccaa gggactctgg     420
tcacagtctc ctcaggtgag tccttaaaac ctctaga                             457

<210> SEQ ID NO 5
<211> LENGTH: 141
<212> TYPE: PRT
<213> ORGANISM: Artificial Sequence
<220> FEATURE:
<223> OTHER INFORMATION: Humanized antibody PRO140#1 VH
<220> FEATURE:
<221> NAME/KEY: sig_peptide
<222> LOCATION: 1...19
<223> OTHER INFORMATION: signal peptide at amino acids 1-19

<400> SEQUENCE: 5

Met Glu Trp Ser Gly Val Phe Ile Phe Leu Leu Ser Val Thr Ala Gly
1               5                   10                  15

Val His Ser Gln Val Gln Leu Val Gln Ser Gly Pro Asp Val Lys Lys
            20                  25                  30

Pro Gly Thr Ser Met Lys Met Ser Cys Lys Thr Ser Gly Tyr Thr Phe
        35                  40                  45

Ser Asn Tyr Trp Ile Gly Trp Val Arg Gln Ala Pro Gly Gln Gly Leu
    50                  55                  60

Glu Trp Ile Gly Asp Ile Tyr Pro Gly Gly Asn Tyr Ile Arg Asn Asn
65                  70                  75                  80

Glu Lys Phe Lys Asp Lys Thr Thr Leu Thr Ala Asp Thr Ser Thr Ser
                85                  90                  95

Thr Ala Tyr Met Gln Leu Gly Ser Leu Arg Ser Glu Asp Thr Ala Val
            100                 105                 110

Tyr Tyr Cys Gly Ser Ser Phe Gly Ser Asn Tyr Val Phe Ala Trp Phe
        115                 120                 125

Thr Tyr Trp Gly Gln Gly Thr Leu Val Thr Val Ser Ser
    130                 135                 140

<210> SEQ ID NO 6
<211> LENGTH: 457
<212> TYPE: DNA
<213> ORGANISM: Artificial Sequence
<220> FEATURE:
<223> OTHER INFORMATION: Humanized antibody PRO#1 VH

<400> SEQUENCE: 6
tctagaccac catggaatgg agcggggtct ttatctttct cctgtcagta actgcaggtg      60
tccactccca ggtccaactg gtgcagtctg acctgatgt gaaaaagcct gggacttcaa     120
tgaagatgtc ctgcaagacg tctggataca ccttcagtaa ctattggatc ggatgggtta     180
ggcaggcgcc tggacaaggc cttgagtgga ttggagatat ttaccctgga gggaactata     240

-continued

```
tcaggaacaa tgagaagttc aaggacaaga ccacactgac ggcagacaca tcgaccagca      300
cggcctacat gcaacttggc agcctgagat ctgaagacac tgccgtctat tactgtggaa      360
gcagcttcgg tagtaactac gtgttcgcct ggtttactta ctggggccaa gggactctgg      420
tcacagtctc ctcaggtgag tccttaaaac ctctaga                               457
```

```
<210> SEQ ID NO 7
<211> LENGTH: 449
<212> TYPE: PRT
<213> ORGANISM: Artificial Sequence
<220> FEATURE:
<223> OTHER INFORMATION: Humanized antibody heavy chain

<400> SEQUENCE: 7

Glu Val Gln Leu Val Glu Ser Gly Gly Gly Leu Val Lys Pro Gly Gly
1               5                   10                  15

Ser Leu Arg Leu Ser Cys Ala Ala Ser Gly Tyr Thr Phe Ser Asn Tyr
            20                  25                  30

Trp Ile Gly Trp Val Arg Gln Ala Pro Gly Lys Gly Leu Glu Trp Ile
        35                  40                  45

Gly Asp Ile Tyr Pro Gly Gly Asn Tyr Ile Arg Asn Asn Glu Lys Phe
    50                  55                  60

Lys Asp Lys Thr Thr Leu Ser Ala Asp Thr Ser Lys Asn Thr Ala Tyr
65                  70                  75                  80

Leu Gln Met Asn Ser Leu Lys Thr Glu Asp Thr Ala Val Tyr Tyr Cys
                85                  90                  95

Gly Ser Ser Phe Gly Ser Asn Tyr Val Phe Ala Trp Phe Thr Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
        195                 200                 205

His Lys Pro Ser Asn Thr Lys Val Asp Lys Arg Val Glu Ser Lys Tyr
    210                 215                 220

Gly Pro Pro Cys Pro Ser Cys Pro Ala Pro Glu Phe Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
        275                 280                 285

Ala Lys Thr Lys Pro Arg Glu Glu Gln Phe Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
```

```
               325             330             335
Thr Ile Ser Lys Ala Lys Gly Gln Pro Arg Glu Pro Gln Val Tyr Thr
           340             345             350

Leu Pro Pro Ser Gln Glu Glu Met Thr Lys Asn Gln Val Ser Leu Thr
           355             360             365

Cys Leu Val Lys Gly Phe Tyr Pro Ser Asp Ile Ala Val Glu Trp Glu
           370             375             380

Ser Asn Gly Gln Pro Glu Asn Asn Tyr Lys Thr Thr Pro Pro Val Leu
385             390             395             400

Asp Ser Asp Gly Ser Phe Phe Leu Tyr Ser Arg Leu Thr Val Asp Lys
               405             410             415

Ser Arg Trp Gln Glu Gly Asn Val Phe Ser Cys Ser Val Met His Glu
               420             425             430

Ala Leu His Asn His Tyr Thr Gln Lys Ser Leu Ser Leu Ser Leu Gly
           435             440             445

Lys
```

<210> SEQ ID NO 8
<211> LENGTH: 219
<212> TYPE: PRT
<213> ORGANISM: Artificial Sequence
<220> FEATURE:
<223> OTHER INFORMATION: Humanized antibody light chain

<400> SEQUENCE: 8

```
Asp Ile Val Met Thr Gln Ser Pro Leu Ser Leu Pro Val Thr Pro Gly
1               5               10              15

Glu Pro Ala Ser Ile Ser Cys Arg Ser Ser Gln Arg Leu Leu Ser Ser
               20              25              30

Tyr Gly His Thr Tyr Leu His Trp Tyr Leu Gln Lys Pro Gly Gln Ser
           35              40              45

Pro Gln Leu Leu Ile Tyr Glu Val Ser Asn Arg Phe Ser Gly Val Pro
       50              55              60

Asp Arg Phe Ser Gly Ser Gly Ser Gly Thr Asp Phe Thr Leu Lys Ile
65              70              75              80

Ser Arg Val Glu Ala Glu Asp Val Gly Val Tyr Tyr Cys Ser Gln Ser
               85              90              95

Thr His Val Pro Leu Thr Phe Gly Gln Gly Thr Lys Val Glu Ile Lys
           100             105             110

Arg Thr Val Ala Ala Pro Ser Val Phe Ile Phe Pro Pro Ser Asp Glu
           115             120             125

Gln Leu Lys Ser Gly Thr Ala Ser Val Val Cys Leu Leu Asn Asn Phe
       130             135             140

Tyr Pro Arg Glu Ala Lys Val Gln Trp Lys Val Asp Asn Ala Leu Gln
145             150             155             160

Ser Gly Asn Ser Gln Glu Ser Val Thr Glu Gln Asp Ser Lys Asp Ser
               165             170             175

Thr Tyr Ser Leu Ser Ser Thr Leu Thr Leu Ser Lys Ala Asp Tyr Glu
           180             185             190

Lys His Lys Val Tyr Ala Cys Glu Val Thr His Gln Gly Leu Ser Ser
           195             200             205

Pro Val Thr Lys Ser Phe Asn Arg Gly Glu Cys
       210             215
```

<210> SEQ ID NO 9

-continued

```
<211> LENGTH: 16
<212> TYPE: PRT
<213> ORGANISM: Artificial Sequence
<220> FEATURE:
<223> OTHER INFORMATION: Humanized antibody LCDR1

<400> SEQUENCE: 9

Arg Ser Ser Gln Arg Leu Leu Ser Ser Tyr Gly His Thr Tyr Leu His
1               5                   10                  15

<210> SEQ ID NO 10
<211> LENGTH: 7
<212> TYPE: PRT
<213> ORGANISM: Artificial Sequence
<220> FEATURE:
<223> OTHER INFORMATION: Humanized antibody LCDR2

<400> SEQUENCE: 10

Glu Val Ser Asn Arg Phe Ser
1               5

<210> SEQ ID NO 11
<211> LENGTH: 9
<212> TYPE: PRT
<213> ORGANISM: Artificial Sequence
<220> FEATURE:
<223> OTHER INFORMATION: Humanized antibody LCDR3

<400> SEQUENCE: 11

Ser Gln Ser Thr His Val Pro Leu Thr
1               5

<210> SEQ ID NO 12
<211> LENGTH: 5
<212> TYPE: PRT
<213> ORGANISM: Artificial Sequence
<220> FEATURE:
<223> OTHER INFORMATION: Humanized antibody HCDR1

<400> SEQUENCE: 12

Asn Tyr Trp Ile Gly
1               5

<210> SEQ ID NO 13
<211> LENGTH: 17
<212> TYPE: PRT
<213> ORGANISM: Artificial Sequence
<220> FEATURE:
<223> OTHER INFORMATION: Humanized antibody HCDR2

<400> SEQUENCE: 13

Asp Ile Tyr Pro Gly Gly Asn Tyr Ile Arg Asn Asn Glu Lys Phe Lys
1               5                   10                  15

Asp

<210> SEQ ID NO 14
<211> LENGTH: 13
<212> TYPE: PRT
<213> ORGANISM: Artificial Sequence
<220> FEATURE:
<223> OTHER INFORMATION: Humanized antibody HCDR3

<400> SEQUENCE: 14

Ser Phe Gly Ser Asn Tyr Val Phe Ala Trp Phe Thr Tyr
1               5                   10
```

-continued

```
<210> SEQ ID NO 15
<211> LENGTH: 352
<212> TYPE: PRT
<213> ORGANISM: Homo sapiens
<220> FEATURE:
<223> OTHER INFORMATION: CCR5 NCBI Reference Sequence: NP_000570.1

<400> SEQUENCE: 15

Met Asp Tyr Gln Val Ser Ser Pro Ile Tyr Asp Ile Asn Tyr Tyr Thr
1               5                   10                  15

Ser Glu Pro Cys Gln Lys Ile Asn Val Lys Gln Ile Ala Ala Arg Leu
            20                  25                  30

Leu Pro Pro Leu Tyr Ser Leu Val Phe Ile Phe Gly Phe Val Gly Asn
        35                  40                  45

Met Leu Val Ile Leu Ile Leu Ile Asn Cys Lys Arg Leu Lys Ser Met
    50                  55                  60

Thr Asp Ile Tyr Leu Leu Asn Leu Ala Ile Ser Asp Leu Phe Phe Leu
65                  70                  75                  80

Leu Thr Val Pro Phe Trp Ala His Tyr Ala Ala Ala Gln Trp Asp Phe
                85                  90                  95

Gly Asn Thr Met Cys Gln Leu Leu Thr Gly Leu Tyr Phe Ile Gly Phe
            100                 105                 110

Phe Ser Gly Ile Phe Phe Ile Ile Leu Leu Thr Ile Asp Arg Tyr Leu
        115                 120                 125

Ala Val Val His Ala Val Phe Ala Leu Lys Ala Arg Thr Val Thr Phe
    130                 135                 140

Gly Val Val Thr Ser Val Ile Thr Trp Val Val Ala Val Phe Ala Ser
145                 150                 155                 160

Leu Pro Gly Ile Ile Phe Thr Arg Ser Gln Lys Glu Gly Leu His Tyr
                165                 170                 175

Thr Cys Ser Ser His Phe Pro Tyr Ser Gln Tyr Gln Phe Trp Lys Asn
            180                 185                 190

Phe Gln Thr Leu Lys Ile Val Ile Leu Gly Leu Val Leu Pro Leu Leu
        195                 200                 205

Val Met Val Ile Cys Tyr Ser Gly Ile Leu Lys Thr Leu Leu Arg Cys
    210                 215                 220

Arg Asn Glu Lys Lys Arg His Arg Ala Val Arg Leu Ile Phe Thr Ile
225                 230                 235                 240

Met Ile Val Tyr Phe Leu Phe Trp Ala Pro Tyr Asn Ile Val Leu Leu
                245                 250                 255

Leu Asn Thr Phe Gln Glu Phe Phe Gly Leu Asn Asn Cys Ser Ser Ser
            260                 265                 270

Asn Arg Leu Asp Gln Ala Met Gln Val Thr Glu Thr Leu Gly Met Thr
        275                 280                 285

His Cys Cys Ile Asn Pro Ile Ile Tyr Ala Phe Val Gly Glu Lys Phe
    290                 295                 300

Arg Asn Tyr Leu Leu Val Phe Phe Gln Lys His Ile Ala Lys Arg Phe
305                 310                 315                 320

Cys Lys Cys Cys Ser Ile Phe Gln Gln Glu Ala Pro Glu Arg Ala Ser
                325                 330                 335

Ser Val Tyr Thr Arg Ser Thr Gly Glu Gln Glu Ile Ser Val Gly Leu
                340                 345                 350
```